(12) United States Patent
Panzner et al.

(10) Patent No.: US 8,193,246 B2
(45) Date of Patent: Jun. 5, 2012

(54) LIPIDS AND LIPID ASSEMBLIES COMPRISING TRANSFECTION ENHANCER ELEMENTS

(75) Inventors: Steffen Panzner, Halle (DE); Evgenios Siepi, Leipzig (DE); Silke Lutz, Halle (DE); Christian Reinsch, Halle (DE); Claudia Müller, Nerchau (DE)

(73) Assignee: Marina Biotech, Inc., Bothell, WA (US)

( * ) Notice: Subject to any disclaimer, the term of this patent is extended or adjusted under 35 U.S.C. 154(b) by 657 days.

(21) Appl. No.: 12/004,154

(22) Filed: Dec. 19, 2007

(65) Prior Publication Data

US 2008/0306153 A1 Dec. 11, 2008

Related U.S. Application Data

(63) Continuation-in-part of application No. 11/642,347, filed on Dec. 19, 2006, now abandoned.

(30) Foreign Application Priority Data

Dec. 19, 2006 (EP) .................................... 06256450
Sep. 25, 2007 (EP) .................................... 07117189

(51) Int. Cl.
*A61K 31/20* (2006.01)
*C07C 53/122* (2006.01)
*C07C 231/00* (2006.01)

(52) U.S. Cl. ................. 514/588; 554/1; 554/35; 554/51
(58) Field of Classification Search .................. None
See application file for complete search history.

(56) References Cited

U.S. PATENT DOCUMENTS

| | | | | |
|---|---|---|---|---|
| 5,635,487 | A | 6/1997 | Wolff et al. ................. | 514/44 A |
| 5,785,992 | A | 7/1998 | Ansell et al. ................. | 424/450 |
| 5,965,434 | A | 10/1999 | Wolff et al. ................. | 435/320.1 |
| 6,294,191 | B1 | 9/2001 | Meers et al. ................. | 424/450 |
| 6,441,206 | B1 * | 8/2002 | Mikkonen et al. ............ | 552/540 |
| 6,756,054 | B1 | 6/2004 | Miller et al. ................. | 424/450 |
| 7,407,947 | B2 * | 8/2008 | Panzner et al. .............. | 514/176 |
| 2008/0145413 | A1 | 6/2008 | Panzner et al. .............. | 424/450 |

FOREIGN PATENT DOCUMENTS

| | | | |
|---|---|---|---|
| DE | 19753182 | | 7/1999 |
| EP | WO02066489 | * | 8/2002 |
| EP | 1 938 843 | | 7/2008 |
| WO | 86/04232 | | 7/1986 |
| WO | WO86/04232 | * | 12/1986 |
| WO | 97/19675 | | 6/1997 |
| WO | 00/11007 | | 3/2000 |
| WO | WO 02/34236 | | 5/2002 |
| WO | WO 2005/007196 | | 1/2005 |
| WO | WO 2005/105152 | | 11/2005 |
| WO | WO 2006/016097 | | 2/2006 |
| WO | WO 2006/069782 | | 7/2006 |
| WO | WO 2006/105361 | | 10/2006 |

OTHER PUBLICATIONS

Kolena et al (Biochimica et Biophysica Acta. 1989; 979: 279-286).*
Fattal et al. (Advanced Drug Delivery Reviews. 2004; 56: 931-946).*
Hafez et al. (Gene Therapy. 2001; 8: 1188-1196).*
Hafez et al. (Biophysical Journal. 2000; 79: 1438-1446.*
Hafez et al. (Biochimica et Biophysica Acta. 2000; 1463: 107-114).*
Beaucage et al. (1981), Tetrahedron Letters, 22:1859-1862.
Bergbreiter et al. (1975), J. Org. Chem., 40:779-782.
Brown et al. (1979), Methods in Enzymology, 68:109-151.
Budker et al. (1996), Nature Biotechnology, 14:760-764.
Cho-Chung et al. (1999), Current Opinion in Molecular Therapeutics, 1:386-392.
Dass (2002), Journal of Pharmacy and Pharmacology, 54:593-601.
DeGrip et al. (1998), Biochem. J., 330: 667-674.
Filion et al. (1997), Biochimica et Biophysica Acta, 1329:345-356.
Geall et al. (1998), Chem. Commun., 2035-2036.
Graminski et al. (2002), Bioorganic & Medicinal Chemistry Letters, 12:35-40.
Hirko et al. (2003), Current Medicinal Chemistry, 10:1185-1193.
Kulikowska et al. (2004), Acta Biochimica Polonica, 51:493-531.
Matteucci et al. (1981), Journal American Chemical Society, 103:3185-3191.
Miller et al. (1995), FASEB J., 9:190-199.
Morrissey et al. (2005), Nature Biotechnology, 23:1002-1007.
Narang et al. (1979), Methods in Enzymology, 68:90-98.
Spagnou et al. (2004), Biochemistry, 43:13348-13356.
Stegmann et al. (1990), EMBO Journal, 9:4231-4241.
Thomas et al. (2003), Nature Reviews, Genetics, 4:346-358.
Uneyama et at (1991), Tetrahedron Letters, 32:1459-1462.
Wheeler et al. (1999), Gene Therapy, 6:271-281.
Yoon et al. (1973), J. Org. Chem., 38:2786-2792.

* cited by examiner

*Primary Examiner* — Scott Long
(74) *Attorney, Agent, or Firm* — Mintz Levin Cohn Ferris Glovsky and Popeo, P.C.; Ivor R. Elrifi

(57) ABSTRACT

Lipid assemblies, such as liposomes, comprising transfection enhancer elements (TEE's), which are complexed with the lipid assemblies by means of ionic interactions, or lipids incorporating such TEE's are disclosed for enhancing the fusogenicity of the lipid assemblies. The TEE's have the formula:

hydrophobic moiety-pH sensitive hydrophilic moiety (II)

The pH sensitive hydrophilic moiety of each TEE is a weak acid having a pka of between 2 and 6 or a zwitterionic structure comprising a combination of acidic groups with weak bases having a pKa of between 3 and 8. Lipids incorporating one or more such TEEs have the formula (I):

Lipid moiety-[Hydrophobic moiety-pH sensitive hydrophilic moiety] (I).

29 Claims, 15 Drawing Sheets

A:

B:

A:

B:

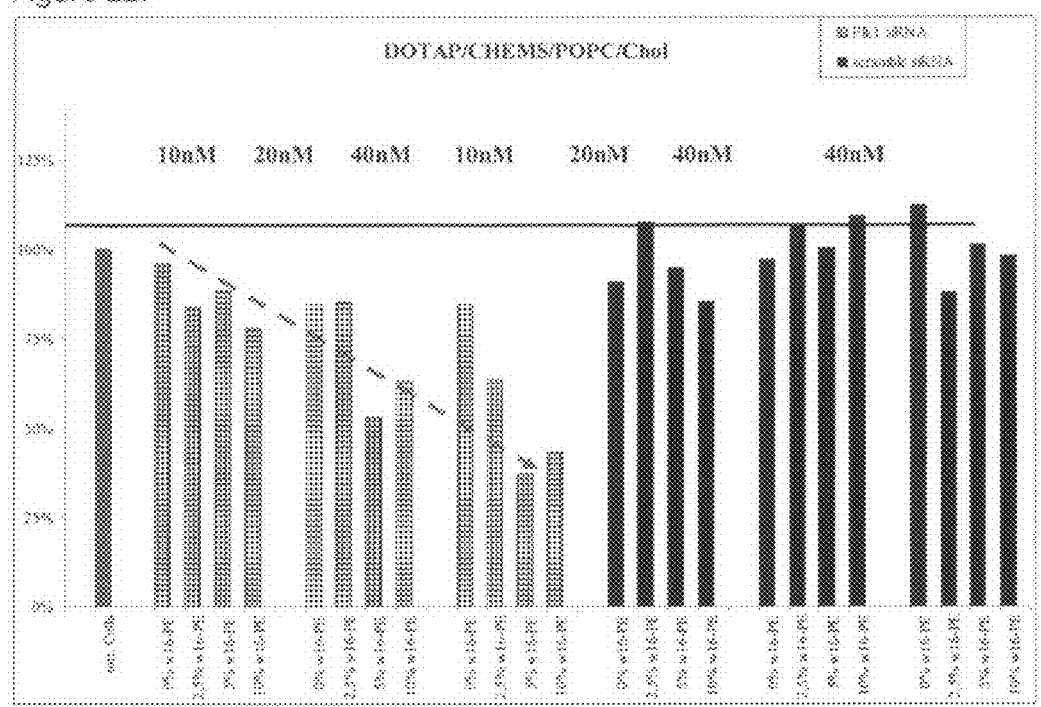

LIPIDS AND LIPID ASSEMBLIES COMPRISING TRANSFECTION ENHANCER ELEMENTS

CROSS-REFERENCE TO RELATED APPLICATIONS

This application is a continuation-in-part and claims the benefit of priority from European Patent Application No. 06256450.5, filed on Dec. 19, 2006, U.S. patent application Ser. No. 11/642,347, filed on Dec. 19, 2006 now abandoned, and European Patent Application No. 07117189.6, filed on Sep. 25, 2007. All patents, patent applications and references cited in this specification are hereby incorporated by reference in their entirety.

Each of the applications and patents cited in this text, as well as each document or reference cited in each of the applications and patents (including during the prosecution of each issued patent; "application cited documents"), and each of the U.S. and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in the practice of the invention.

FIELD OF THE INVENTION

The present invention relates to novel lipids comprising a lipid moiety and one or more structural elements that are capable of enhancing the fusogenicity of such lipids, or lipid assemblies (e.g. liposomes) incorporating such lipids, with biological membranes, in particular cell membranes. Such structural elements are pH sensitive in terms of charge and hydrophilicity and undergo a polar—apolar transition when exposed to low pH. The invention also comprehends the use of such structural elements by complexing the same with lipids by means of ionic interactions for improving the fusogenicity of such lipids.

BACKGROUND OF THE INVENTION

The fusion of membranes is a common event in biological systems and nature has developed elegant mechanisms for that. For example, the infection of a cell by a virus is one event in which fusion of membranes plays a key role.

It is therefore not surprising that the ability of viruses to promote fusion with cellular or endosomal membranes led to the development of recombinant viral gene delivery systems. The most prominent systems rely on retroviral-, adenoviral-, adeno-associated viral- or herpes simplex viral vectors, which are employed in more than 70% of clinical gene therapy trials worldwide. Although virus based gene delivery systems are very efficient, they show immune-related side effects after the injection. This major drawback limits the safety of these systems and consequently their applicability in humans (e.g., Thomas et al., Nature Reviews, Genetics, 4, 346-358, 2003).

An alternative is the use of non-viral vectors to deliver genetic material into cells. Nonviral vector systems include, for example, cationic polymers and liposomes. Liposomes are artificial single, oligo or multilamellar vesicles having an aqueous core and being formed from amphipathic molecules. The cargo may be trapped in the core of the liposome or disposed in the membrane layer or at the membrane surface. Today, liposomal vectors are the most important group of the nonviral delivery systems. More specifically, cationic liposomes or lipids have been used widely in animal trials and/or clinical studies. Although cationic systems provide high loading efficiencies, they lack colloidal stability, in particular after contact with body fluids. Ionic interactions with proteins and/or other biopolymers lead to in situ aggregate formation with the extracellular matrix or with cell surfaces. Cationic lipids have often been found to be toxic as shown by Filion, et al. in BBA, 1329(2), 345-356, 1997; Dass in J. Pharm. Pharmacol, 54(5), 593-601, 2002; Hirko, et al. in Curr. Med. Chem., 10(14), 1185-1193, 2003.

Amphoteric liposomes represent a recently described class of liposomes having an anionic or neutral charge at pH 7.5 and a cationic charge at pH 4. WO 02/066490, WO 02/066012 and WO-A-03/070735, all to Panzner, et al. and incorporated herein by reference, give a detailed description of amphoteric liposomes and suitable lipids therefor. Further disclosures are made in WO-A-03/070220 and WO-A-02/066489, also to Panzner, et al. and incorporated herein by reference, which describe further pH sensitive lipids for the manufacture of such amphoteric liposomes.

Amphoteric liposomes can encapsulate nucleic acid molecules with high efficiency equal to cationic liposomes. Advantageously, amphoteric liposomes are much better tolerated upon administration in vivo and show a favourable biodistribution over cationic liposomes.

Compared to viral gene delivery vectors the non-viral systems are much safer; they are tolerated at high doses and do not elicit an immune response, therefore these systems can be administered repetitively. Still, viral systems are superior in terms of transfection efficacy. Attempts have been made to incorporate viral surface glycoproteins into liposomes (Miller N, Vile R., FASEB J, 9, 190-199, 1995) but these hybrid systems again have the drawback of immune-related side effects.

There is therefore an ongoing need for improvements of non-viral systems.

It is known in the prior art that the pH sensitive hydrophilic moieties can be used for engrafting ligands or active ingredients to a liposomes. WO-A-86/04232 of Kung et al., for example, discloses liposome compositions containing coupling groups in their outer bilayer region to bind surface bound molecules such as proteins. The coupling reagents disclosed by Kung et al. include a phosphatidylethanolamine lipid moiety, a carbon containing spacer arm of up to 20 atoms and a terminal carboxyl group. The terminal carboxyl group is employed as a coupling group, and the hydrophobic moiety provides spatial separation between the lipid bilayer and said coupling group.

A related approach is disclosed in WO-A-97/19675 of Wheeler which relates to cationic lipids of a Rosenthal inhibitor (RI) core structure having an alkyl linking group with up to 10 carbon atoms, e.g., a carboxyalkyl group. RI structures with additional carboxyalkyl groups are disclosed as intermediates for further functionalisation, e.g., with ligands for cellular uptake, therapeutic molecules or groups that can increase the polar charge density of the cationic lipids.

U.S. Pat. No. 6,294,191 describes lipids comprising long hydrophobic moieties lacking a hydrophilic group ( ). These structures do not react to changes in pH.

WO-A-00/11007 of Tournier et al. discloses phosphatidic acid esters for stabilising liposome vesicles in suspension in water, buffers and biological liquids against rupture and coalescence with time. Such esters are also said to increase encapsulating capacity and stabilise the vesicle membrane against leakage of the entrapped substances toward the carrier liquid.

EP-A-0099068 to Eibl discloses glycerol derivatives.

Prior art is silent to the use and optimization of structural elements (II) or lipids (I) to enhance cellular uptake and cytosolic delivery of liposomes and sequestered active ingredient. Prior art has not taught, that the combination of hydrophobic moieties with the pH sensitive hydrophilic moieties provides criticality to such function.

SUMMARY OF THE INVENTION

It is therefore a general object of the present invention to provide an improved non-viral carrier system for the in vivo, in vitro or ex vivo delivery of active agents into cells, especially mammalian cells.

In particular it is an object of the invention to provide an improved non-viral carrier system for delivering nucleic acids (e.g., oligonucleotides and plasmids) and other active agents having therapeutic properties e.g. "biologics" into cells.

Another object of the invention is the provision of a non-viral carrier system that provides improved uptake of such active agents into cells.

A different object of the present invention is to improve the uptake of liposomes and other lipid-based carrier systems that encapsulate or sequester active agents into cells. Yet another object of the invention therefore is to provide a compound that can be incorporated into a lipid assembly such, for example, as a liposome, for improving the uptake of the lipid assembly into a cell.

In particular, it is an object of the present invention to provide a compound that can be incorporated into such a lipid assembly for improving the fusogenicity of the assembly with biological membranes, especially cell membranes.

Yet another object of the invention is to provide pharmaceutical compositions comprising liposomes with improved uptake into cells as carriers for the delivery of active agents or other ingredients.

Yet another object of the present invention is to provide improved pharmaceutical compositions for the treatment or prophylaxis of inflammatory, immune or autoimmune disorders and/or cancer of humans or non-human animals.

Yet another object of the present invention is to provide improved compositions and methods for the treatment of humans or non-human animals in which a pharmaceutical composition comprising an active agent is targeted to a specific organ or organs, tumours or sites of infection or inflammation.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and are encompassed by the following detailed description and claims.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which:

FIG. 22 shows the relative cell proliferation of Hela cells transfected with formulations L-54-L-61 encapsulating Plk1-siRNA or scrambled siRNA (10-40 nM siRNA).

DETAILED DESCRIPTION OF THE INVENTION

Figure 1:
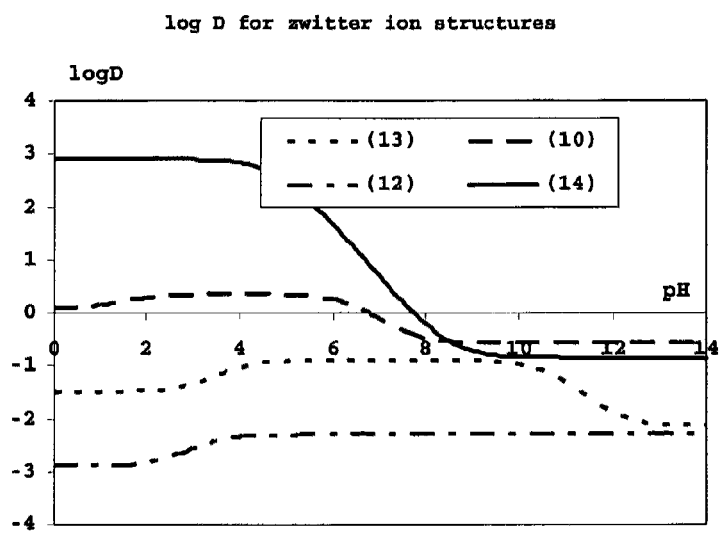
FIG. 1 shows the log D response of compound 10-14

According to one aspect of the present invention, therefore, there is provided a lipid comprising a lipid moiety and one or more transfection enhancer elements (TEE's) according to the general formula (I); wherein said one or more transfection enhancer elements (TEEs) have the general formula (II):

lipid-[hydrophobic moiety-pH sensitive hydrophilic moiety]     (I)

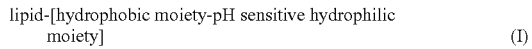

hydrophobic moiety-pH sensitive hydrophilic moiety     (II)

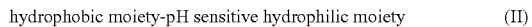

and wherein the pH sensitive hydrophilic moiety of each TEE is independently a weak acid having pKa of between 2 and 6 or a zwitterionic structure comprising combination of acidic groups with weak bases having a pKa of between 3 and 8; subject to the proviso that said lipid is not one of the following structures (III):

PE-amid linkage-X—COOH     (III)

wherein PE is a phosphatidylethanolamine moiety and X is a substituted or unsubstituted, saturated or unsaturated carbon-containing linear chain having a chain length of between 3 to 20 atoms, optionally comprising one or more heteroatoms;

(IV)

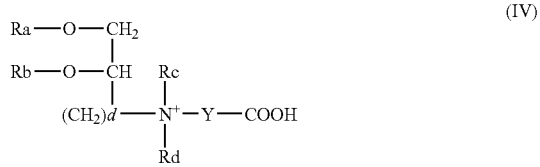

wherein Y is a saturated straight chain alkyl group having a chain length of between 2 and 10 C-atoms and Ra, Rb, Rc and Rd are independently linear or branched, unsubstituted or substituted $C_{1-23}$ alkyl, acyl, alkylene, heteroalkyl groups having 0 to 6 sites of unsaturation, cyclic or aryl groups, said groups comprising from 0 to 5 heteroatoms, in which the substituent groups are —O—$(CH_2)$e-$CH_3$; —S—$(CH_2)$e-$CH_3$; A-$(CH_2)$e, wherein A is a halide, and —N$((CH_2)$e-$CH_3)_2$, wherein the alkyl groups of the substituents comprise from 0-2 heteroatoms, and e is 0-4 and wherein Ra and Rb can further be independently H and d is 1 to 6; or (V)

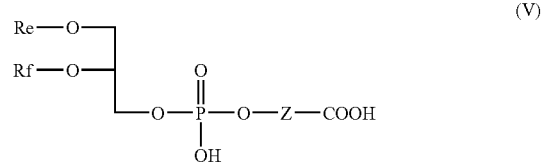

wherein Re and Rf are independently hydrogen atoms or $C_1$-$C_{24}$ straight chain or branched alkyl or acyl chains, optionally containing double and triple bonds, and Z is an aliphatic and/or cycloaliphatic hydrocarbon chain with 6-20 carbon-atoms, optionally substituted by aryl rings, cycloalkyls with 3-6 carbon atoms, hydroxyl and/or one or more further carboxylic groups.

The or each TEE moiety is thus incorporated in a lipid molecule. The position of the hydrophilic moiety within the or each lipid molecule may vary. In some aspects, the hydrophilic moiety may be located distally from the link between the lipid moiety and the TEE. Alternatively, the hydrophilic moiety may be located centrally within the TEE.

The present invention also comprehends, in a different aspect, the use of a transfection enhancer element (TEE) in a lipid assembly for improving the fusogenicity of the lipid assembly with a biological membrane, especially a cell membrane, wherein the transfection enhancer element (TEE) may be incorporated in a lipid molecule or may be complexed with the lipid assembly by means of ionic interactions, said TEE having the formula (II):

hydrophobic moiety-pH sensitive hydrophilic moiety     (II)

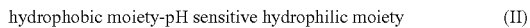

wherein the pH sensitive hydrophilic moiety of the TEE is a weak acid having pKa of between 2 and 6 or a zwitterionic structure comprising a combination of an acidic group with a weak base and having a pKa of between 3 and 8.

Where one or more transfection enhancer elements are incorporated in a lipid molecule, said molecule may have the formula (I):

lipid-[hydrophobic moiety-pH sensitive hydrophilic moiety].     (I)

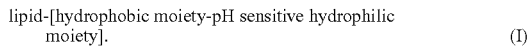

Thus, in another aspect of the present invention there is provided a lipid assembly including one or more lipids according to the invention or transfection enhancer elements (TEE's) that are complexed with said lipid assembly by means of ionic interactions, said TEE's having the formula:

hydrophobic moiety-pH sensitive hydrophilic moiety     (II)

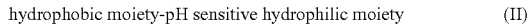

said pH sensitive hydrophilic moiety of each TEE being independently a weak acid having a pka of between 2 and 6 or a zwitterionic structure comprising a combination of acidic groups with weak bases having a pKa of between 3 and 8.

And in yet another aspect of the present invention, there is provided a lipid assembly formed from a lipid phase having amphoteric character, said assembly including lipids comprising one or more transfection enhancer elements (Lipid-TEE's) according to the formula (I), wherein said transfection enhancer elements (TEE's) have the general formula (II):

lipid moiety-[Hydrophobic moiety-pH sensitive hydrophilic moiety]     (I)

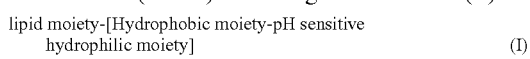

hydrophobic moiety-pH sensitive hydrophilic moiety     (II)

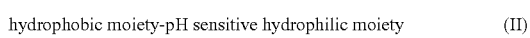

and said pH sensitive hydrophilic moiety of said TEE is a weak acid having a pka of between 2 and 6 or is a zwitterionic structure comprising a combination of an acidic group with a weak base having a pKa of between 3 and 8.

Said lipid assemblies may sequester active pharmaceutical ingredients. In one embodiment said pharmaceutical ingredients are nucleic acid-based drugs, like DNA plasmids, polynucleotides and oligonucleotides.

It has been found that lipid assemblies, in particular liposomes, comprising one or more lipids incorporating one or more transfection enhancer elements (TEE's) or being complexed with one or more separate transfection enhancer elements by means of ionic interactions may be used efficiently to transfect cells in vitro, in vivo or ex vivo.

The present invention provides an improvement in non-viral carrier systems for active pharmaceutical ingredients based on a hydrophile-hydrophobe transition in response to acidification of the environment. Such mechanism is also known in the nature. For example, influenza viruses use a specific fusion mechanism. After the virus is internalized into the cell by receptor-mediated endocytosis, the viral envelope fuses with the endosomal membrane which leads to a release of the viral genome into the cytosol of the infected cell. This fusion event is catalyzed by the viral envelope glycoprotein hemagglutinin. The trigger of the fusion is the acidic pH within the endosomal compartment leading to a conformational change of the hemagglutinin. Concomitantly, the N-terminal fusion peptide of the HA2 chain undergoes a hydrophobic shift due to protonation of carboxyl groups in the amino acid side chain. The hydrophobic peptide can insert into the target membrane which leads to destabilization and subsequent fusion (e.g., Stegmann et al., EMBO J., 9(13), 4231-4241, 1990).

In some embodiments the pH-responsive hydrophilic moiety of the TEE of the invention may comprise a weak acid having a pKa of between 3 and 5. Said weak acid may be selected from carboxyl groups, barbituric acid and derivatives thereof, xanthine and derivatives thereof.

In other embodiments, said pH-responsive hydrophilic moiety may be a zwitterionic structure comprising a combination of a weak or strong acidic group with a weak base, the latter having a pKa of between 4.5 and 7. Suitably said zwitterionic structure may be formed from an anionic group and a heterocyclic nitrogen atom as cationic group.

To achieve specific pKa's of said hydrophilic moieties, said pH-responsive hydrophilic moiety may be substituted with structural elements, selected from the group comprising hydroxymethyl-, hydroxyethyl-, methoxymethyl-, methoxyethyl-, ethoxymethyl-, ethoxyethyl-, thiomethyl-, thioethyl-, methylthiomethyl-, methylthioethyl-, ethylthiomethyl-, ethylthioethyl-, chlorid-, chlormethyl-vinyl-, phenyl-, benzyl-, methyl-, ethyl-, propyl-, isopropyl- and tert-butyl or cyclohexyl groups.

In some embodiments said hydrophobic moiety comprise linear, branched or cyclic chains with a minimum chain length of 6 elements. In one aspect of this embodiment said hydrophobic moiety comprises more than 6 and up to 40 elements, in a second aspect said hydrophobic moiety comprises between 6 and 20 elements and in a third aspect said hydrophobic moiety comprises between 20 and 40 elements.

The chain elements of said hydrophobic moiety may be carbon atoms. In one embodiment said hydrophobic moiety can be saturated or may contain unsaturated bonds. In other embodiments said hydrophobic moiety may be substituted.

In some embodiments the branching of the main chain of said hydrophobic moiety may comprise rather small building blocks. Preferred building blocks comprise methyl-, ethyl-, propyl-, isopropyl-, methoxy-, ethoxy-, methoxymethyl-, ethoxymethyl-, methoxyethyl-, ethoxyethyl- and vinyl- or halogen groups or mixtures thereof.

Alternatively, said hydrophobic moiety may derive from sterols, said sterols may be further substituted.

It is possible to insert one or more heteroatoms or chemical groups into the hydrophobic moiety of the pH-responsive transfection enhancer elements (TEE's). Such heteroatoms or chemical groups may be selected from —O—, —S—, —N(H)C(O)—, —C(O)O—, —OC(O)N(H)—, —C(O)—, —C(O)—N(H)—, —N(H)—C(O)—O—, —CH=N—, —O—C(O)—, —N=CH— and/or —S—S—, amino acids or derivatives thereof, α-hydroxyacids or β-hydroxy acids.

TEE's undergo a hydrophile-hydrophobe transition in response to an acidification of the environment. This transition is mediated by the hydrophilic moieties described above that are responsive towards pH.

In some embodiments of the invention log D(4.0)-log D(7.4)>=1 for the transfection enhancer elements and log D at pH 7.4 is between 1 and 10.

In most aspects of the invention, the log D at pH 4 of said pH-responsive transfection enhancer elements (TEE's) exceeds 0.

Of course, said pH-responsive transfection enhancer elements (TEE's) may contain more than one pH responsive hydrophilic moiety.

Where the transfection enhancer elements are chemically linked to a lipid moiety in accordance with the invention, the TEE's may be linked or grafted to the polar head group of said lipid moiety. In a further embodiment the lipids may include chemical linkers between the graft and the pH sensitive transfection enhancer elements. Furthermore the polar headgroup of the lipid moiety may be further substituted. In yet another embodiment of this aspect said lipids may contain more than one hydrophilic polar head group or complex hydrophilic head groups that allow substitution on various positions without affecting hydrophilicity.

The lipid assemblies of the present invention may be formed from a lipid phase further comprising neutral and/or cationic and/or anionic lipids and the overall charge of said lipid assemblies can be neutral, cationic or anionic.

In one aspect of the present invention the lipid assemblies are liposomes and in a specific embodiment of this aspect the liposomes are amphoteric liposomes of various size and lamellarity. Said amphoteric liposomes may be formed from a lipid phase comprising one or more amphoteric lipids or from a lipid phase comprising (i) a stable cationic lipid and a chargeable anionic lipid, (ii) a chargeable cationic lipid and chargeable anionic lipid or (iii) a stable anionic lipid and a chargeable cationic lipid.

Where said TEE's are complexed with said lipid assemblies using ionic interactions in accordance with the invention. said TEE's may be linked to a polycationic element and combined with anionic lipid assemblies or linked to a polyanionic element and combined with cationic lipid assemblies.

The lipid assemblies of the present invention may be sequester active pharmaceutical ingredients and in a specific embodiment said pharmaceutical ingredients are nucleic acid-based drugs, like oligonucleotides, polynucleotides or DNA plasmids.

In a preferred embodiment of the invention said lipids are selected from the group comprising compounds (30) to (69) below.

In yet another aspect of the present invention there is provided a pharmaceutical composition comprising active agent-sequestered lipid assemblies or amphoteric liposomes in accordance with the present invention and a pharmaceutically acceptable vehicle therefor.

In yet another aspect, the present invention comprehends the use of a pharmaceutical composition according to the present invention for the treatment or prophylaxis of inflammatory, immune or autoimmune disorders and/or cancer of humans or non-human animals.

For clarity, the following definitions and understandings are used for important terms of the invention:

Transfection

... is used widely to specifically describe the disappearance of a concentration gradient across a biological membrane. It comprises transport across, or diffusion through, penetration or permeation of biological membranes irrespective of the actual mechanism by which said processes occur.

Log P

... is the ratio of the respective concentrations of a compound in the 1-octanol and water partitions of a two-phase system at equilibrium. The octanol-water partition coefficient (log P) is used to describe the lipophilic or hydrophobic properties of a compound.

Log D

... is the ratio of the equilibrium concentrations of all species (unionized and ionized) of a molecule in 1-octanol to same species in the water phase.

The partition coefficient for dissociative mixtures, log D, is defined as follows:

$$\log D = \log(\Sigma(c_i^{H2O})/\Sigma(c_i^{org})), \text{ where}$$

$c_i^{H2O}$ is the concentration of the i-th microspecies in water and $c_i^{org}$ is the concentration of the i-th microspecies in the organic phase.

Log D differs from log P in that ionized species are considered as well as the neutral form of the molecule. Log D is therefore the log P at a given pH of the medium. Log D at pH 7.4 is often quoted to give an indication of the lipophilicity of a drug at the pH of blood plasma.

Log P and log D values can be determined experimentally by measuring the partition of a molecule or its ionized forms in octanol/water systems. Experimental values have been generated for a vast amount of individual compounds and expert systems allow extrapolating log P and log D values for novel species. One such expert system is ACD/Labs with the modules ACD/Log P or ACD/log D and ACD/Labs 7.06 has been used for calculations within this disclosure.

"Nucleic Acid" or "Polynucleotide"

... as used herein refers to any nucleic acid containing molecule, including without limitation, DNA or RNA. The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

Oligonucleotide

... as used herein is defined as a molecule with two or more deoxyribonucleotides or ribonucleotides, often more than three, and usually more than ten. The exact size of an oligonucleotide will depend on many factors, including the ultimate function or use of the oligonucleotide. Oligonucleotides can be prepared by any suitable method, including, for example, cloning and restriction of appropriate sequences and direct chemical synthesis by a method such as the phosphotriester method of Narang et al., Meth. Enzymol., 68, 90-99, 1979; the phosphodiester method of Brown et al., Method Enzymol., 68, 109-151, 1979 the diethylphosphoramidite method of Beaucage et al., Tetrahedron Lett., 22, 1859-1862, 1981 the triester method of Matteucci et al., J. Am. Chem. Soc., 103, 3185-3191, 1981 or automated synthesis methods; and the solid support method of U.S. Pat. No. 4,458,066.

Lipid Assemblies

... are supramolecular assemblies comprising amphipathic molecules. In some aspects the amphipathic substances are known as lipids or as detergents, in other aspects such substances are known to form biological membranes or to insert into biological membranes. The supramolecular assemblies may further comprise oils from apolar molecules. The supramolecular assemblies of the current invention therefore comprise liposomes of various size and lamellarity, micelles, inverted micelles, cubic or hexagonal lipid phases, cochleates, emulsions, double emulsions or other multimeric assemblies that are substantially build from lipids, oils or amphiphiles.

As described above it was found that lipid assemblies comprising one or more lipids with one or more transfection enhancer elements may be used to efficiently transfect cells. Mechanistically, the pH sensitive hydrophilic moieties of the TEE become protonated at acidic pH. This in turn leads to a decrease of the polarity of the functional group. It is possible, that the lipids (I) or parts thereof, e.g. the TEE in its entirety or fractions thereof can insert into lipid bilayers provided in trans, thereby promoting fusion events. It is also possible that the structural element (II) upon acidification inserts into its own lipid bilayer, thereby creating structural defects that improve fusogenicity and cellular transfection.

Liposomal delivery of drugs (e.g. nucleic acids) into the cytoplasm of cells very often needs a successful escape from the endosomes, which have an acidic pH. So, within the scope of the present invention such lipids with structural element (II) may enable or improve the transfection ability of liposomes, irrespective of their charge.

Although a number of explanations can be given to explain the findings of the invention, an understanding of the exact mechanism whereby the enhanced fusion or transfection is achieved is not necessary for practicing the invention and even other mechanisms, not described here, may be involved.

Hydrophilic Moieties of TEE's

In one aspect of this invention the hydrophilic moieties are weak acids that provide a response in hydrophilicity between pH values of about 4 and the physiological pH of 7.4.

Carboxyl groups, barbituric acid or derivatives thereof, in particular xanthine or derivatives thereof of formula (1) to (3) in table 1a represent, but do not limit such pH-responsive hydrophilic moieties.

TABLE 1a

Compounds 1-3

| (1) | R—C(=O)—OH | (1) Carboxylic acids. R represents the hydrophobic moiety of the invention. |
|---|---|---|
| (2) | Barbituric acid structure with Ro, Rn, Rm substituents | (2) Barbituric acid derivatives. $R_m$, $R_n$ or $R_o$ may represent the hydrophobic moiety of the invention. |
| (3) | Xanthine structure with Rm, Rn substituents | (3) Xanthine derivatives. $R_m$ or $R_n$ represent the hydrophobic moiety of the invention. |

Log D values for hydrophilic head groups derived from (1) to (3) are high at low pH and low at neutral or higher pH.

Other derivatives of xanthins, pyrimidins (uracils) or barbituric acids are disclosed below in table 1b and analyzed with respect to their log D values at pH 4.0 and pH 7.4. The methoxyethyl moiety in compounds (100) to (129) represents or may be replaced by the hydrophobic moieties of the TEE as described above.

TABLE 1b

| Chemical structure | Compound-# | logD (pH 4) | logD (pH 7.4) |
|---|---|---|---|
| (structure) | (100) | −0.11 | −1.03 |
| (structure) | (101) | −0.39 | −2.18 |
| (structure) | (102) | 0.08 | −1.71 |
| (structure) | (103) | −0.85 | −2.13 |
| (structure) | (104) | −0.27 | −0.62 |

TABLE 1b-continued

| Compounds 100-129 | | | |
|---|---|---|---|
| Chemical structure | Compound-# | logD (pH 4) | logD (pH 7.4) |
| | (105) | −0.18 | −0.77 |
| | (106) | −2.76 | −3.44 |
| | (107) | −0.1 | −1.88 |
| | (108) | −0.93 | −1.27 |
| | (109) | −2.01 | −3.43 |

TABLE 1b-continued

| Compounds 100-129 | | | |
|---|---|---|---|
| Chemical structure | Compound-# | logD (pH 4) | logD (pH 7.4) |
| | (110) | −1.34 | −2.16 |
| | (111) | 0.92 | −1.31 |
| | (112) | −1.34 | −3.15 |
| | (113) | −0.39 | −1.69 |
| | (114) | 0.21 | −1.51 |

TABLE 1b-continued

Compounds 100-129

| Chemical structure | Compound-# | logD (pH 4) | logD (pH 7.4) |
| --- | --- | --- | --- |
| 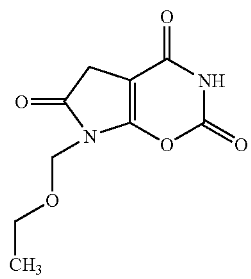 | (115) | 0.22 | −0.27 |
| 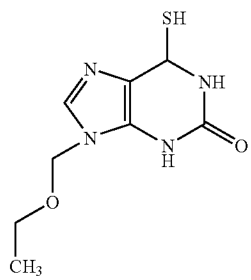 | (116) | −0.33 | −0.74 |
| 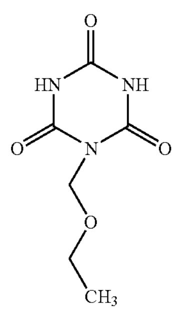 | (117) | −2.07 | −3.44 |
| 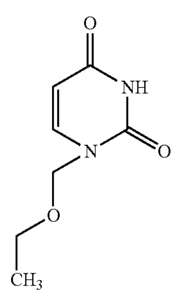 | (118) | −0.65 | −0.68 |
| 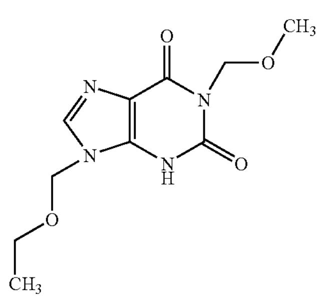 | (119) | −0.76 | −2.42 |

TABLE 1b-continued

Compounds 100-129

| Chemical structure | Compound-# | logD (pH 4) | logD (pH 7.4) |
|---|---|---|---|
| 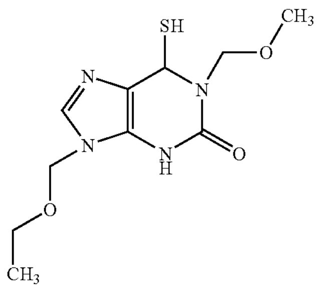 | (120) | −0.31 | −1.07 |
| 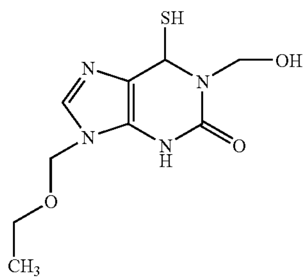 | (121) | −0.62 | −1.38 |
| 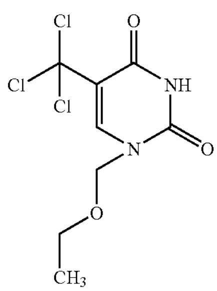 | (122) | 1.65 | 0.71 |
| 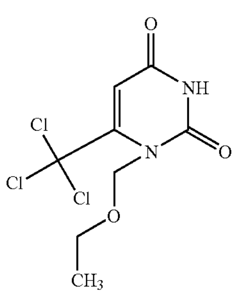 | (123) | 1.87 | 0.41 |
| 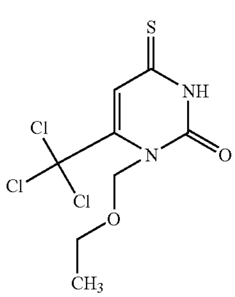 | (124) | 3.25 | 1.46 |

TABLE 1b-continued
Compounds 100-129
| Chemical structure | Compound-# | logD (pH 4) | logD (pH 7.4) |
|---|---|---|---|
| 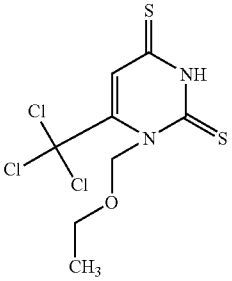 | (125) | 2.81 | 1.15 |
| 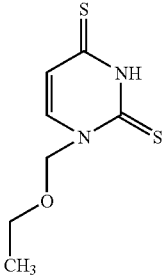 | (126) | 0.56 | −1.25 |
| 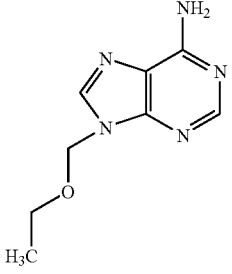 | (127) | −0.59 | −0.23 |
| 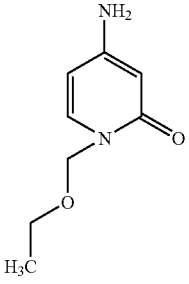 | (128) | −1.21 | −0.98 |
| 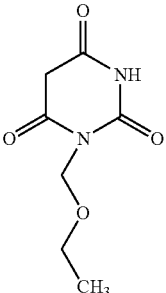 | (129) | −0.48 | −3.23 |

In another aspect of the invention, the hydrophilic moieties comprise zwitterionic groups that respond to changes in the pH of the environment. Zwitterionic structures exist at pH values where both the cationic and the anionic group are charged and a generalized log D plot is shown in FIG. 1. It is apparent that the zwitterions have higher log D values than the charged parent groups.

The desired increase in log D upon acidification is represented by the right flank of the log D curve and depends on the pKa of the cationic charge group; it is rather independent from the pKa of the anionic group itself. As an example, the anionic group maybe a carboxyl group and the cationic group maybe a heterocyclic nitrogen atom two to five carbon atoms apart from that group (e.g. compounds 10 or 11). Pyridylcarboxylic acids, imidazolcarboxylic acids or the like are a few representations of such pH-responsive hydrophilic moieties. The zwitterion exists between pH 4 and pH 7, thereby providing the pH-responsive hydrophilic headgroups of the invention. On the contrary, a simple amino group having a high pKa of about 9 (e.g. compound 13) or a quarternary ammonium group providing a constant positive charge with no effective pKa (e.g. compound 12) extends the range of pH values where the zwitterion exists and any change in hydrophilicity does no longer occur in the pH region desired (pH 2 to 9 or the more preferred ranges given above) (see FIG. 1 and table 2).

TABLE 2

Compounds 10-14

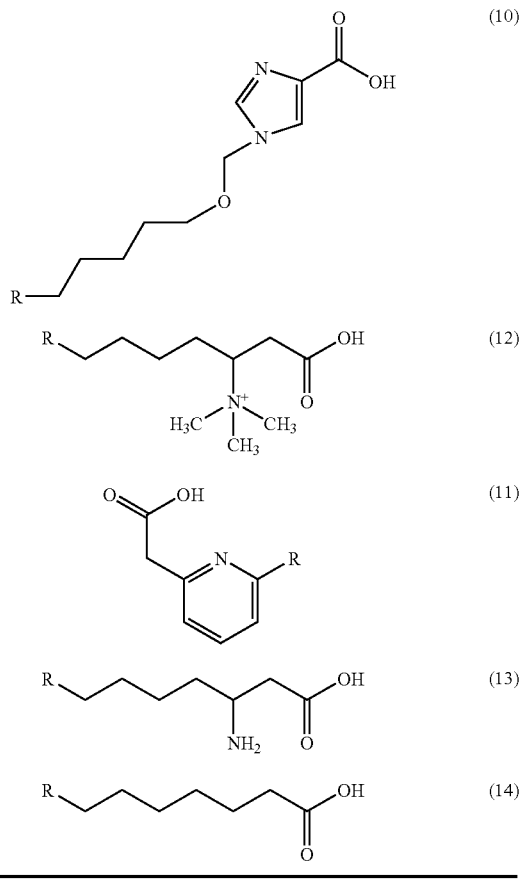

The hydrophilic moieties can further be substituted with polar or apolar groups. In one aspect of the invention, substitutions are selected to achieve a specific pKa of the hydrophilic moiety. Rules to achieve such adjustment of pKa values are known to the skilled artisan and comprise for example substitutions at nitrogen atoms of barbituric acid or xanthine with hydroxymethyl-, hydroxyethyl-, methoxymethyl-, methoxyethyl-, ethoxymethyl-, ethoxyethyl-, thiomethyl-, thioethyl-, methylthiomethyl-, methylthioethyl-, ethylthiomethyl-, ethylthioethyl-, chloro-, chloromethylvinyl-, phenyl- or benzyl groups or mixtures thereof to achieve a lower pK of the structure. Substitutions at the positions $R_m$, $R_n$ or $R_o$ in formula (2) or (3) are in particular suitable to achieve such shift in pK values.

Of course, pK values can be shifted towards higher values with substitutents comprising methyl-, ethyl-, propyl-, iso-propyl- and tert-butyl or cyclohexyl groups or mixtures thereof.

An excellent overview for substituted xanthins and their respective pK values is found in Kulikowska et al., Biochim. Acta Pol., 51, 493-531, 2004.

It is known, that the pKa value for carboxyl groups is also affected by substitutions or chemical alterations in spatial proximity. Acrylic acid derivatives, aromatic carboxylic acids such as benzoic acid, pyridinyl carboxylic acid, α- or β-hydroxycarboxylic acids or α- or β-thiocarboxylic acids but also halogenated carboxylic acids have lower pKa values than the parent compounds. In contrast, substitutions with an +I effect change the pKa of a carboxyl group towards higher values, e.g. in cyclohexylcarboxylic acids.

Specific examples of substituted hydrophilic moieties include, but are not limited to formula (4) to (9) of table 3, wherein R identifies the hydrophobic moiety of the TEE:

TABLE 3

Compounds 4-9

Substituted xanthines

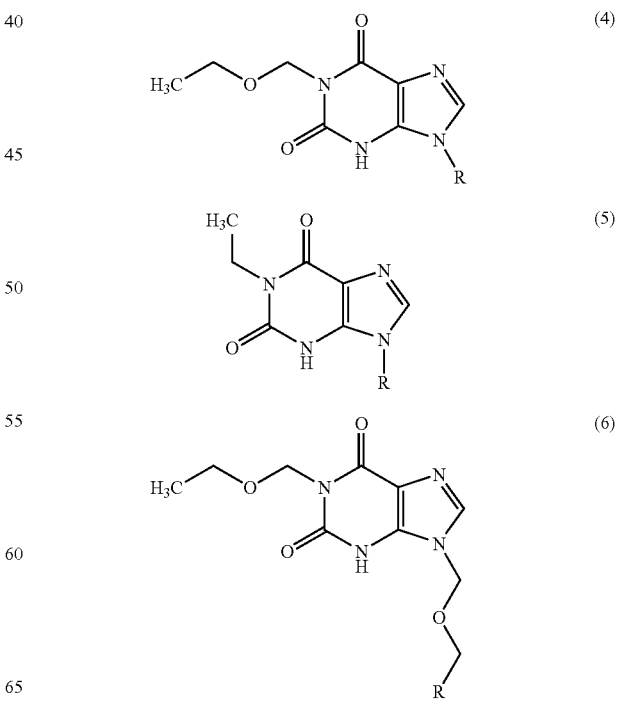

TABLE 3-continued

Compounds 4-9

Substituted carboxylic acids

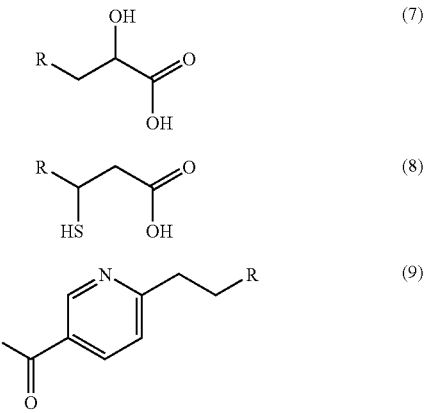

Further chemical representations for the hydrophilic moieties can be identified from the group of weak acids using the relationship between log D, pH and the pKa of the substance. For acids, this can be expressed as follows:

$$\log D = \log P + \log(1+10^{(pH-pKa)});$$

wherein log P is the partition coefficient for the non-ionized form. The equation reflects conditions of zero ionic strength and extremely low values for log D are calculated for acids at high pH. Under physiological conditions, where the ionic strength is about 0.15M, salt formation is limiting such extremes in log D.

Figure 2:
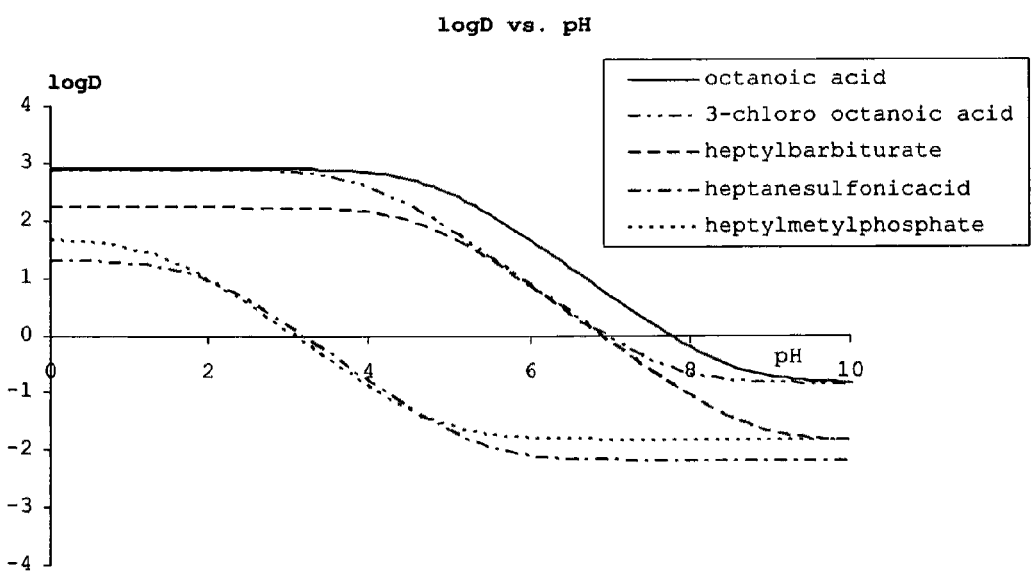
FIG. 2 shows the relation between log D and pH for different hydrophiles in TEE structures. All hydrophilic moieties are located at the terminal position of the alkyl chain. Log D starts to decrease at pH values roughly equal to pKa, such decrease being limited by ion pair formation at physiological ionic strength.

FIG. 2 shows the log D calculations for a number of hydrophilic moieties.

Figure 3:
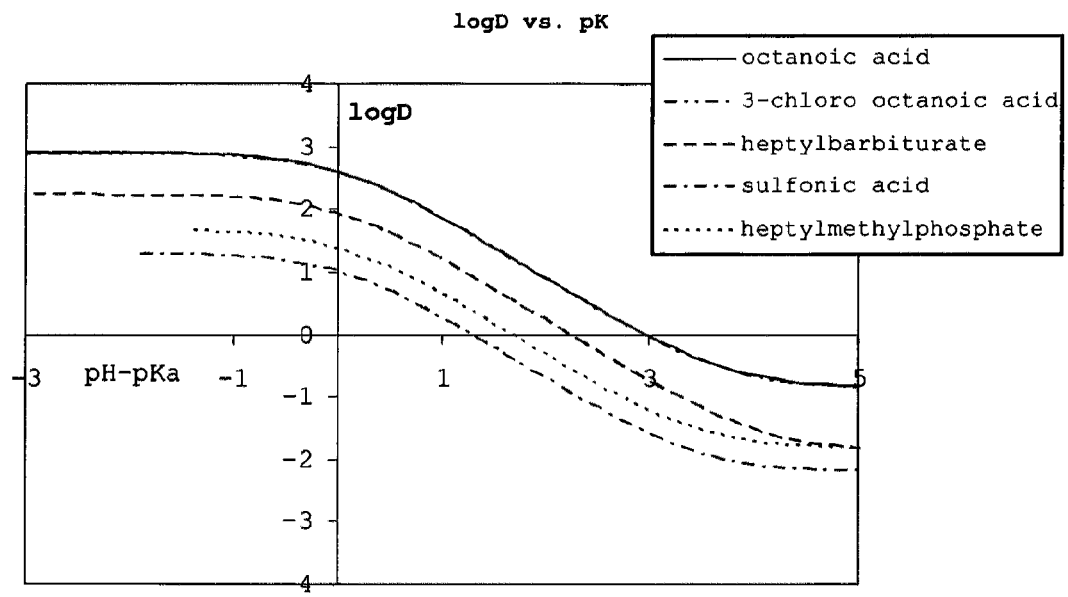
FIG. 3 shows standardized curves for log D wherein pH-pKa is used as x-axis for different hydrophiles in TEE structures. All hydrophilic moieties are located at the terminal position of the alkyl chain. 3-chloro octanoic acid is identical with octanoic acid and not shown in the plot.

Further analysis reveals identical shifts in log D when curves are plotted against pH-pKa (see FIG. 3).

Once standardized with respect to their pKa values the log D plots become similar for all hydrophilic moieties analyzed here. A maximum difference of 3.75 units in log D can be achieved for the ionization of a single hydrophilic moiety. The maximum amplitude for zwitterion formation is about 2.5 units in log D.

Figure 4:
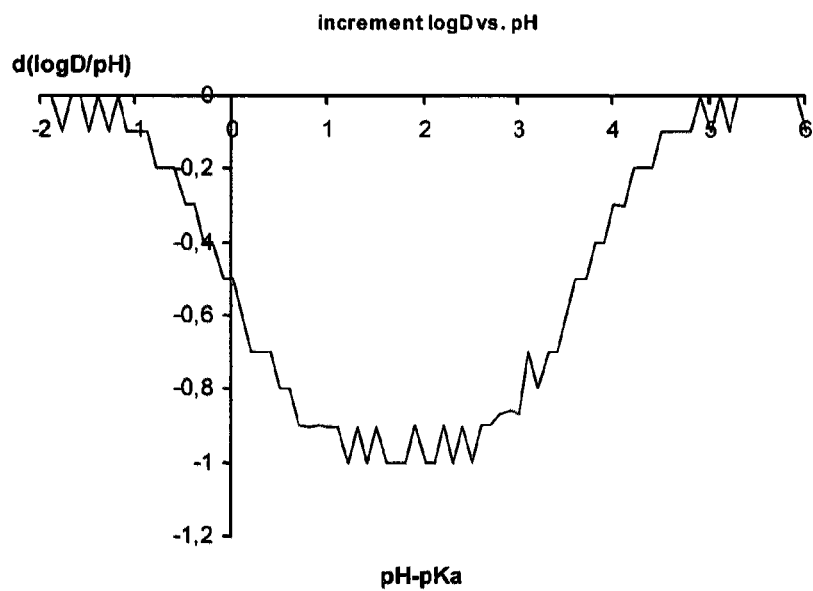
FIG. 4 shows an analysis of the increment of log D vs. pH. The curve was standardized using pH-pKa as a common descriptor that is independent from the pKa of the individual hydrophilic moieties.

The full amplitude requires a rather large shift of about 6 units in pH. Within the practical range of ΔpH~3.4 (pH 7.4-pH 4) considered for many aspects of this invention, the maximum difference in log D is about 3 units for pKa ~4. The log D reacts very sensitive whenever the pH is 0 to 4 units above the pKa, the most sensitive reaction is at pH values between 1 and 2.5 units above pKa. This relation is also analyzed in the FIG. 4.

In practical terms, the ideal pKa for hydrophilic moieties is about 4. Preferred are hydrophilic moieties having a pKa between 2 and 6 (maximum amplitude about 1.5 units), more preferred are hydrophilic moieties having a pKa between 3 and 5 (maximum amplitude about 2.5 units). Other hydrophilic moieties within the scope of the invention may have pKa values between 1 and 7.

Hydrophobic Moieties of the TEE's

TEE's of this invention comprise hydrophobic moieties which contribute to the penetration of biological lipid membranes. Chemical representations of such hydrophobic moieties include linear, branched or cyclic chains with a minimum chain length of 6 elements. In many aspects of the invention the chain elements are carbon atoms. In some aspects of the invention the chain elements may comprise heteroatoms being able to form covalent bonds with more than one other chain element. Hydrogen or halogen atoms can substitute the chain, but are not elements of the chain. The hydrophobic moieties can comprise more than 6 elements and may comprise up to 40 elements. In some aspects of the invention the hydrophobic moieties comprise between 6 and 12 elements. In other aspects of the invention the hydrophobic moiety comprise between 12 and 20 elements. In still other aspects of the invention the hydrophobic moiety does comprise between 20 and 40 elements.

In one aspect, the branching of the main chain comprises one or more rather small building blocks such as methyl-, ethyl-, propyl-, isopropyl-, methoxy-, ethoxy-, methoxymethyl-, ethoxymethyl-, methoxyethyl-, ethoxyethyl- and vinyl- or halogen groups or mixtures thereof.

Hydrophobic moieties can be saturated or may contain unsaturated bonds.

In another aspect, more complex branched and or cyclic ring systems may be chemical representations of the hydrophobic moiety. In one embodiment of such aspect, hydrophobic moieties are derived from sterols. Of course, the sterols may further be substituted with methyl-, ethyl-, propyl-, isopropyl-, methoxy-, ethoxy-, methoxymethyl-, ethoxymethyl-, methoxyethyl-, ethoxyethyl- and vinyl- or halogen groups or mixtures thereof. In another aspect of the invention, the hydrophobic moieties may comprise sterols that are substituted with one or more hydrophilic groups such as hydroxyl groups. In a preferred embodiment, sterols contain hydroxyl groups at one or more of the positions 3, 7 and 12. In a preferred aspect, the sterol is a cholestane and in a further preferred embodiment the cholestane is hydroxylated in one or more of the positions 3, 7 or 12.

It is possible to insert one or more heteroatoms or chemical groups into the hydrophobic moiety. In one embodiment of the invention the hydrophobic moiety does comprise no more than 5 and in another embodiment no more than 2 heteroatoms or chemical groups.

The heteroatoms or chemical groups may be selected from the group comprising —O—, —S—, —N(H)C(O)—, —C(O)O—, —OC(O)N(H)—, —C(O)—, —C(O)—N(H)—, —N(H)—C(O)—O—, —CH=N—, —O—C(O)—, —N=CH— and/or —S—S—.

In some aspects, said heteroatoms and/or chemical groups derive from amino acids, α-hydroxyacids or β-hydroxy acids.

In one embodiment said amino acid building block is selected from the group of proline, glycine, alanine, leucine, isoleucine, valine, tyrosine, tryptophane, phenylalanine or methionine or peptides thereof and said α- and β-hydroxyacids are selected from the group comprising glycolic acid, lactic acid or hydroxybutyric acid.

In another embodiment of such an aspect, more than a single ether group is present and the spacing between the ether bonds is two carbon atoms, representing the monomer elements in poly-ethylenglycol or poly-propylenglycol.

Architecture of TEE's

Construction of TEE's is governed by its physicochemical parameters; TEE's undergo a hydrophile-hydrophobe transition in response to an acidification of the environment. This transition is mediated by the hydrophilic moieties described above that are responsive towards pH. Such response should have minimum amplitude of 0.5 log D whereby the higher absolute value of log D is achieved at the lower pH. In one aspect, such amplitude is higher than 1 log D which means that a distribution of such TEE from the water phase to the hydrophobic interior of the membrane becomes 10 times more preferred. In another aspect, such amplitude is higher than 1.5 and in some aspects the amplitude between the hydrophilic and hydrophobic form is more than 2 log D units.

In one aspect of the invention, the hydrophilic moieties respond to pH values between the physiological pH and slightly acidic conditions of about pH 4. Such slightly acidic conditions can be found within cell organelles like endosomes or lysosomes. Therefore TEEs may be capable of mediating the endosomal escape of lipid aggregates or liposomes after endocytotic uptake into the cell. Tumor tissue or areas of ongoing inflammation also provide a slightly acidic environment and consequently TEEs may be useful to accumulate lipid aggregates or liposomes in these areas. Accumulation may occur specifically in tumor or stroma cells or in cells of the immune system or fibroblasts that are present in inflammatory regions.

As described above, the governing pKa for the shift in hydrophilicity can be the pKa of a weak acidic group such as carboxylic acids, barbituric acids or xanthines. In a preferred embodiment the pK of the TEE essentially driven by weak acids can be optimized to maximize the difference between hydrophilicity at pH 7.4 and hydrophobicity at pH 4. In preferred aspects, the pKa of such hydrophilic moieties is between 2 and 6. In more preferred aspects this pKa is between 3 and 5.

In cases where a shift in hydrophilicity is caused by zwitterion formation, the governing pKa is the pKa of a weak base such as pyridine, imidazole, morpholine or piperazine. For zwitterions, base pKa are between 3 and 8, preferred between 4.5 and 7 and more preferred between 5 and 6.5.

TEE's may contain one or more hydrophilic moieties and the relative and absolute positioning of the hydrophilic moieties may vary. In some cases, neighbouring effects may occur. Effects within the hydrophilic groups include, amongst others, pK shifts and zwitterion formation. Effects between hydrophilic groups may also include shifts in the respective pK values. This is known to the skilled artisan and frequently observed between carboxylic acids in close proximity, e.g. when the spacing between groups is between 2 to 5 carbon atoms.

Some examples for more complex hydrophilic moieties are shown below (table 4).

TABLE 4

| Compounds 15 and 16 | |
|---|---|
| (15) ![structure] | (15) β-Glutamic acid derivatives. R represents the hydrophobic moiety of the invention. The ether bond between R and the hydrophilic moiety is optional and lowers the pK of the amino group. |
| (16) ![structure] | (16) 3-Amino-3-(methylthio)-propanoic acid derivatives R represents the hydrophobic moiety of the invention. Again, the ether bond between R and the amino group is optional but shifts the pK downwards and the same holds true for the thioether. The hydrophobic moiety may also be bound other positions including the methyl group at the thioether. |

TEE's with more than one hydrophilic moiety have larger amplitudes of hydrophilicity between their neutral and slightly acidic state. Of course, mixtures of hydrophilic moieties can be combined with a single hydrophobic moiety. Such mixture may allow more precise adjustments in the amplitude and pH-sensitivity of the hydrophobic shift. However, too large of a number of hydrophilic moieties increases the hydrophilicity of the TEE to values that can no longer be compensated with the hydrophobic shift.

Therefore, besides the amplitude of hydrophilicity between different pH values, the absolute hydrophilicity of the TEE at a first pH represents a very important aspect of the invention.

In terms of absolute hydrophilicity, the log D of the TEE itself may be vary between slightly hydrophilic at conditions of neutral or physiological pH and somewhat hydrophobic. In other words the TEE's have a log D at pH 7.4 between −2 and 10.

In preferred aspects, the log D (7.4) is greater than 1 and in some aspects the log D(7.4) is greater than 3. In other aspects of the invention, the log D(7.4) of the TEE is smaller than 10, in some aspects the log D(7.4) is smaller than 7.

Independent from its absolute log D at pH 7.4, the log D of the TEE at pH4.0 needs to exceed 0.

TEE's with a negative log D(7.4) require high amplitudes of the hydrophobic shift and such high amplitudes can be provided hydrophilic moieties comprising one or more carboxyl groups, xanthine groups or barbituric acid groups.

In one embodiment of the invention the TEE has one of the following general formula:

(VI)

wherein any Rep from $Rep_i$ is independently a non-branched, branched or cyclic, substituted or unsubstituted alkyl, alkenyl, alkylene, alkynyl or a aryl group with 1 to 8 C-atoms and wherein said substituents are selected from one or more pH sensitive hydrophilic moieties, lower alkyl, alkylene, alkenyl, alkynyl, alkoxy, alkoxyalkyl, alkylthio or alkylthioalkyl and wherein "lower" means 1-6 atoms and wherein any L from $L_j$, $L_k$ or $L_l$ is independently absent or independently selected from the group comprising —CH$_2$—, —O—, —S—, —N(H)C(O)—, —C(O)O—, —OC(O)N(H)—, —C(O)—, —C(O)N(H)—, —N(H)C(O)O—, —CH=N—, —OC(O)—, —N=CH— —S—S—, —NH—, —N($R_{13}$)($R_{14}$)— with $R_{13}$ and $R_{14}$ are independently H or $C_1$-$C_6$ alkyl or one of $R_{13}$ or $R_{14}$ may be absent; or

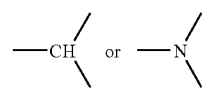

or amino acid, α-hydroxyacid or β-hydroxy acid.
and wherein the total amount of C-atoms in the TEE is 6-40 and $p$ is $\leq 40$ or -Sterol                                           (VII)

wherein said sterol may be substituted with one or more hydrophilic moieties,

—OH, —SH or lower alkyl, alkylene, alkenyl or alkynyl, alkoxy, alkoxyalkyl, alkyltio or alkylthioalkyl and wherein "lower" means 1-6 atoms In one aspect of this embodiment the amino acid in general formula VI is selected from the group of proline, glycine, alanine, leucine, isoleucine, valine, tyrosine, tryptophane, phenylalanine or methionine or peptides thereof and the α- and β-hydroxyacids in general formula VI are selected from the group comprising glycolic acid, lactic acid or hydroxybutyric acid.

Preferably the pH sensitive hydrophilic moiety is a weak acid of one of the following general formula having a pKa of between 1 and 7, preferred between 2 and 6 and more preferred between 3 and 5:

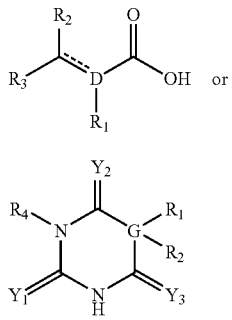

(VIII)

or (IX)

wherein the dotted line represents a double bond which is optional and $R_1$, $R_2$, $R_3$ and $R_4$ are independently the hydrophobic moiety of the TEE, hydrogen, linear, branched or cyclic, unsubstituted or substituted $C_1$-$C_{10}$ alkyl, alkylene or heteroalkyl having 0-5 sites of unsaturation, or aryl group and said groups comprising 0-5 heteroatoms, selected from —O— or —S—, wherein said heteroatoms are not the first atom in said groups and wherein said substituents are selected from hydroxy-, mercapto, oxo-, formyl-, nitro-, cyano-, halo- or a trihalomethyl group and wherein $R_1$, $R_2$, and $R_3$ may be alternatively and independently alkoxy-, alkoxyalkyl-, alkylthio-, alkylthioalkyl-, hydroxy-, mercapto-, oxo-, formyl-, nitro-, cyano-, halo- or a trihalomethyl group and D is C or an unsubstituted or substituted cyclic alkyl or aryl group having 0-3 sites of unsaturation and comprising 0-5 heteroatoms selected from —O—, —S—, and said substituents are selected from alkyl-, alkylene-, alkenyl-, alkynyl-, alkoxy-, alkoxyalkyl-, alkylthio-, alkylthioalkyl-, hydroxy-, mercapto-, oxo-, formyl-, cyano-, halo- or a trihalomethyl group and wherein $Y_1$, $Y_2$ and $Y_3$ are independently O or S and G may be C or N and when G is N one of $R_1$ or $R_2$ may be absent and $R_1$ and $R_2$ are defined as $R_4$ or

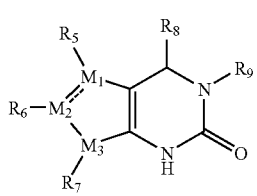

(X)

wherein the dotted line represents a double bond which is optional, $R_5$, $R_6$, $R_7$ or $R_9$ may be independently the hydrophobic moiety of the TEE, hydrogen, linear, branched or cyclic, unsubstituted or substituted $C_1$-$C_{10}$ alkyl, alkylene or heteroalkyl having 0-5 sites of unsaturation, or aryl group and said groups comprising 0-5 heteroatoms, selected from —O— or —S—, wherein said heteroatoms are not the first atom in said groups and wherein said substituents are selected from hydroxy-, mercapto-, oxo-, formyl-, nitro-, cyano-, halo- or a trihalomethyl group and wherein $R_8$ is O or SH and $M_3$ is N or C $M_2$ is C or —O— and if $M_2$ is —O—$R_6$ is absent $M_1$ is N or C or —O— and if $M_1$ is —O—$R_5$ is absent when $M_1$, $M_2$ or $M_3$ is C; $R_5$, $R_6$ or $R_7$ may further be alkoxy-, alkoxyalkyl-, alkylthio-, alkylthioalkyl-, hydroxy-, mercapto-, oxo-, formyl-, nitro-, cyano-, halo- or a trihalomethyl group and a further substituent $R_5'$, $R_6'$ or $R_7'$ defined as $R_5$, $R_6$ or $R_7$ may be attached to the C atom or

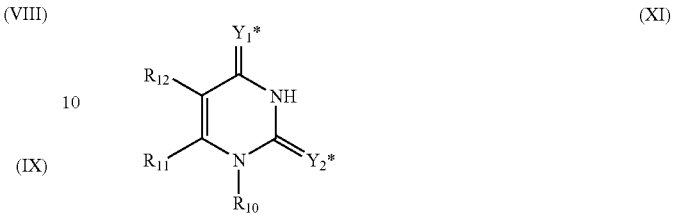

(XI)

wherein $R_{10}$ may be the hydrophobic moiety of the TEE and $R_{11}$ and $R_{12}$ may be independently hydrogen, hydroxy-, mercapto-, formyl-, nitro-, cyano- or halo- or a trihalomethyl group whereas at least one of $R_{11}$ and $R_{12}$ is other than H $Y_1^*$ and $Y_2^*$ are independently O or S Alternatively said pH sensitive hydrophilic moiety of the TEE forms a zwitterion upon acidification, wherein the cationic charge of said zwitterion is preferably a nitrogen atom of a weak base having a pka of between 3 and 8, preferred between 4.5 and 7 and more preferred between 5 and 6.5. In one aspect said weak base is imidazole, morpholine, pyridine or piperazine. Alternatively, said weak base is a non-cyclic amine.

It is known in the art that the pKa of such weak bases can be affected by heteroatoms in β- or γ-position of the nitrogen atom or by substitutions in spatial proximity, for example in α- or β-position of the nitrogen atom. Preferred heteroatoms are —O— or —S—. Substituents with an −I effect are capable for lowering the pKa of such weak bases and include without limitation alkoxy, alkylthio, hydroxy-, mercapto-, oxo-, formyl-, nitro-, cyano-, halo- or trihalomethyl groups. Substituents with an +I effect are capable for increasing the pka of such weak bases and include for example alkyl groups. The heteroatoms in β- or γ-position of the nitrogen atom and the substituents in α- or β-position of the nitrogen atom may be part of the hydrophobic moiety of the TEE.

The anionic charge of said zwitterion is an acidic group selected from carboxyl-, phosphate-, phophite-, sulfo- or sulfino groups. Preferred are carboxyl groups. The anionic charge may be between 2 and 5 carbon atoms apart from the cationic charge of the zwitterion.

Specific Examples of Preferred TEE's

The following chemical representations of TEE's should further illustrate the teachings of the invention. However, the scope of the invention is by no means limited to the specific examples given below. Preferred TEE's have the following attributes:

| | |
|---|---|
| Number of chain elements in the hydrophobic moiety | 8 . . . 40 |
| logD(7,4) | 1 . . . 10 |
| logD(7,4) − logD(4) | >1 |
| pKa | |
| for weak acids | 2 . . . 6 |
| for weak bases with ability for zwitterion formations | 4.5 . . . 7 |

A. TEE's Based on Carboxylic Acids

In one aspect of the invention the TEE comprises one or more carboxylic acid groups as the hydrophilic moiety.

In some embodiments of such aspect, the hydrophobic moiety comprises a straight chain of carbon atoms. In some representations, such chain is a straight alkyl chain.

Table 5 below is analyzing log D at pH 4 and pH 7.4 for different chain length of the carboxylic acids.

TABLE 5

| # of C | pH 4.0 | pH 7.4 | Δ |
|---|---|---|---|
| 4 | 0.71 | −1.83 | −2.54 |
| 6 | 1.77 | −0.75 | −2.52 |
| 8 | 2.84 | 0.31 | −2.53 |
| 10 | 3.9 | 1.38 | −2.52 |
| 12 | 4.96 | 2.44 | −2.52 |
| 14 | 6.02 | 3.5 | −2.52 |
| 16 | 7.09 | 4.56 | −2.53 |
| 18 | 8.15 | 5.62 | −2.53 |
| 20 | 9.21 | 6.69 | −2.52 |

It becomes apparent that chain elongation by an methylene group increases the log D by about 0.5 units. Carboxylic acids with 6 to 26 C atoms represent preferred TEE's according to the selection criteria given above.

Position effects of the carboxylic acid group are less important and the carboxylic group is not mandatory the terminal group of the hydrophobic moiety.

In some aspects, one or more positions of the main chain of the hydrophobic moiety can be substituted (R—) and the impact of some substitutions is analyzed below for hexadecanoic acid (palmitic acid) derivatives (table 6).

TABLE 6

| methyl side chain ||| ethyl side chain ||| propyl side chain |||
|---|---|---|---|---|---|---|---|---|---|---|---|
| # subs | pH 4.0 | pH 7.4 | Δ | # subs | pH 4.0 | pH 7.4 | Δ | # subs | pH 4.0 | pH 7.4 | Δ |
| 0 | 7.09 | 4.56 | −2.53 | 0 | 7.09 | 4.56 | −2.53 | 0 | 7.09 | 4.56 | −2.53 |
| 1 | 7.43 | 4.91 | −2.52 | 1 | 7.96 | 5.44 | −2.52 | 1 | 8.5 | 5.98 | −2.52 |
| 2 | 7.78 | 5.26 | −2.52 | 2 | 8.84 | 6.32 | −2.52 | 2 | 9.91 | 7.38 | −2.53 |
| 3 | 8.13 | 5.6 | −2.53 | 3 | 9.72 | 7.2 | −2.52 | 3 | 11.32 | 8.79 | −2.53 |

If R=methyl, each R results in a gain in log D of about 0.35 units. If R=ethyl, such gain is about 0.88 and for R=propyl the gain is about 1.41 per substitution. It becomes apparent that addition of methylene groups in side chain also increase log D by about 0.5 units as it is the case in the main chain.

In other aspects, R comprises heteroatoms, in particular oxygen atoms and the impact for some substitutions is analyzed below for hexadecanoic acid (palmitic acid) derivatives (table 7).

TABLE 7

| methoxy side chain ||| ethoxy side chain ||| MOE side chain |||
|---|---|---|---|---|---|---|---|---|---|---|---|
| # subs | pH 4.0 | pH 7.4 | Δ | # subs | pH 4.0 | pH 7.4 | Δ | # subs | pH 4.0 | pH 7.4 | Δ |
| 0 | 7.09 | 4.56 | −2.53 | 0 | 7.09 | 4.56 | −2.53 | 0 | 7.09 | 4.56 | −2.53 |
| 1 | 6.03 | 3.35 | −2.68 | 1 | 6.56 | 3.9 | −2.66 | 1 | 6.89 | 4.31 | −2.58 |
| 2 | 4.48 | 1.8 | −2.68 | 2 | 5.54 | 2.87 | −2.67 | 2 | 6.4 | 3.81 | −2.59 |
| 3 | 2.92 | 0.24 | −2.68 | 3 | 4.52 | 1.85 | −2.67 | 3 | 5.91 | 3.32 | −2.59 |

For R=methoxy each R results in a decrease of log D of about −1.4 units. If R=ethoxy, the extra methylene group contributes about 0.5 units of log D and the resulting effect is about −0.9 units of log D. If R=methoxyethyl, the average impact per substitution is about −0.4 units of log D.

Other substitutions on the side chain may further change the log D of the chain with different impact and some examples for R are given in table 8 below (analysis based on hexadecanoic acid).

TABLE 8

| R = | D (log(D)) | R = | D (log(D)) |
|---|---|---|---|
| Vinyl | +0.4 | Methoxymethyl- | −1 |
| Chloro | −0.2 . . . −0.5 | Ethoxymethyl- | −0.5 |
| Fluoro | −0.9 | Ethoxyethyl- | 0 |
| Bromo | −0.35 . . . +0.2 | Keto- | −2.2 . . . −1.7 |
| Hydroxyl | −1.2 . . . 2.2 | | |

The substituents itself are not pH-responsive and therefore do not contribute to the pH-response of the TEE. Also, the impact of R is independent of the pH. However, as pointed out before R may influence the pKa of the hydrophilic moiety, thereby changing the amplitude of log(D) between physiological pH and pH 4 . . . 5.

In still other aspects, heteroatoms may be part of the main chain of the hydrophobic moiety. In other aspects, the main chain may comprise non-saturated bonds. In still other aspects, the main chain may comprise heteroatoms in combination with substitutions in the side chain. Such changes may influence the log D of the TEE and some variations for the main chain have been analyzed for hexadecanoic acid (table 9).

TABLE 9

| double bonds (—2H) ||| ether in main chain (PEG) ||| ether in main chain (PPG) |||
|---|---|---|---|---|---|---|---|---|---|---|---|
| # subs | pH 4.0 | pH 7.4 | Δ | # subs | pH 4.0 | pH 7.4 | Δ | # subs | pH 4.0 | pH 7.4 | Δ |
| 0 | 7.09 | 4.56 | −2.53 | 0 | 7.09 | 4.56 | −2.53 | 0 | 7.09 | 4.56 | −2.53 |
| 1 | 7.11 | 4.59 | −2.52 | 1 | 5.16 | 2.54 | −2.62 | 1 | 5.51 | 2.88 | −2.63 |

TABLE 9-continued

| double bonds (—2H) | | | | ether in main chain (PEG) | | | | ether in main chain (PPG) | | | |
|---|---|---|---|---|---|---|---|---|---|---|---|
| # subs | pH 4.0 | pH 7.4 | Δ | # subs | pH 4.0 | pH 7.4 | Δ | # subs | pH 4.0 | pH 7.4 | Δ |
| 2 | 6.58 | 3.99 | −2.59 | 2 | 3.21 | 0.57 | −2.64 | 2 | 3.9 | 1.26 | −2.64 |
| 3 | 5.95 | 3.09 | −2.86 | 3 | −0.69 | −3.33 | −2.64 | 3 | 2.3 | −0.34 | −2.64 |

A double bond therefore reduces log D by about −0.4 to 0.5 units, ether bonds in the main chain as found in repetitive structures derived from poly-ethylenglycol reduce log D by about 2.5 units, said effect being reduced to about 1.6 units by addition of an additional methyl group next to the ether bond, such as in the repetitive structures from poly-propylenegly-col.

Other substitutions on the main chain may further change the log D of the chain with different impact and some examples are given in table 10 below (analysis based on hexadecanoic acid).

TABLE 10

| element | D (log(D)) | element | D (log(D)) |
|---|---|---|---|
| —CH$_2$— | Reference | —S— | −1.5 |
| —NH—(Aza) | −6 ... −9 | —S—S— | −1.1 |
| —NH—CO—(Amide) | −7.5 ... −11 | | |
| —O—CO—(Ester) | −2.7 | | |

The substituents itself are not pH-responsive and therefore do not contribute to the pH-response of the TEE. Also, the impact of R is independent of the pH. However, as pointed out before R may influence the pKa of the hydrophilic moiety, thereby changing the amplitude of log(D) between physiological pH and pH4 ... 5.

The examples and analysis presented above give guidance for practicing the invention, in particular to identify structural elements as TEE's. Isoforms and position isomers are within the disclosure of the current invention. As mentioned earlier in this disclosure, neighbouring effects between substituents may occur. However, these effects are known to the skilled artisan and are described in the standard chemical literature, in databases or are part of chemical software such as ACD/Labs and others.

Ring Systems

In some aspects, the hydrophobic moiety may form a cyclic structure such as cycloalkanes, cycloalkenes or cycloalkynes or aromatic ring structures.

A few representations of cyclic elements have been analyzed in the table below and more cyclic elements can be developed from known structural contributions of other elements. It is of course possible to further substitute the cyclic elements, in particular with the groups analyzed above.

TABLE 11

| | Cyclic backbone | | | |
|---|---|---|---|---|
| cpd | pH 4.0 | pH 7.4 | Δ | |
| stearic acid | 8.15 | 5.62 | −2.53 | |
| 4-undecyl cyclohexanoic acid | 7.54 | 5.22 | −2.32 | |
| 4-undecyl cyclohexenoic acid | 7.12 | 4.39 | −2.73 | |
| p-undecyl benzoic acid | 7.51 | 4.87 | −2.64 | |

Sterols

In a specific variant of the invention, the ring systems of the hydrophobic moieties may be more complex ring systems such as in sterols. Again, further substitutions may be present at the sterol backbone and the analysis shown below is detailing some aspects of log D for natural occurring derivatives of sterols, e.g. hydroxyl group substitutions at positions 3, 7, and 12 of the sterane backbone.

Also, the orientation of the sterol in the TEE may be different and a presence of the carboxyl group at position 26 such as in bile acids or grafted onto position 3 such as in cholesterol hemisuccinate (CHEMS) represent some instant examples (tables 12 and 13).

TABLE 12

Analysis of logD for bile acid derivatives used as TEE's.
For analytical purposes, the 3' hydroxyl group was assumed
to be methylated to model a potential drug linkage

| bile acids | OH in backbone | | | |
|---|---|---|---|---|
| (3'cholesterols) | # subs | pH 4.0 | pH 7.4 | Δ |
| 3' methoxy cholate | 3 | 3.18 | 0.64 | −2.54 |
| 3' methoxy deoxycholate | 2 | 5.23 | 2.69 | −2.54 |
| 3' methoxy dideoxycholate | 1 | 7.27 | 4.73 | −2.54 |

TABLE 13

Analysis of logD for CHEMS derivatives used for TEE's.
For analytical purposes, the carboxyl group in position 26 was esterified
with methanol to model a potential drug linkage. In this analysis,
the 3' position is esterified with succinic acid, thereby providing an
unsubstituted carboxyl group as the hydrophilic moiety of the TEE.

| CHEMS derivatives | OH in backbone | | | |
|---|---|---|---|---|
| (26' cholesterols) | # subs | pH 4.0 | pH 7.4 | Δ |
| 26' methyl cholate | 3 | 3.65 | 1.01 | −2.64 |
| 26' methyl deoxycholate | 2 | 5.69 | 3.06 | −2.63 |
| 26' methyl dideoxycholate | 1 | 7.73 | 5.1 | −2.63 |

B. TEE's Based on Barbituric Acids and Xanthines

The considerations above can of course be transferred to TEE's comprising structurally different hydrophilic moieties. Contributions of structural elements in the hydrophobic section of the TEE are close if not identical irrespective of the chemical nature of the hydrophilic moiety or moieties. Some specific chemical representations of TEE's comprising barbituric acid or xanthine may illustrate the construction of such TEE's without limiting this part of the disclosure (compounds 17-23).

(17)
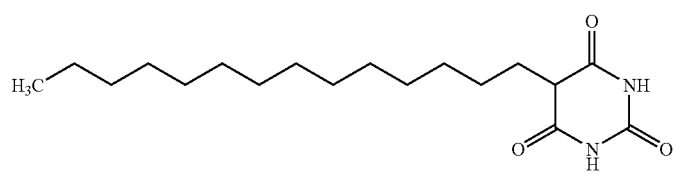
(18)
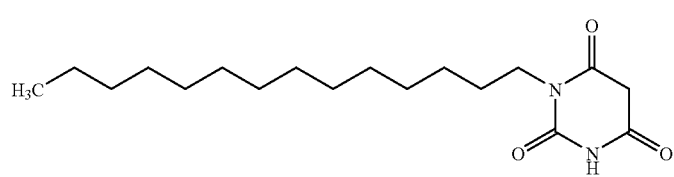
(19)
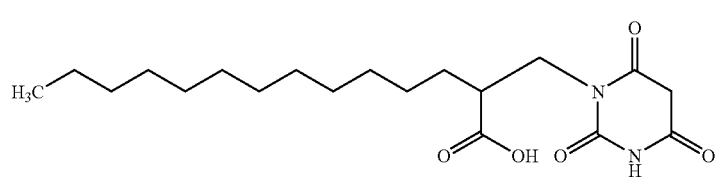
(20)
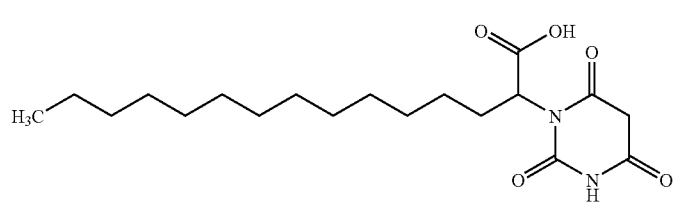
(21)
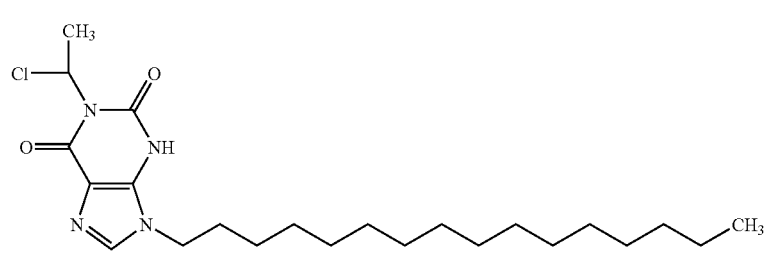
(22)
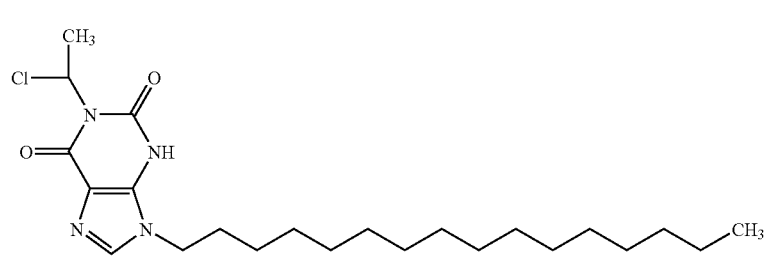
(23)
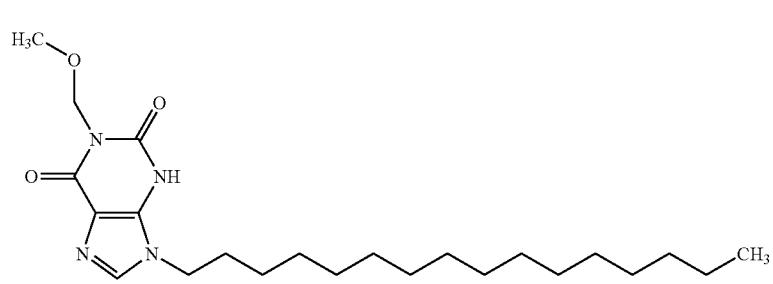

The position of the hydrophilic moiety within the TEE structure may vary. In some aspects, the hydrophilic moiety is located distal from the link between molecule and TEE. In other aspects, the hydrophilic moiety is located central within the TEE.

Use of TEE's

TEE's need to be combined to a lipid or a liposomes or other supramolecular aggregates such as micelles, lipoplexes, cochleates, emulsion droplets and the like, altogether called lipid assemblies within this invention.

For the combination of TEE's with lipid assemblies a number of different approaches can be taken including but not limited to chemical bonds, physical attractions or by other interactions, e.g. chelate bonds.

In one aspect of the invention, the TEE's can directly be linked to a lipid by means of chemical bonds; lipids comprising TEE's are described in detail further below.

In another aspect of the invention, TEE's can be grafted on the lipid assembly after such assembly has been produced. Chemical conjugation techniques and methods for carrying out such couplings have extensively been reported in the literature, e.g. by G. T. Hermanson, Bioconjugate Techniques, Academic Press, 1996.

In another aspect of the invention, TEE's may be complexed with the lipid assembly systems using molecular recognition, e.g. between biotin and biotin binding proteins, between two complementary or partially complementary oligonucleotides or between cyclodextrins and molecules fitting the binding pockets of the cyclodextrin such as various lipids or detergents as disclosed in DeGrip et al., Biochem. J., 330, 667-674, 1998, sterols or adamantane units as disclosed in WO 06/105361, other sterols such as steroids or adamantane units as disclosed in WO 06/105361.

In another aspect, TEE's may be complexed with lipid assemblies using ionic or electrostatic interaction. In one embodiment of such aspect, TEE's further comprising a polycationic element are combined with anionic lipid assemblies. In another embodiment, TEE's further comprising a polyanionic element are combined with cationic lipid assemblies. Examples for polycationic elements include, but are not limited to polyethylenimine, polyallylamine, spermine, thermine, spermidine, dispermine, trispermine, tetraspermine, oligospermine, putrescine or polymers or oligomers from lysine, ornithine or arginine and the like. Examples for polyanionic elements include, but are not limited to polymers or oligomers of acrylic acid, methacrylic acid, glutamic acid, aspartic acid and the like. Techniques and experimental protocols for the combination of lipid assemblies with polyions are disclosed in WO 01/64330.

TEE derivatives for such use include, but are not limited to the compounds 24-29.

TABLE 14

Compounds 24-29

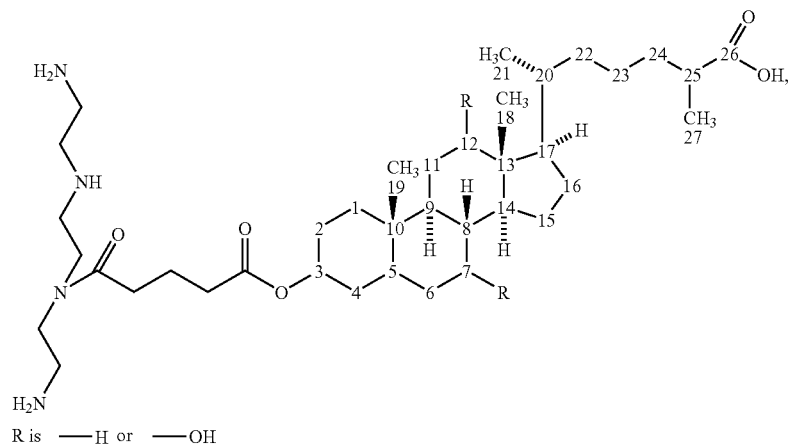

(24)

R is —H or —OH

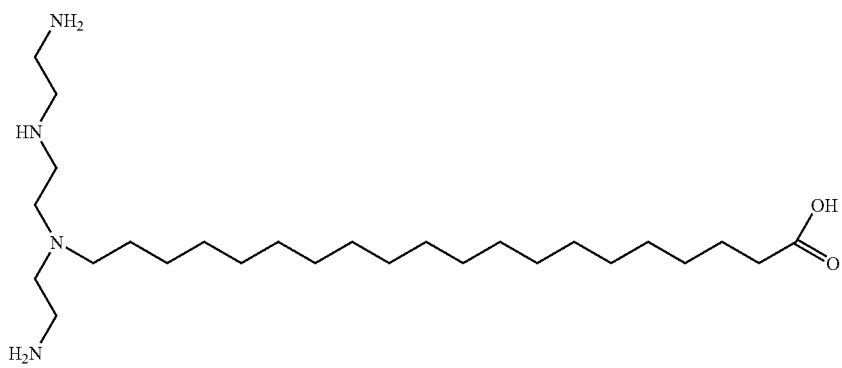

(25)

TABLE 14-continued
Compounds 24-29
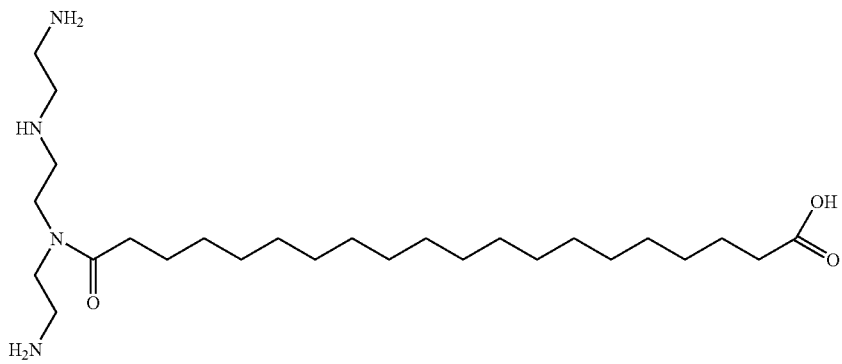
(26)
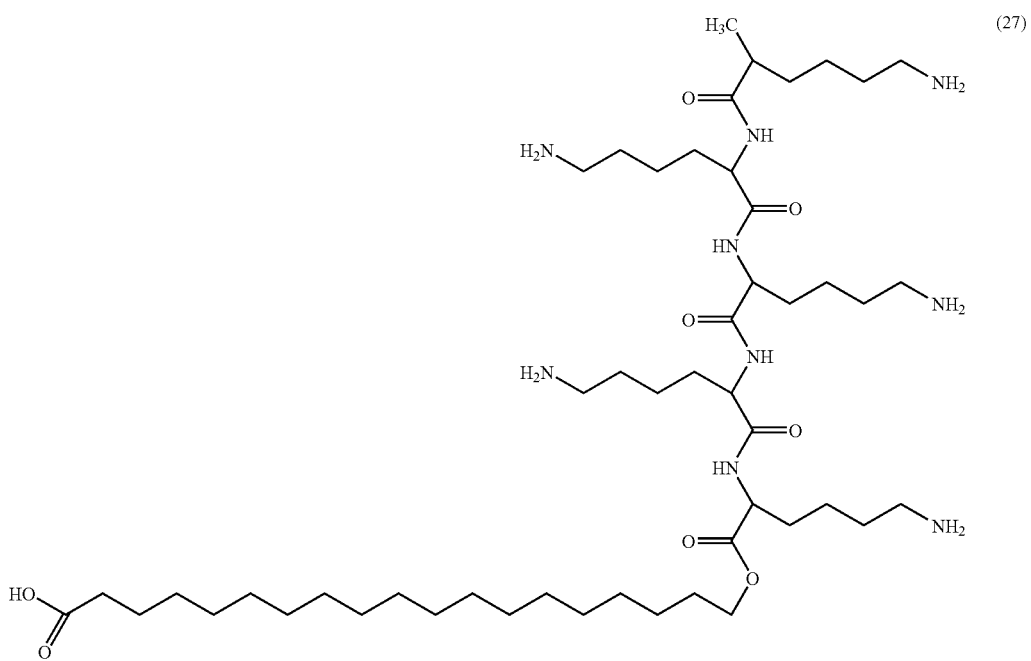
(27)

TABLE 14-continued

Compounds 24-29

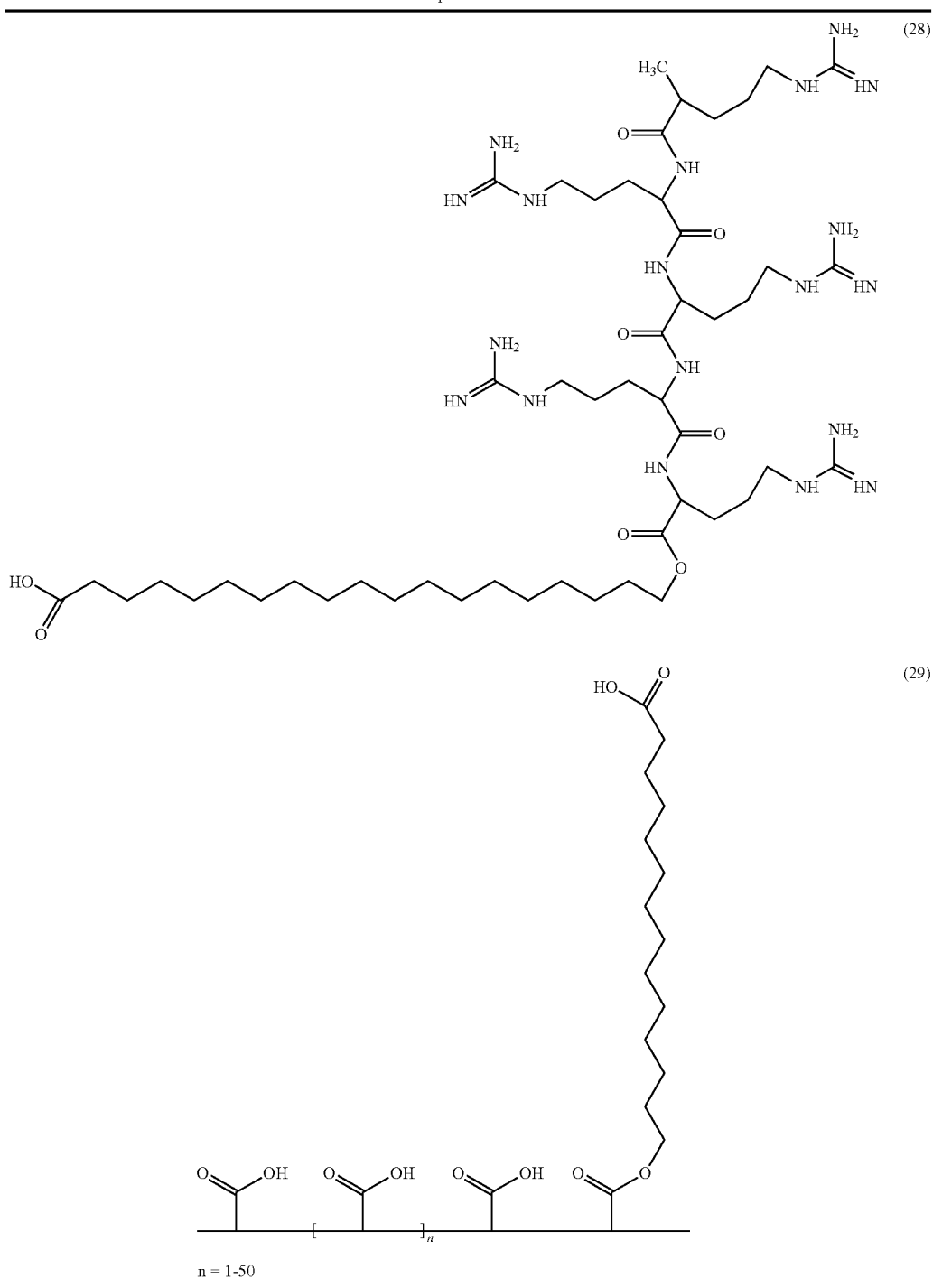

Lipids Comprising TEE's

In one embodiment of the invention lipids comprising one or more TEE's may have the following general formula Lipid-(L2)r-(TEE)r     (XII)

wherein L2 is absent or a linking group selected from —CH$_2$—, —O—; —S—; —N(H)C(O)—; —C(O)N(H)—; —C(O)O—; —OC(O)N(H)—; —C(O)—; —C(O)N(H)—; —N(H)C(O)O—; —NH—, —CH=N—; —OC(O)—; —N=CH—; —S—S—, —N(R$_{13}$)(R$_{14}$)— with R$_{13}$ and R$_{14}$ are independently H or C$_1$-C$_6$ alkyl or one of R$_{13}$ or R$_{14}$ may be absent and wherein r is an integer of 1-5.

Lipids to which the TEE may be attached according to the present invention may be selected without limitation from the group comprising phospholipids and their lyso forms, sphingolipids and their lyso forms, sterols like cholesterols and derivatives thereof, diacylglycerols/dialkylglycerols, monacylglycerols/monoalkylglycerols, monoester, diesters, monoethers or diethers of glyceric acid, sphingosines/ phytosphingosines/sphinganines and N-substituted derivatives thereof, ceramides, 1,2-Diacyl-3-aminopropanes/1,2-Dialkyl-3-aminopropanes, 1- or 2-monoacyl-3 aminopropanes/1- or 2-monoalkyl-3-aminopropanes, dialkylamines, monoalkylamines, fatty acids, dicarboxylic acid alkyl ester, tricarboxylic acid dialkyl ester optionally substituted with —OH groups or esters of tartaric acid with long chain alcohols or esters of tartaric acid with long chain carboxylic acids.

In a preferred embodiment the acyl- and alkyl-chains of the amphiphilic lipid substances comprise independently 8-30 carbon atoms and 0, 1 or 2 ethylenically unsaturated bonds. In other preferred embodiments the amphiphilic lipid substances comprise sterol derivatives, preferably cholesterol and derivatives thereof.

In one embodiment of the invention lipids to which one or more TEE may be attached may be selected from one of the following general formula:

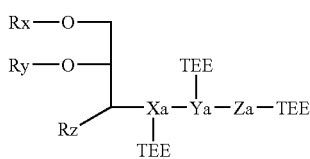
(XIII)

wherein Rx and Ry are independently $C_8$-$C_{30}$ alkyl or acyl chains with 0, 1 or 2 ethylenically unsaturated bonds or one of Rx or Ry may be H, Rz is H, =O, —$NH_2$, —OH Xa is —$OPO_3^-$—; —$OPO_2^-CH_2$—; -pyrophosphate-; —$OSO_3$—; —$OSO_2$—; —O—; —NH—; —S—; —N(H)C(O)—; —C(O)—, —C(O)N(H)—; —OC(O)N(H)—; —N(H)C(O)O—; —OC(O)—; —C(O)O—; —N=CH—; —CH=N—; —$CH_2$—; —S—S—; —N($R_{13}$)($R_{14}$)— with $R_{13}$ and $R_{14}$ are independently H or $C_1$-$C_6$ alkyl or one of $R_{13}$ or $R_{14}$ may be absent; or

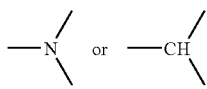

and

Ya is absent or a non-branched, branched or cyclic substituted or unsubstituted alkyl, alkenyl; alkylene or alkynyl or a aryl group with 1 to 8 C-atoms wherein said substituents are selected from one or more —OH; —$NH_2$; —N($R_{13}$)($R_{14}$) with $R_{13}$ and $R_{14}$ are defined above; —COOH; sugars or Ya is a sugar; amino acids; di- or tripeptide; α-hydroxyacid or β-hydroxyacid or dihydroxyacid and Za is absent or a group selected from —O—; —S—; —N(H)C(O)—; —C(O)N(H)—; —C(O)O—; —OC(O)N(H)—; —C(O)—; —C(O)N(H)—; —N(H)C(O)O—; —NH—; —N($R_{13}$)($R_{14}$)— with $R_{13}$ and $R_{14}$ are defined as above; —CH=N—; —OC(O)—; —N=CH—; —S—S— or Za is selected from the group —$NH_2$; —($NH_3$)$^+$; —(N($R_{13}$)($R_{14}$)($R_{15}$))$^+$ with $R_{13}$; $R_{14}$; and $R_{15}$ are defined as $R_{13}$ and $R_{14}$ above; —C(O)OH; —OH; —C(O)H; —C(O)O$R_{16}$ with $R_{16}$ is $C_1$-$C_6$ alkyl; —C(O)$NH_2$ and wherein the dotted lines represent possible graft positions of the one or more TEE's.

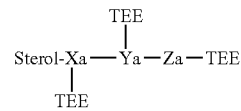
(XIV)

wherein Xa is bound at the 3' position of the sterol and is defined as above and Ya and Za are defined as above and wherein the sterol is selected from cholesterol, sitosterol, campesterol, desmosterol, fucosterol, 22-ketosterol, 20-hydroxysterol, stigmasterol, 22-hydroxycholesterol, 25-hydroxycholesterol, lanosterol, 7-dehydrocholesterol, dihydrocholesterol, 19-hydroxycholesterol, 5α-cholest-7-en3β-ol, 7-hydroxycholesterol, epicholesterol, ergosterol, and/or dehydroergosterol and wherein preferably said sterol is cholesterol and wherein the dotted lines represent possible graft positions of the one or more TEE's.

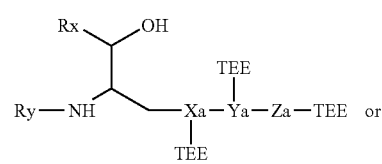
(XV)

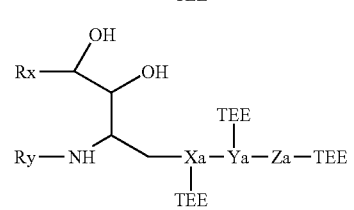
(XVI)

wherein Rx, Ry, Xa, Ya or Za are defined as above and the dotted lines represent possible graft positions of the one or more TEE's.

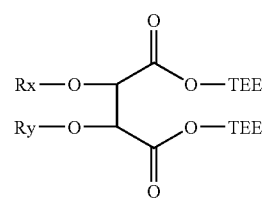
(XVII)

wherein Rx and Ry are defined as above and the dotted lines represent possible graft positions of the one or more TEE's.

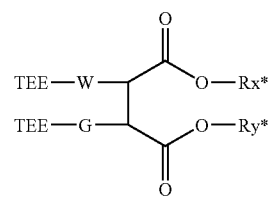
(XVIII)

wherein Rx* and Ry* are independently $C_8$-$C_{30}$ alkyl chains with 0, 1 or 2 ethylenically unsaturated bonds or one of Rx* or Ry* may be H and W and G are independently HO—, —O—, —S—, —N(H)C(O)—, —C(O)O—, —N(H)C(O)O— and the dotted lines represent possible graft positions of the one or more TEE's.

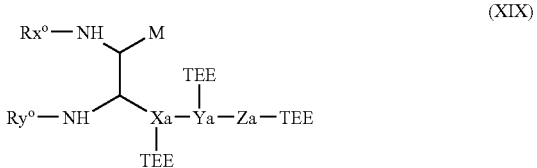

(XIX)

wherein Rx° and Ry° are independently $C_8$-$C_{30}$ acyl chains with 0, 1 or 2 ethylenically unsaturated bonds or one of Rx° or Rx° may be H, M is H or —OH and Xa, Ya, Za are defined as above and the dotted lines represent possible graft positions of the one or more TEE's.

Graft Positions

The TEE's of the invention can be chemically linked or grafted onto a lipid. In many aspects, the water exposed, polar lipid head group is the preferred position for grafting one or more TEE's.

Chemical linkers between the graft and the TEE may include and comprise but are not limited to —O—, —S—, —N(H)C(O)—, —C(O)O—, —OC(O)N(H)—, —C(O)—, —C(O)—N(H)—, —N(H)—C(O)—O—, —CH=N—, —O—C(O)—, —N=CH—, —S—S—, non-branched, branched or cyclic alkyl, alkenyl, alkylene or alkynyl with 1 to 6 C-atoms and optionally substituted with one or more —OH, —$NR_2$, —COOH or sugars or mixtures thereof; —$PO_4^-$—; —$PO_3^-$—; —$PO_3^-CH_2$-pyrophosphate; —$SO_4$—; —$SO_3$—; —NH—; —NR—; sugars and derivatives thereof; amino acids; Di- or Tripeptides, α-hydroxyacids or β-hydroxy acids or dihydroxyacids.

In preferred embodiments of this invention the structural unit of the lipid head group and the chemical linker group maintains substantial polarity. In a number of aspects this structural unit is carrying a charge. This might be a preserved charge from the former head group or a newly generated charge, e.g. an amine group resulting from reductive amination.

In other aspects, the polar region of (I) is defined as the (continuous) structural unit outside the membrane anchors of the lipid and also outside of the actual TEE and said structural unit maintains substantial polarity. Substantial polarity describes the ability to form hydrogen bonds in water. Substantial polarity means a log D<0, in some aspects log D<-2 and in other aspects a log D<-4.

In some embodiments of the invention the TEE is grafted onto a lipid comprising a charged polar head group, wherein the graft position is said charged polar head group and keeps the charge of that group at least to a substantial extent. Examples for such hydrophilic polar head groups of lipids comprise, but are not limited to phosphoric acid (in lipids like DOPA), phosphoethanol (in lipids like DOPE), phosphoglycerol (in lipids like POPG), phosphoglycerolaldehyde, phosphoglyceric acid, Amino groups (e.g. derived from 1,2-diacyl or 1, 2 dialkyl-3 aminopropanes).

Chemical representations of such lipids comprising TEE's include without limitation compounds 30-43. $R_x$ and $R_y$ independently are $C_8$-$C_{30}$ alkyl or acyl chains with 0, 1 or 2 ethylenically unsaturated bonds or one of Rx or Ry may be H and $R_{3*}$ and $R_{4*}$ are independently H or $C_1$-$C_6$ alkyls.

TABLE 15

Compounds 30-43

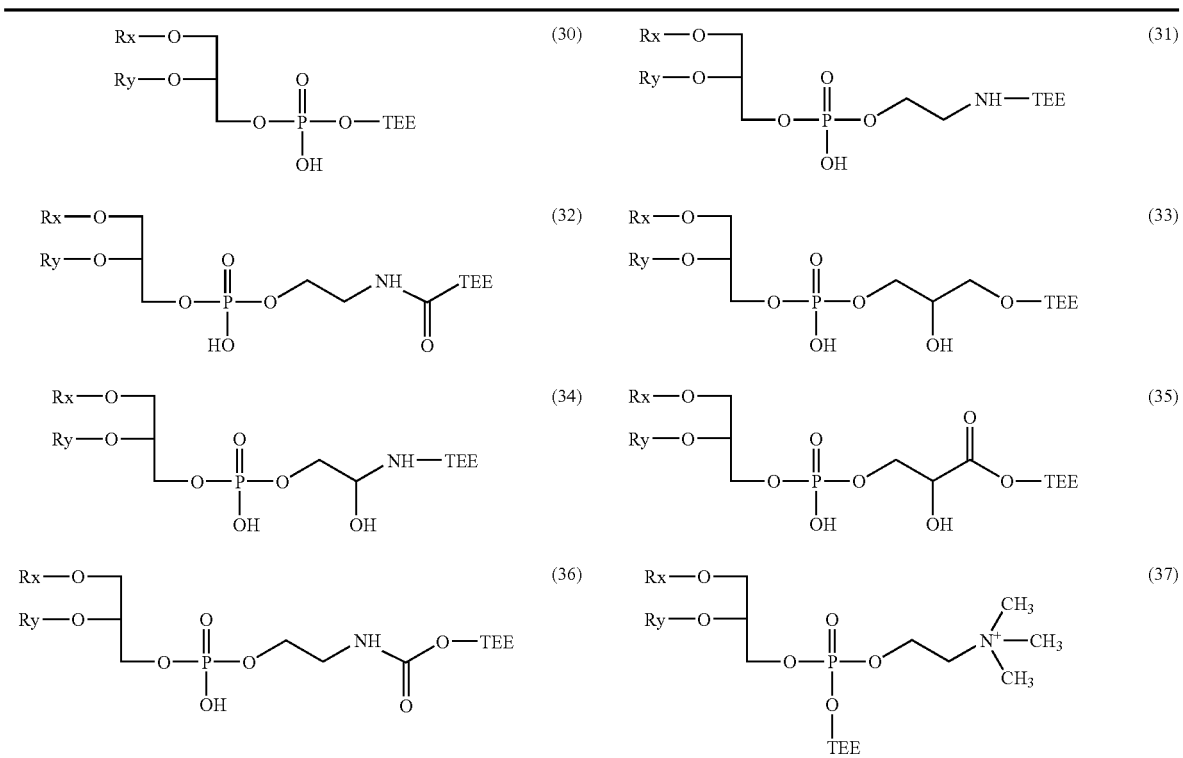

TABLE 15-continued

Compounds 30-43

(38) [Structure: Rx—O—, Ry—O—CH2—O—P(=O)(OH)—O—CH2—CH(NH-TEE)—C(=O)—OH]

(39) [Structure: Rx—O—, Ry—O—CH2—O—P(=O)(OH)—O—CH2—CH(NH2)—C(=O)—O—TEE]

(40) [Structure: Rx—O—, Ry—O—CH2—O—P(=O)(OH)—O—CH2—CH(NH2)—C(=O)—NH—TEE]

(41) [Structure: Rx—C(=O)—NH—CH(Ry)(OH)—CH2—O—P(=O)(O-TEE)—O—CH2CH2—N+(CH3)3]

(42) [Structure: Rx—C(=O)—NH—CH(Ry)(OH)—CH2—O—TEE]

(43) [Structure: Rx—O—, Ry—O—CH2—NH—TEE]

(42a) [Structure: Rx—O—, Ry—O—CH2—O—P(=O)(O-TEE)—O—CH2CH2—NH2]

(43a) [Structure: Rx—O—, Ry—O—CH2—N+(R3*)(R4*)—TEE]

In another embodiment of the invention the TEE is grafted on a lipid comprising a hydrophilic polar head group, wherein the graft position is said hydrophilic group but the chemical linkage between TEE and lipid renders the polar head group uncharged. Examples include but are not limited to —N(H)—C(O)—, —N(H)—C(O)O—.

Chemical representations of such lipids comprising TEE's include without limitation compounds 44-47. $R_x$ and $R_y$ independently are $C_8$-$C_{30}$ alkyl or acyl chains with 0, 1 or 2 ethylenically unsaturated bonds or one of Rx or Ry may be H.

TABLE 16

(44) [Structure: Rx—O—, Ry—O—CH2—NH—C(=O)—TEE]

(45) [Structure: Rx—O—, Ry—O—CH2—O—C(=O)—NH—TEE]

(46) [Structure: Rx—O—, Ry—O—CH2—C(=O)—NH—TEE]

TABLE 16-continued

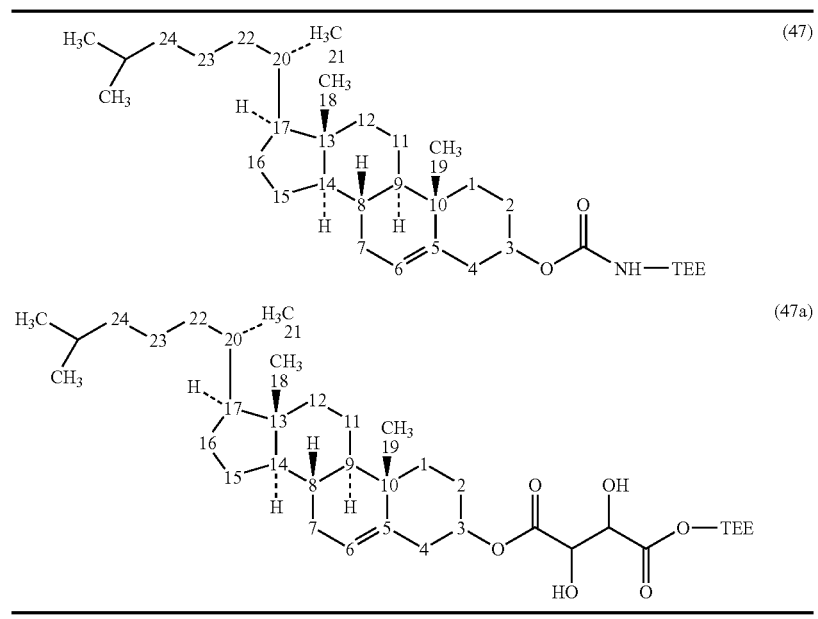

Of course, in all cases substituents may be attached to the lipid headgroups. Furthermore, as mentioned above, linking groups may be inserted between the lipid headgroup and the attached TEE. In some aspects the linking groups are substituted as well.

In a preferred embodiment substituents or linking groups may be used when the attachment of a TEE to a lipid headgroup leads to a decrease of the polarity of the headgroup and subsequent to a loss of the amphiphilic character of the lipid.

For example, the esterification of cholesterol with a $C_{16}$-dicarboxylic acid as TEE results in an apolar ester bond and is therefore not preferred. However, the insertion of a polar linking group, e.g. tartaric acid, between the cholesterol and the $C_{16}$-dicarboxylic acid as TEE preserves the amphiphilic structure of the lipid, also after the attachment of the TEE.

In some embodiments the substituents that may be attached to the lipid headgroups are polar and include, but are not limited to groups like —OH, —COOH, —$NH_2$, —NHR, —$NR_2$, sugars and derivatives thereof, amino acids and derivatives thereof, —$OPO_3^{2-}$, —$OPO_2^{2-}$, —$OSO_3^-$; —$OSO_2^-$ or mixtures thereof.

Chemical representations of such lipids having linking groups between the headgroup and the TEE include without limitation compounds 48-49. $R_x$ and $R_y$ independently are $C_8$-$C_{30}$ alkyl or acyl chains with 0, 1 or 2 ethylenically unsaturated bonds or one of Rx or Ry may be H.

TABLE 17

Compounds 48 and 49

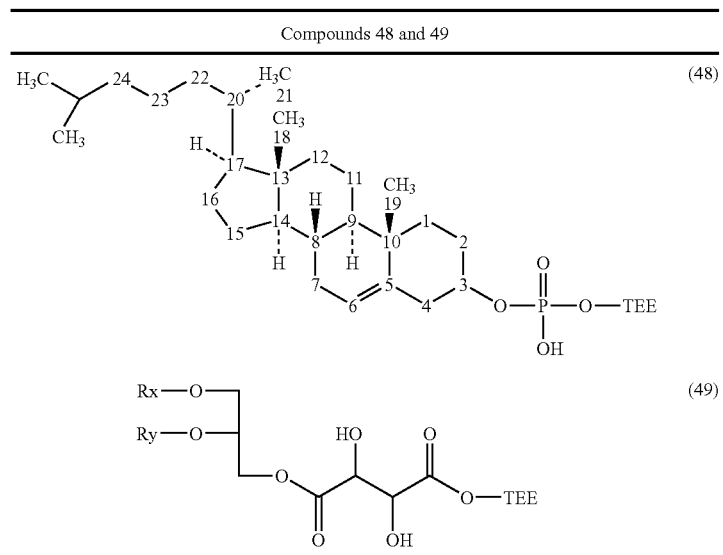

In some variants of the invention, the lipid may contain more than one hydrophilic polar head group or complex hydrophilic head groups that allow substitution on various positions without affecting hydrophilicity. Examples include, but are not limited to esters of tartaric acid with long chain alcohols, derivatives of maleic acid or esters of fatty acids with sugars such as glucose, sucrose or maltose. Further examples include, without limitation, alkyl glycosides and derivatives thereof, such as dodecyl-β-D-glucopyranoside or dodecyl-β-D-maltoside, derivatives of alkyl-ethylenglycol detergents (such as Brij 35, Genapol series, Thesit and the like) or Phosphatidylinositols and derivatives thereof. Isomers wherein the TEE is grafted onto different positions of such polar head groups are within the scope of this invention.

Chemical representations of such lipids with more than one hydrophilic headgroups or complex headgroups comprising a TEE include without limitation compounds 50-55. $R_x$ and $R_y$ independently are $C_8$-$C_{30}$ alkyl or acyl chains with 0, 1 or 2 ethylenically unsaturated bonds or one of Rx or Ry may be H. R* are $C_8$-$C_{30}$ alkyl chains with 0, 1 or 2 ethylenically unsaturated bonds.

TABLE 18

Compounds 50-55

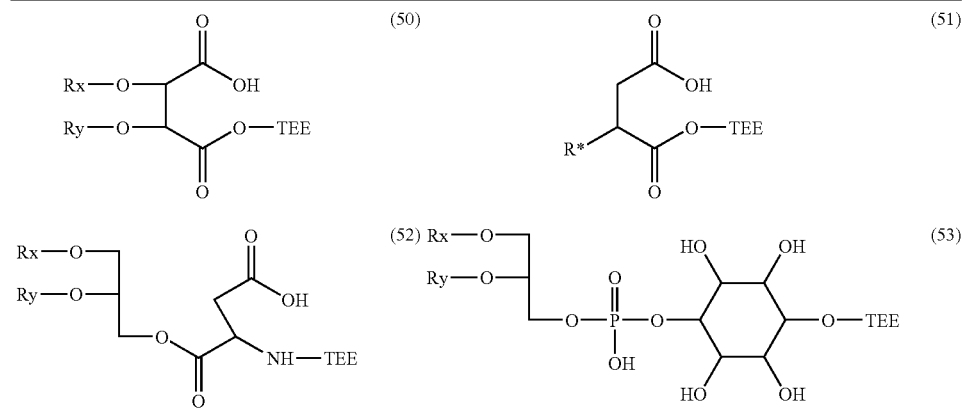

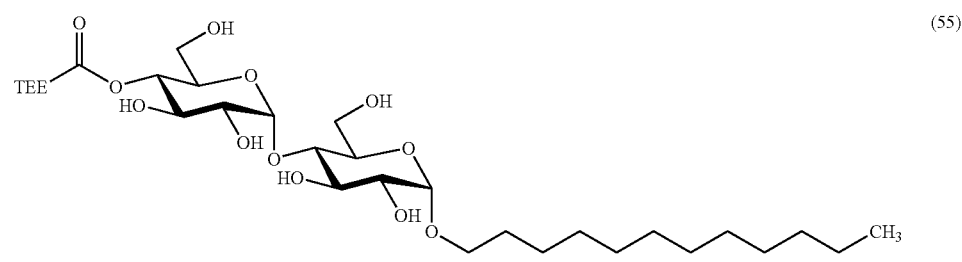

In some variants of the invention, more than a single TEE may be attached to one lipid.

Chemical representations of such lipids comprising more than one TEE include without limitation compounds 56-60. $R_x$ and $R_y$ independently are $C_8$-$C_{30}$ alkyl or acyl chains with 0, 1 or 2 ethylenically unsaturated bonds or one of Rx or Ry may be H.

TABLE 19

Compounds 56-60

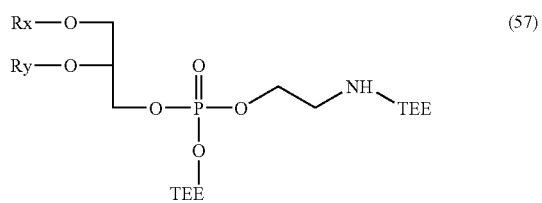

TABLE 19-continued

Compounds 56-60

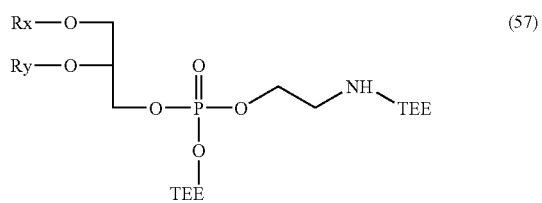

TABLE 19-continued

Compounds 56-60

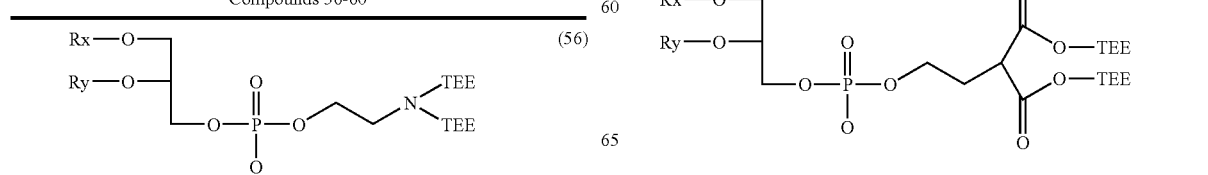

TABLE 19-continued

Compounds 56-60

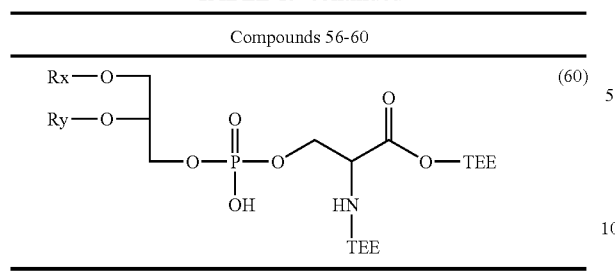
(60)

In some aspects of the invention the lipids-TEE (structures according to the general formula (I)) may be other than one of the following structures (III):

PE-amid linkage-X—COOH        (III)

wherein X is a carbon containing linear chain having a chain length of between 3 to 20 atoms and having various degrees of saturation and/or heteroatom compositions and/or substituents and the COOH-group
or (IV)

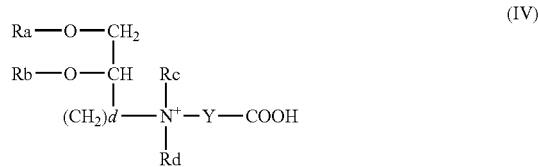
(IV)

wherein Y is a straight saturated alkyl chain having a chain length of between 2 and 10 C-atoms and $R_a$, $R_b$, $R_c$ and $R_d$ are independently linear or branched, unsubstituted or substituted $C_{1-23}$ alkyl, acyl, alkylene, heteroalkyl groups having 0 to 6 sites of unsaturation, cyclic and aryl groups, the groups comprising from 0 to 5 heteroatoms, in which the substituent groups are —O—(CH2)$_e$—CH$_3$; —S—(CH$_2$)$_e$—CH$_3$; A-(CH$_2$)$_e$, wherein A is a halide, and —N((CH$_2$)$_e$—CH$_3$)$_2$, wherein the alkyl groups of the substituents comprise from 0-2 heteroatoms, and e is 0-4 and wherein $R_a$ and $R_b$ can further be independently H and d is 1 to 6
or (V)

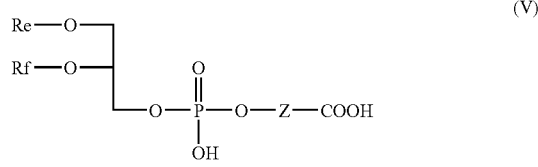
(V)

wherein $R_e$ and $R_f$ independently are hydrogen atoms or $C_1$-$C_{24}$ straight chain or branched alkyl or acyl chains optionally containing double and triple bonds and wherein Z is an aliphatic and/or cycloaliphatic hydrocarbon chain with 6-20 carbon-atoms optionally substituted by aryl rests, cycloalkyls with 3-6 carbon atoms, hydroxyl and/or further carboxylic functions.

In other aspects of the invention the use of lipid assemblies comprising the compounds (III), (IV) or (V) for the in vivo, in vitro or ex-vivo transfection of cells may be preferred.

Specific examples of phospholipids in accordance with the present invention include, but are not limited to:
Phospholipids and Sphingolipids:

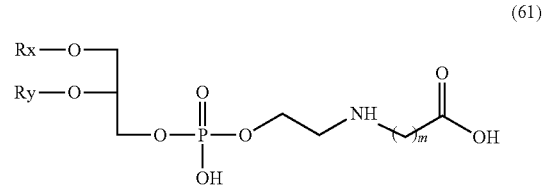
(61)

wherein $R_x$ and $R_y$ independently are $C_8$-$C_{30}$ alkyl or acyl chains with 0, 1 or 2 ethylenically unsaturated bonds or one of Rx or Ry may be H and m=6-40.

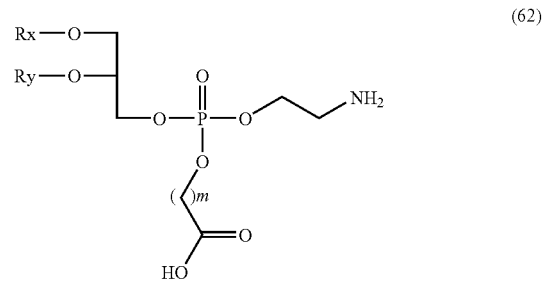
(62)

wherein $R_x$ and $R_y$ independently are $C_8$-$C_{30}$ alkyl or acyl chains with 0, 1 or 2 ethylenically unsaturated bonds or one of Rx or Ry may be H and m=6-40.

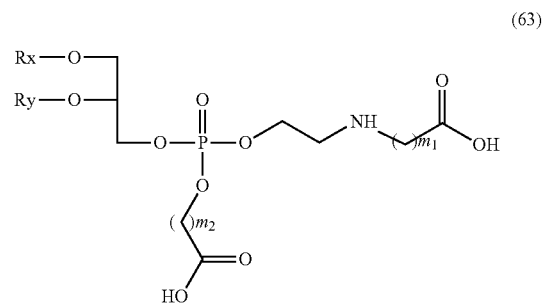
(63)

wherein $R_1$ and $R_2$ independently are $C_8$-$C_{30}$ alkyl or acyl chains with 0, 1 or 2 ethylenically unsaturated bonds or one of R1 or R2 may be H and m1 and m2 are independently 6-40.

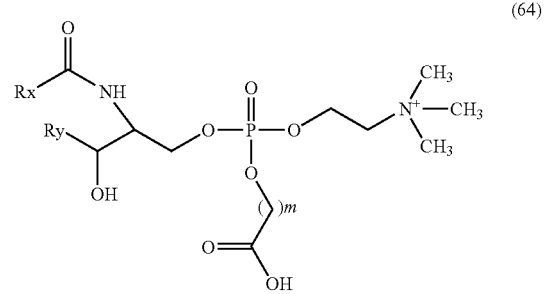
(64)

wherein $R_x$ and $R_y$ independently are $C_8$-$C_{30}$ alkyl chains with 0, 1 or 2 ethylenically unsaturated bonds or one of Rx or Ry may be H and m=6-40.

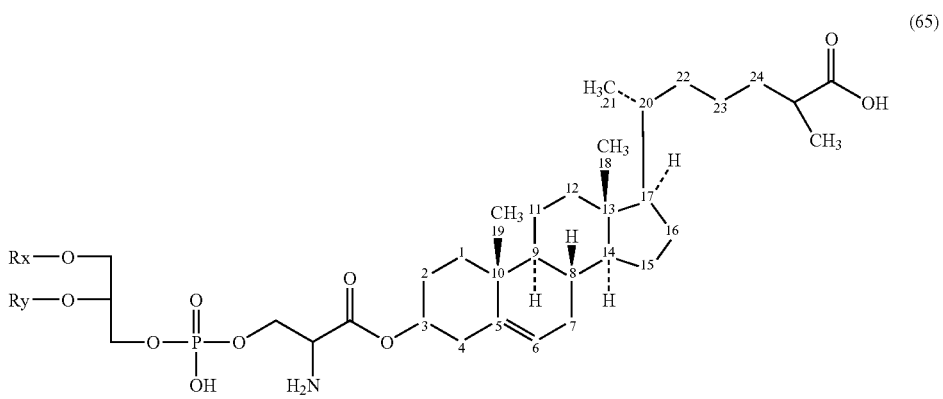
(65)

wherein $R_x$ and $R_y$ independently are $C_8$-$C_{30}$ alkyl or acyl chains with 0, 1 or 2 ethylenically unsaturated bonds or one of Rx or Ry may be H.

Specific examples of sterol based lipids in accordance with the present invention include, but are not limited to:

Sterol Based Lipids:

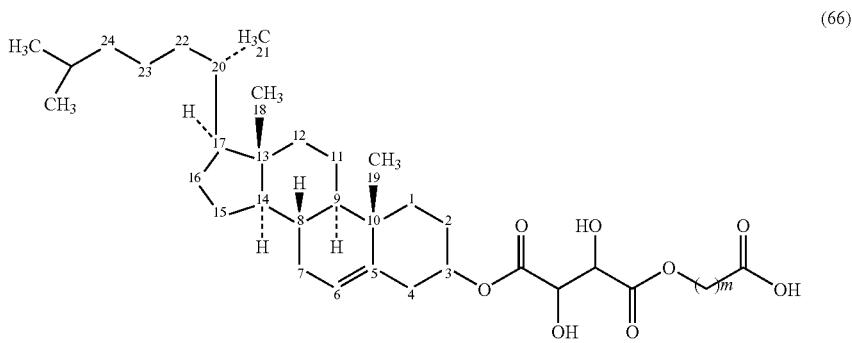
(66)

wherein m=6-40

Specific examples of diacylglycerol/dialkylglycerols based lipids in accordance with the present invention include, but are not limited to:

Diacylglycerol/Dialkylglycerol Based Lipids:

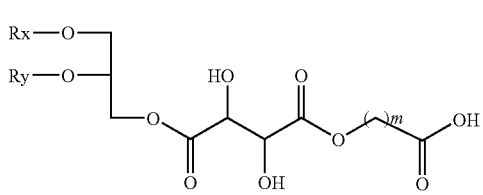
(67)

wherein $R_x$ and $R_y$ independently are $C_8$-$C_{30}$ alkyl or acyl chains with 0, 1 or 2 ethylenically unsaturated bonds or one of Rx or Ry may be H and m=6-40.

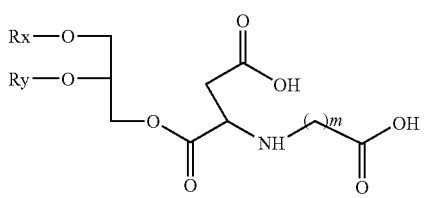
(68)

wherein $R_x$ and $R_y$ independently are $C_8$-$C_{30}$ alkyl or acyl chains with 0, 1 or 2 ethylenically unsaturated bonds or one of Rx or Ry may be H and m=6-40.

Specific examples of 1,2-Diacyl-3-aminopropanes/1,2-Dialkyl-3-aminopropanes based lipids in accordance with the present invention include, but are not limited to:

1,2-Diacyl-3-aminopropanes/1,2-Dialkyl-3-aminopropanes

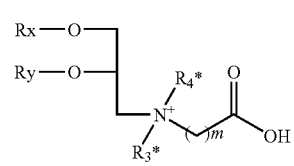
(69)

wherein $R_x$ and $R_y$ independently are $C_8$-$C_{30}$ alkyl or acyl chains with 0, 1 or 2 ethylenically unsaturated bonds or one of Rx or Ry may be H, $R_{3*}$ and $R_{4*}$ are independently H or $C_1$-$C_6$ alkyls and m=11-40.

Methods of synthesising lipids comprising one or more transfection enhancer element as described above include coupling reactions that are well-known to those skilled in the art and may vary depending on the starting material and coupling component employed. Typical reactions are esterification, amidation, etherification, or reductive amination.

Particularly preferred molecules may be prepared by following processes, without being limited on these coupling reactions:
i) reductive amination of a ω-Carboxy-ketone with phosphatidylethanolamine
ii) esterification of the phosphate group in a phospholipid, e.g. PC, PE, PS
iii) esterification of a ω-Dicarboxylic acid with free hydroxyl groups of a lipid
iv) esterification of phosphatidylserine with the 3' hydroxyl group of a cholesterol derivative which has a carboxyl group within the terminal isopropyl group
v) amidation or alkylation of 3-amino-1,2-propanediol diesters,
vi) oxidation of phosphatidyl glycerols and subsequent reductive amination Lipid Assemblies Lipid assemblies are supramolecular assemblies comprising amphipathic molecules. In some aspects the amphipathic substances are known as lipids or as detergents, in other aspects such substances are known to form biological membranes or to insert into biological membranes. The supramolecular assemblies may further comprise oils from apolar molecules. The supramolecular assemblies of the current invention therefore comprise liposomes of various size and lamellarity, micelles, inverted micelles, cubic or hexagonal lipid phases, cochleates, emulsions, double emulsions or other multimeric assemblies that are substantially build from lipids, oils or amphiphiles.

In some embodiments of this invention the lipid assemblies comprise one or more lipids with one or more transfection enhancer elements may be formed from a lipid phase further comprising neutral and/or cationic and/or anionic lipids. The overall charge of the lipid assemblies can be neutral, cationic or anionic.

Lipids, that may be used to form lipid assemblies according to the present invention may include without limitation lipids listed in table 20 and 21 below. All used abbreviations for lipids refer primarily to standard use in the literature and are included in table 20 as a helpful reference.

In one embodiment of the invention the lipid assemblies include one or more neutral lipids selected from the group comprising natural or synthetic phosphatidylcholines, phosphatidylethanolamines, sphingolipids, ceramides, cerebrosides, sterol-based lipids, e.g. cholesterol, and derivatives of such lipids. Specific examples of neutral lipids include, without limited to DMPC, DPPC, DSPC, POPC, DOPC, egg yolk PC, soya PC, DMPE, DPPE, DSPE, POPE, DOPE, Diphytanoyl-PE, sphingomyelein, ceramide and cholesterol.

In another embodiment the lipid assemblies include one or more cationic lipids, alone or in combination with neutral and/or anionic lipids. The cationic lipids may include without limitation DOTAP, DMTAP, DPTAP, DC-Chol, DAC-Chol, DODAP, DOEPC, TC-Chol, DOTMA, DORIE, DDAP, CTAB, CPyC, DPIM, CHIM, MoChol, HisChol, BGSC, BGTC, DOSPER, DOSC, DOGSDO, DmC4Mo2, DmC3Mo2, C3Mo2, C3Mo3, C4Mo4, C5Mo2, C6Mo2, C8Mo2, PipC2Chol, MoC2Chol, MoC3Chol, N-methyl-PipChol, PyrroC2Chol, PyC2Chol, ImC3Chol, PipeC2Chol and derivatives thereof.

In still another embodiment of the present invention the lipid assemblies include one or more anionic lipids, alone or in combination with neutral and/or cationic lipids. The anionic lipids may include, without limitation, phosphatidylglycerols, phosphatidylserins, phosphatidylinositols, phosphatidic acids, CHEMS and further anionic sterol-derivatives, cetylphosphate, diacylglycerol hemisuccinates and cardiolipines and derivatives thereof. Specific examples include without limited to DMPG, DPPG, DSPG, DOPG, POPG, DMPS, DPPS, DOPS, POPS, DMPA, DPPA, DOPA, POPA, CHEMS, cetylphosphate, DMG-Succ, DPG-Succ, DSG-Succ, DOG-Succ, POG-Succ, Chol-Sulfate, Chol-Phospate.

In one aspect, lipid assemblies for use with the present invention may include fusogenic lipids, such as for example DOPE, lysolipids or free fatty acids or mixtures of said fusogenic lipids with neutral and/or cationic and/or anionic lipids mentioned above.

Surprisingly it has been found that the impact of lipids comprising TEE's on the fusability of lipid assemblies may vary and as shown in example 14 depends on the neutral lipids used for formation of the lipid assemblies.

In one embodiment of the invention liposomes comprising one or more lipids with one or more TEE's are formed from a mixture of the neutral lipids selected from the group phosphatidylcholines, sphingomyleins, ceramides or cerebrosides or mixtures thereof and cholesterol or phosphatidylethanolamines or mixtures thereof whereas the molar ratio of the mixture is between 1:3 and 3:1, preferred between 1:2 and 2:1. In one aspect of this embodiment the lipid assemblies may further comprise anionic, cationic or amphoteric lipids or mixtures thereof. However, the presence of charged lipids is not mandatory.

In another aspect of this embodiment mixtures of phosphatidylcholines and cholesterol or mixtures of phosphatidylcholines and phosphatidylethanolamines are preferred. More preferred are compositions comprising one or more of the phosphatidylcholines selected from DSPC, DPPC, DMPC, POPC or DOPC in combination with one or more lipids selected from the group of DOPE or cholesterol.

In another aspect of this embodiment these lipid assemblies may be used to efficiently transfect cells.

Of course, lipid assemblies known in the art can be used with lipids comprising TEE's of the current invention. Some of such lipid assemblies are disclosed for example in WO 05/105152; WO 06/069782; Morrissey et al., Nature Biotechnology, 23(8), 1002-1007, 2005; WO 05/007196; Wheeler et al., Gene Therapy, 6(2), 271-281, 1999; WO 02/34236; Budker et al., Nature Biotechnology, 14(6), 760-764, 1996; U.S. Pat. No. 5,965,434; U.S. Pat. No. 5,635,487; Spagnou et al., Biochemistry, 43(42), 13348-13356, 2004; U.S. Pat. No. 6,756,054; WO 06/016097 and U.S. Pat. No. 5,785,992; WO 04/035523.

Alternatively, the lipid assemblies comprising one or more lipids with one or more transfection enhancer elements may be formed from a lipid phase having an amphoteric character. In one aspect said lipid assemblies are amphoteric liposomes. Amphoteric liposomes represent a recently described class of liposomes having anionic or neutral charge at about pH 7.5 and cationic charge at pH 4. WO 02/066490, WO 02/066012 and WO 03/070220 give a detailed description of amphoteric liposomes and suitable lipids therefor.

By "amphoteric" herein is meant a substance, a mixture of substances or a supra-molecular complex (e.g., a liposome) comprising charged groups of both anionic and cationic character wherein:
(i) at least one of the charged groups has a pK between 4 and 8,
(ii) the cationic charge prevails at pH 4, and
(iii) the anionic charge prevails at pH 8,
resulting in an isoelectric point of neutral net charge between pH 4 and pH 8. Amphoteric character is by this definition different from zwitterionic character, as zwitterions do not have a pK in the range mentioned above. In consequence, zwitterions are essentially neutrally charged over a range of pH values; phosphatidylcholines and phosphatidylethanolamines are neutral lipids with zwitterionic character.

In some embodiments of the present invention, said amphoteric liposomes may be formed from a lipid phase comprising one or more amphoteric lipids.

Suitable amphoteric lipids are disclosed in WO 02/066489 and WO 03/070735. Preferably, said amphoteric lipid is selected from the group consisting of HistChol, HistDG, iso-HistSuccDG, Acylcarnosin, HCChol, Hist-PS and EDTA-Chol.

In yet another embodiment the lipid phase may comprise a plurality of charged amphiphiles which in combination with one another have amphoteric character.

In one aspect of this embodiment said one or more charged amphiphiles comprise a pH sensitive anionic lipid and a pH sensitive cationic lipid. Herein, such a combination of a chargeable cation and chargeable anion is referred to as an "amphoteric II" lipid pair. Suitably, said chargeable cations have pKa values of between about 4 and about 8, preferably of between about 5.5 and about 7.5.

Suitably, said chargeable anions have pKa values of between about 3.5 and about 7, preferably of between about 4 and about 6.5. Examples include, but are not limited to MoChol/CHEMS, DPIM/CHEMS and DPIM/DGSucc.

In a second aspect of this embodiment said one or more charged amphiphiles comprise a stable cation and a chargeable anion and is referred to as "amphoteric I" lipid pair.

Examples include, without limited to DDAB/CHEMS, DOTAP/CHEMS, DC-Chol/CHEMS and DOTAP/DMG-Succ, DODAP/Chems, DODAP/DMGSucc. Further examples can include DC-Chol/Chol-C3, DC-Chol/Chol-C5, DC-Chol/Chol-C6 or DC-Chol/Chol-C8 or similar compositions using DDAB, DODAP, or DOTAP as cations.

In a third aspect of this embodiment said one or more charged amphiphiles comprise a stable anion and a chargeable cation and is referred to as "amphoteric III" lipid pair. Examples include, but not limited to MoChol/DOPG and MoChol/Chol-SO4.

It is of course possible to use amphiphiles with multiple charges such as amphipathic dicarboxylic acids, phosphatidic acid, amphipathic piperazine derivatives and the like. Such multicharged amphiphiles might fall into pH sensitive amphiphiles or stable anions or cations or might have mixed character.

The amount of lipids containing said transfection enhancer elements is preferably between 0.1% and 90% of the total lipid phase of the lipid assemblies or liposomes. In one embodiment the amount of lipids containing said transfection enhancer elements is between 1% and 50% of the total lipid phase. In another embodiment the amount of said of lipids containing said transfection enhancer elements is between 2% and 20% of the total lipid phase of the lipid assemblies or liposomes.

Specific examples of liposomes in accordance with the present invention include, but are not limited to:

| Lipid 1 | Lipid 2 | Lipid 3 | Lipid 4 | TEE-Lipid | Mol % |
|---------|---------|---------|---------|-----------|-------|
| POPC | DOPE | | | Pal-PE or Deca-PE or w12-PE or w21-PE or w12-DPTAP or w16-DPTAP or w20-DPTAP or w12-Amid-PE or w16-Amid-PE | 22:68:10 |
| POPC | DOPE | | | Pal-PE or Deca-PE or w12-PE or w21-PE or w12-DPTAP or w16-DPTAP or w20-DPTAP or w12-Amid-PE or w16-Amid-PE | 17:53:30 |
| POPC | | DOTAP | Chems | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DOTAP | Chems | Pal-PE or Deca-PE or w12-PE or w21-PE or w12-DPTAP or w16-DPTAP or w20-DPTAP or w12-Amid-PE or w16-Amid-PE | 50:10:30:10 |
| POPC | DOPE | MoChol | Chems | Pal-PE or Deca-PE or w12-PE or w21-PE or w12-DPTAP or w16-DPTAP or w20-DPTAP or w12-Amid-PE or w16-Amid-PE | 12:38:20:20:10 |
| POPC | DOPE | MoChol | Chems | Pal-PE or Deca-PE or w12-PE or w21-PE or w12-DPTAP or w16-DPTAP or w20-DPTAP or w12-Amid-PE or w16-Amid-PE | 5:22:42:21:10 |
| POPC | DOPE | MoChol | DOG-Succ | Pal-PE or Deca-PE or w12-PE or w21-PE or w12-DPTAP or w16-DPTAP or w20-DPTAP or w12-Amid-PE or w16-Amid-PE | 7:20:21:42:10 |
| POPC | DOPE | MoChol | DMG-Succ | Pal-PE or Deca-PE or w12-PE or w21-PE or w12-DPTAP or w16-DPTAP or w20-DPTAP or w12-Amid-PE or w16-Amid-PE | 5:22:21:42:10 |
| | DOPE | MoChol | Chems | Pal-PE or Deca-PE or w12-PE or w21-PE or w12-DPTAP or w16-DPTAP or w20-DPTAP or w12-Amid-PE or w16-Amid-PE | 50:20:20:10 |
| POPC | | DDAB | Chems | Pal-PE or Deca-PE or w12-PE or w21-PE or w12-DPTAP or w16-DPTAP or w20-DPTAP or w12-Amid-PE or w16-Amid-PE | 15:28:47:10 |

-continued

| Lipid 1 | Lipid 2 | Lipid 3 | Lipid 4 | TEE-Lipid | Mol % |
|---|---|---|---|---|---|
| POPC | | DDAB | Chol-C3 | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DDAB | Chol-C5 | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DDAB | Chol-C6 | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DDAB | Chol-C8 | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DC-Chol | DMGSucc | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DC-Chol | Chol-C3 | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DC-Chol | Chol-C5 | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DC-Chol | Chol-C6 | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DC-Chol | Chol-C8 | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DC-Chol | Chems | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DODAP | DMGSucc | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DODAP | Chol-C3 | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DODAP | Chol-C5 | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DODAP | Chol-C6 | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DODAP | Chol-C8 | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DODAP | Chems | Pal-PE or Deca-PE or w12-PE or w21-PE or w12-DPTAP or w16-DPTAP or w20-DPTAP or w12-Amid-PE or w16-Amid-PE | 15:28:47:10 |
| Lig-Ly PC | | DOTAP | Chems | Pal-PE or Deca-PE or w12-PE or w21-PE or w12-DPTAP or w16-DPTAP or w20-DPTAP or w12-Amid-PE or w16-Amid-PE | 15:28:47:10 |
| C6-Cer | | DOTAP | Chems | Pal-PE or Deca-PE or w12-PE or w21-PE or w12-DPTAP or w16-DPTAP or w20-DPTAP or w12-Amid-PE or w16-Amid-PE | 15:28:47:10 |

-continued

| Lipid 1 | Lipid 2 | Lipid 3 | Lipid 4 | TEE-Lipid | Mol % |
|---|---|---|---|---|---|
| SM | | DC-Chol | Chems | Pal-PE or Deca-PE or w12-PE or w21-PE or w12-DPTAP or w16-DPTAP or w20-DPTAP or w12-Amid-PE or w16-Amid-PE | 15:28:47:10 |
| POPC | | DOTAP | Chems | Pal-PE or Deca-PE or w12-PE or w21-PE or w12-DPTAP or w16-DPTAP or w20-DPTAP or w12-Amid-PE or w16-Amid-PE | 15:28:47:10 |

In one embodiment of the invention the lipid phase of the lipid assemblies comprises about 10-20 mol % of a phosphatidylcholine, 20-35 mol % of DC-Chol, 40-60 mol % of CHEMS or DMGSucc and about 5-15 mol % of Pal-PE or Deca-PE. In a specific embodiment said assemblies are liposomes.

In one embodiment of the invention the lipid phase of the lipid assemblies comprises between 20 and 90 mol %, preferred between 40 and 80 mol % of an amphoteric lipid mixture, between 2 and 20 mol %, preferred between 5 and 10 mol % of one or more lipids with one or more TEE's and if needed an appropriate amount of neutral or zwitterionic lipids, selected from one or more of phosphatidylcholines, sphingolipids, phosphatidylethanolamines or cholesterol. Preferably said lipids with one or more TEE's are selected from the group Deca-PE, w12-PE, Pal-PE, w21-PE, w12-DPTAP, w16-DPTAP, w20-DPTAP, w12-Amid-PE or w16-Amid-PE.

In one aspect of this embodiment said amphoteric lipid mixture is an "amphoteric I" lipid pair wherein the molar ratio cationic lipids to anionic lipids (C/A ratio) is preferably between 0.3 and 0.7. Preferably said cationic lipids are selected from one or more of DOTAP, DODAP, DDAB, DC-Chol, DAC-Chol or TC-Chol and said anionic lipids are selected from one or more of Chems, DMG-Succ or DOG-Succ. More preferred said "amphoteric I" lipid pairs are selected from one of the following combinations: DOTAP/Chems, DOTAP/DMG-Succ, DOTAP/DOG-Succ, DODAP/Chems, DODAP/DMG-Succ, DODAP/DOG-Succ, DDAB/Chems, DDAB/DMG-Succ, DDAB/DOG-Succ, DC-Chol/Chems, DC-Chol/DMG-Succ, DC-Chol/DOG-Succ, DAC-Chol/Chems, DAC-Chol/DMG-Succ, DAC-Chol/DOG-Succ, TC-Chol/Chems, TC-Chol/DMG-Succ, TC-Chol/DOG-Succ.

In a second aspect of this embodiment said amphoteric lipid mixture is an "amphoteric II" lipid pair wherein the molar ratio cationic lipids to anionic lipids (C/A ratio) is preferably between 0.3 and 3. Preferably said cationic lipids are selected from one or more of MoChol, HisChol, Chim, DmC4Mo2 and said anionic lipids are selected from one or more of Chems, DMG-Succ or DOG-Succ. More preferred said "amphoteric II" lipid pairs are selected from one of the following combinations: MoChol/Chems, MoChol/DMG-Succ, HisChol/DOG-Succ, HisChol/Chems, HisChol/DMG-Succ, HisChol/DOG-Succ, Chim/Chems, Chim/DMG-Succ, Chim/DOG-Succ, DmC4Mo2/Chems, DmC4Mo2/DMG-Succ, DmC4Mo2/DOG-Succ.

In a third aspect of this embodiment said lipid assemblies are preferably amphoteric liposomes.

In some embodiments of the invention the lipid assemblies according to the invention may comprise cell targeting ligands on the surface which binds to a target receptor of the cell surface. Ligands may include, but are not limited to, antibodies or their fragments, sugars, hormones, vitamins, peptides, such as arg-gly-asp (RGD), growth factors, bilirubin, transferrin, folate or other components.

The liposomes of the invention may be manufactured using suitable methods that are known to those skilled in the art. Such methods include, but are not limited to, extrusion through membranes of defined pore size, injection of an alcoholic lipid solution into a water phase containing the cargo to be encapsulated, or high pressure homogenisation.

A solution of the drug (e.g. an oligonucleotide) may be contacted with the lipid phase at a neutral pH, thereby resulting in volume inclusion of a certain percentage of the solution. High concentrations of the lipids, ranging from about 50 mM to about 150 mM, are preferred to achieve substantial encapsulation of the active agent.

Amphoteric liposomes offer the distinct advantage of binding nucleic acids at or below their isoelectric point, thereby concentrating these active agents at the liposome membrane. This process, called advanced loading procedure, is described in more detail in WO 02/066012.

In one embodiment of the invention amphoteric liposomes comprising one or more lipids with one or more transfection enhancer elements may be prepared by using said advanced loading procedure combined with a lipid film extrusion process. Briefly, lipids are dissolved in an organic solvent and a lipid film is produced by evaporating the solvent to dryness. The lipid film is hydrated with an aqueous phase having a pH <6, preferred between 3 and 5.5, containing for example a nucleic acid. The multilamellar liposome suspension is subsequently extruded through membranes (e.g. polycarbonate) with defined pore size. Afterwards the pH of the suspension is increased to >7.

In another embodiment of the invention amphoteric liposomes comprising one or more lipids with one or more transfection enhancer elements may be prepared by using said advanced loading procedure combined with an injection of an alcoholic lipid solution into a water phase containing for example a nucleic acid. This process may comprise several steps:

a) Providing a solution of a lipid mixture in a water-miscible solvent, preferably an alcohol, wherein said solution may be optionally acidified b) Providing an aqueous solution of a nucleic acid drug, wherein said solution may be optionally acidified At least one of the solutions in a) and b) must be acidified to a pH <6, preferably a pH between 3 and 5.5.

c) Mix of defined amounts of the solutions of a) and b) by injecting the alcoholic solution of the lipid mixture into the aqueous solution of the nucleic acid or vice versa or by combining two controlled flows of the solutions of a) and b), optional using one or more mixing devices.

d) Dilution step, which is optional e) Dissolve of the interactions between the amphoteric liposomes and the nucleic acids by increasing the pH to higher than 7 or by increasing the ionic strange and subsequent increasing of the pH to higher than 7.

f) Removing of non-encapsulated drug and/or concentrating the liposomal suspension and or changing the aqueous phase and/or removing the water miscible solvent, wherein each of these steps is independently optional.

g) Sterile filtration of the liposomes, which is optional

Between the steps c) and d) and/or between d) and e) and/or between e) and f) and/or between f) and g) an extrusion of the liposomes may be part of the process.

Between the steps e) and f) and/or between f) and g) one or more freeze/thaw cycles of the liposomes may be part of the process.

After step g) one or more freeze/thaw cycles and/or a lyophilisation of the liposomes may be part of the process.

Preferably, said alcohol may be selected from, without limited to, ethanol, propanol or isopropanol, optionally acidified using a buffer or an acid.

The pH of the acidic solutions used in the advanced loading procedure may be adjusted with known buffer substances like acetate-buffer or citrate-buffer. Alternatively, the pH may be adjusted using an acid (e.g. HCl, acetic acid or citric acid). Preferably, pharmaceutical acceptable buffers, like acetic acid, citric acid or glycine are used.

Irrespective of the actual production process used to make the liposomes of the invention, in some embodiments, non-encapsulated drug may be removed from the liposomes after the initial production step in which the liposomes are formed as tight containers. Again, the technical literature and the references included herein describe such methodology in detail and suitable process steps may include, but are not limited to, size exclusion chromatography, sedimentation, dialysis, ultrafiltration and diafiltration.

However, the removal of any non-encapsulated drug is not required for performance of the invention, and in some embodiments the liposomal composition may comprise free as well as entrapped drug.

The liposomes according to the present invention may be unilamellar, oligolamellar or multilamellar.

In one aspect of the invention the size of the liposomes may vary between 50 and 1000 nm, preferably between 50 and 500 nm and more preferred between 70 and 250 nm.

In other aspects the size of the liposomes may vary between 70 and 150 nm and in still other aspects the size of the liposomes may vary between 130 and 250 nm.

TABLE 20

Abbreviations for lipids refer primarily to standard use in the literature and are included here as a helpful reference:

| | |
|---|---|
| DMPC | Dimyristoylphosphatidylcholine |
| DPPC | Dipalmitoylphosphatidylcholine |
| DSPC | Distearoylphosphatidylcholine |
| POPC | Palmitoyl-oleoylphosphatidylcholine |
| DOPC | Dioleoylphosphatidylcholine |
| Lig-Ly PC | 1-Lignoceroyl-2-Hydroxy-sn-Glycero-3-Phosphocholine |
| C6-Cer | N-Hexanoyl-D-erythro-Sphingosine |
| SM | Sphingomyeline |
| DOPE | Dioleoylphosphatidylethanolamine |
| DMPE | Dimyristoylphosphatidylethanolamine |
| DPPE | Dipalmitoylphosphatidylethanolamine |
| Diphytanoly-PE | Diphytanolyphosphatidylethanolamine |
| DOPG | Dioleoylphosphatidylglycerol |
| POPG | Palmitoyl-oleoylphosphatidylglycerol |
| DMPG | Dimyristoylphosphatidylglycerol |
| DPPG | Dipalmitoylphosphatidylglycerol |
| DMPS | Dimyristoylphosphatidylserine |
| DPPS | Dipalmitoylphosphatidylserine |

TABLE 20-continued

Abbreviations for lipids refer primarily to standard use in the literature and are included here as a helpful reference:

| | |
|---|---|
| DOPS | Dioleoylphosphatidylserine |
| POPS | Palmitoyl-oleoylphosphatidylserine |
| DMPA | Dimyristoylphosphatidic acid |
| DPPA | Dipalmitoylphosphatidic acid |
| DOPA | Dioleoylphosphatidic acid |
| POPA | Palmitoyl-oleoylphosphatidic acid |
| DMPI | Dimyristoylphosphatidylinositol |
| DPPI | Dipalmitoylphosphatidylinositol |
| DOPI | Dioleoylphosphatidylinositol |
| POPI | Palmitoyl-oleoylphosphatidylinositol |
| Chol | Cholesterol |
| CHEMS | Cholesterolhemisuccinate |
| Chol-C3 | Cholesterolhemimalonate |
| Chol-05 | Cholesterolhemiglutarate |
| Chol-C6 | Cholesterolhemiadipate |
| Chol-C8 | Cholesterolhemisuberate |
| Chol-Sulfate | Cholesterolsulfate |
| Chol-Phosphate | Cholesterolphosphate |
| DC-Chol | 3-β-[N-(N',N'-dimethylethane) carbamoyl]cholesterol |
| Cet-P | Cetylphosphate |
| DODAP | (1,2)-dioleoyloxypropyl)-N,N-dimethylammonium chloride |
| DOEPC | 1,2-dioleoyl-sn-glycero-3-ethylphosphocholine |
| DAC-Chol | 3-β-[N-(N,N'-dimethylethane) carbamoyl]cholesterol |
| TC-Chol | 3-β-[N-(N',N', N'-trimethylaminoethane) carbamoyl] cholesterol |
| DOTMA | (1,2-dioleyloxypropyl)-N,N,N-trimethylammonium-chloride)(Lipofectin ®) |
| DOGS | ((C18)2GlySper3+) N,N-dioctadecylamido-glycyl-spermine (Transfectam ®) |
| CTAB | Cetyl-trimethylammoniumbromide |
| CPyC | Cetyl-pyridiniumchloride |
| DOTAP | (1,2-dioleoyloxypropyl)-N,N,N-trimethylammonium salt |
| DMTAP | (1,2-dimyristoyloxypropyl)-N,N,N-trimethylammonium salt |
| DPTAP | (1,2-dipalmitoyloxypropyl)-N,N,N-trimethylammonium salt |
| DOTMA | (1,2-dioleyloxypropyl)-N,N,N-trimethylammonium chloride) |
| DORIE | (1,2-dioleyloxypropyl)-3 dimethylhydroxyethyl ammoniumbromide) |
| DDAB | Dimethyldioctadecylammonium bromide |
| DPIM | 4-(2,3-bis-palmitoyloxy-propyl)-1-methyl-1H-imidazole |
| CHIM | Histaminyl-Cholesterolcarbamate |
| MoChol | 4-(2-Aminoethyl)-Morpholino-Cholesterolhemisuccinate |
| DmC4Mo2 | 4-(2-Aminoethyl)-Morpholino-Cholesterol-2,3-dimethylhemisuccinate |
| DmC3Mo2 | 4-(2-Aminoethyl)-Morpholino-Cholesterol-2,2-dimethylhemimalonate |
| C3Mo2 | 4-(2-Aminoethyl)-Morpholino-Cholesterolhemimalonate |
| C3Mo3 | 4-(2-Aminopropyl)-Morpholino-Cholesterol-hemimalonate |
| C4Mo4 | 4-(2-Aminobutyl)-Morpholino-Cholesterol-hemisuccinate |
| C5Mo2 | 4-(2-Aminoethyl)-Morpholino-Cholesterol-hemiglutarate |
| C6Mo2 | 4-(2-Aminoethyl)-Morpholino-Cholesterol-hemiadipate |
| C8Mo2 | 4-(2-Aminoethyl)-Morpholino-Cholesterol-hemiadipate |
| PipC2Chol | 4{N-2-ethylamino[(3'-β-cholesteryl) carbamoyl]}piperazine |
| MoC2Chol | {N-2-ethylamino[(3'-β-cholesteryl) carbamoyl]}morpholine |
| MoC3Chol | {N-2-propylamino[(3'-β-cholesteryl) carbamoyl]}morpholine |
| N-methyl-PipChol | N-methyl{4-N-amino[(3'-β-cholesteryl) carbamoyl]}piperazine |

TABLE 20-continued

Abbreviations for lipids refer primarily to standard use in the literature and are included here as a helpful reference:

| | |
|---|---|
| PyrroC2Chol | {N-2-ethylamino[(3'-β-cholesteryl)carbamoyl]}pyrrolidine |
| PipeC2Chol | {N-2-ethylamino[(3'-β-cholesteryl)carbamoyl]}piperidine |
| ImC3Chol | {N-2-propylamino[(3'-β-cholesteryl)carbamoyl]}imidazole |
| PyC2Chol | {N-2-ethylamino[(3'-β-cholesteryl)carbamoyl]}pyridine |
| HisChol | Histaminyl-Cholesterolhemisuccinate |
| HCChol | Nα-Histidinyl-Cholesterolcarbamate |
| HistChol | Nα-Histidinyl-Cholesterol-hemisuccinate |
| AC | Acylcarnosine, Stearyl- & Palmitoylcarnosine |
| HistDG | 1,2—Dipalmitoylglycerol-hemisuccinat-N_-Histidinyl-hemisuccinate, & Distearoyl-, Dimyristoyl, Dioleoyl or palmitoyl-oleoylderivatives |
| IsoHistSuccDG | 1,2-ipalmitoylglycerol-O_-Histidinyl-Nα-hemisuccinat, & Distearoyl-, Dimyristoyl, Dioleoyl or palmitoyl-oleoylderivatives |
| DGSucc | 1,2—Dipalmitoylglycerol-3-hemisuccinate & Distearoyl-, dimyristoyl- Dioleoyl or palmitoyl-oleoylderivatives |
| EDTA-Chol | cholesterol ester of ethylenediaminetetraacetic acid |
| Hist-PS | Nα-histidinyl-phosphatidylserine |
| BGSC | bisguanidinium-spermidine-cholesterol |
| BGTC | bisguanidinium-tren-cholesterol |
| DOSPER | (1.3-dioleoyloxy-2-(6-carboxy-spermyl)-propylamide |
| DOSC | (1,2-dioleoyl-3-succinyl-sn-glyceryl choline ester) |
| DOGSDO | (1,2-dioleoyl-sn-glycero-3-succinyl-2-hydroxyethyl disulfide ornithine) |
| DOGSucc or DOGS | 1,2-Dioleoylglycerol-3-hemisucinate |
| POGSucc or POGS | Palmitolyl-oleoylglycerol-oleoyl-3-hemisuccinate |
| DMGSucc or DMGS | 1,2-Dimyristoylglycerol-3-hemisuccinate |
| DPGSucc or DPGS | 1,2-Dipalmitoylglycerol-3-hemisuccinate |
| DOGM | Dioleoylglycerolhemimalonate |
| DOGG | Dioleoylglycerolhemiglutarate |
| DOGA | Dioleoylglycerolhemiadipate |
| DMGM | Dimyristoylglycerolhemimalonate |
| DMGG | Dimyristoylglycerolhemiglutarate |
| DMGA | Dimyristoylglycerolhemiadipate |
| DOAS | 4-{(1,2-Dioleoyl-ethyl)amino}-4-oxobutanoic acid |
| DOAM | 4-{(1,2-Dioleoyl-ethyl)amino}-4-oxopropanoic acid |
| DOAG | 4-{(1,2-Dioleoyl-ethyl)amino}-4-oxopentanoic acid |
| DOAA | 4-{(1,2-Dioleoyl-ethyl)amino}-4-oxohexanoic acid |
| DMAS | 4-{(1,2-Dimyristoyl-ethyl)amino}-4-oxobutanoic acid |
| DMAM | 4-{(1,2-Dimyristoyl-ethyl)amino}-4-oxopropanoic acid |
| DMAG | 4-{(1,2-Dimyristoyl-ethyl)amino}-4-oxopentanoic acid |
| DMAA | 4-{(1,2-Dimyristoyl-ethyl)amino}-4-oxohexanoic acid |
| DOS | 5,6-Dioleoyl-hexanoic acid |
| DOM | 4,5-Dioleoyl-pentanoic acid |
| DOG | 6,7-Dioleoyl-heptanoic acid |
| DOA | 7,8-Dioleoyl-octanoic acid |
| DMS | 5,6-Dimyristoyl-hexanoic acid |
| DMM | 4,5-Dimyristoyl-pentanoic acid |
| DMG | 6,7-Dimyristoyl-heptanoic acid |
| DMA | 7,8-Dioleoyl-octanoic acid |
| Pal-PE or w16-PE | 16-{2-[2,3-Bis-hexadecanoyloxy-propoxy)-hydroxy-phosphoryl-oxy]-ethylamino}-hexadecanoic acid |
| Deca-PE or w10-PE | 10-{2-[2,3-Bis-hexadecanoyloxy-propoxy)-hydroxy-phosphoryloxy]-ethylamino}-decanoic acid |
| w6-PE | 6-{2-[2,3-Bis-hexadecanoyloxy-propoxy)-hydroxy-phosphoryl-oxyl-ethylamino}-hexanoic acid |
| w12-PE | 12-{2-[2,3-Bis-hexadecanoyloxy-propoxy)-hydroxy-phosphoryl-oxyl-ethylamino}-dodecanoic acid |
| w21-PE | 21-{2-[2,3-Bis-hexadecanoyloxy-propoxy)-hydroxy-phosphoryl-oxyl-ethylamino}-henicosanoic acid |
| w6-DPATP | Hexadecanoic acid 1- {[(5-carboxy-pentyl)-dimethyl-ammonium] methyl-2-hexadecanoyloxy-ethyl ester |
| w12-DPTAP | Hexadecanoic acid 1- {[(11-carboxy-undecyl)-dimethyl-ammonium] methyl-2-hexadecanoyloxy-ethyl ester |
| w16-DPTAP | Hexadecanoic acid 1- {[(15-carboxy-pentadecyl)-dimethyl-ammonium] methyl-2-hexadecanoyloxy-ethyl ester |
| w20-DPTAP | Hexadecanoic acid 1- {[(19-carboxy-nonadecyl)-dimethyl-ammonium] methyl-2-hexadecanoyloxy-ethyl ester |
| w16-Amid-PE | Hexadecanoic acid 3- {[2-(15-carboxy-pentadecanoylamino)-ethoxy]-hydroxy-phosphoryloxy }-2-hexadecanoyloxy-propyl ester |
| w5-Amid-PE | Hexadecanoic acid 3-{[2-(4-carboxy-butanoylamino)-ethoxy]-hydroxy-phosphoryloxy}-2-hexadecanoyloxy-propyl ester |
| w12-Amid-PE | Hexadecanoic acid 3-{[2-(11-carboxy-undecanoylamino)-ethoxy]-hydroxy-phosphoryloxy}-2-hexadecanoyloxy-propyl ester |
| C6-PE | Hexadeanoic acid 2-hexadecanoloxy-3-[(2-hexanoylamino-ethoxy)-hydroxy-phosphoryloxy]-propyl ester |
| C12-PE | Hexadeanoic acid 2-hexadecanoloxy-3-[(2-dodecanoylamino-ethoxy)-hydroxy-phosphoryloxy]-propyl ester |
| C16-PE | Hexadeanoic acid 2-hexadecanoloxy-3-[(2-hexadecanoylamino-ethoxy)-hydroxy-phosphoryloxy]-propyl ester |
| C20-PE | Hexadeanoic acid 2-hexadecanoloxy-3-[(2-eicosanoylamino-ethoxy)-hydroxy-phosphoryloxy]-propyl ester |
| NBD-PE | N-(7-nitrobenz-2-oxa-1,3-diazol- 4-yl)-1,2-dihexadecanoyl-sn- glycero-3-phosphoethanolamine, triethylammonium salt |
| Rhodamine-PE | Lissamine ™ rhodamine B 1,2-dihexadecanoyl-sn-glycero-3-phosphoethanolamine, triethylammonium salt |

TABLE 21
Non-limiting examples of lipids that are suitable for use in the compositions in accordance with the present invention. The membrane anchors of the lipids are shown exemplarily and serve only to illustrate the lipids of the invention and are not intended to limit the same.
MoChol
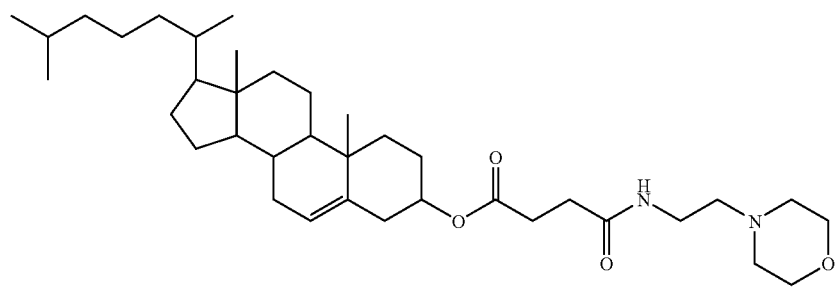
DG-Succ
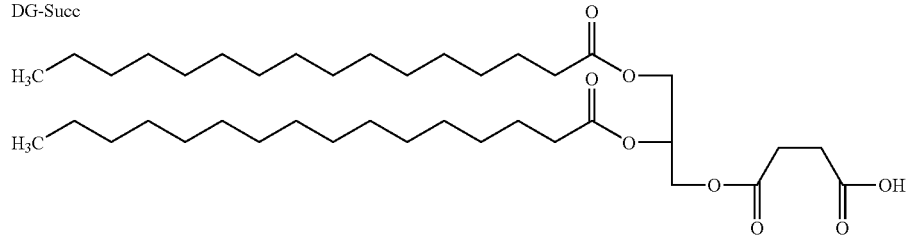
DOTAP
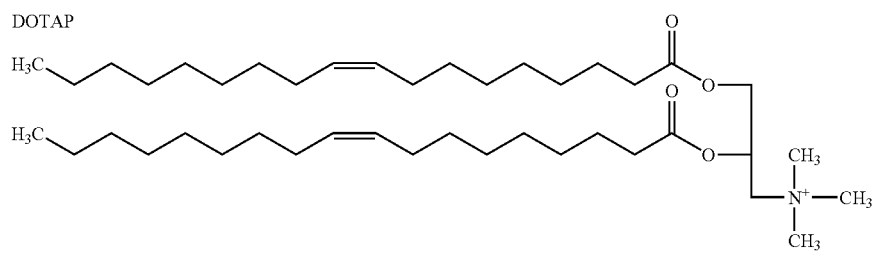
IsohistsuccDG
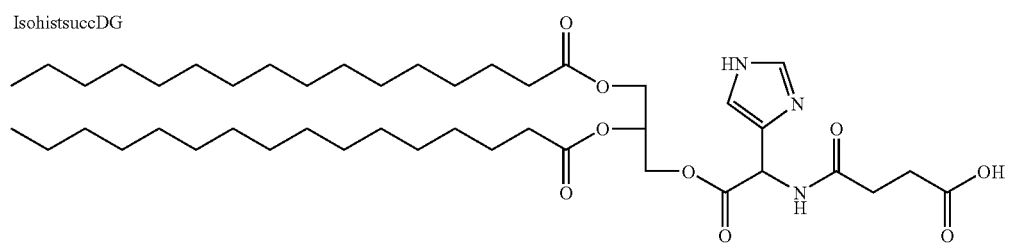
HisChol
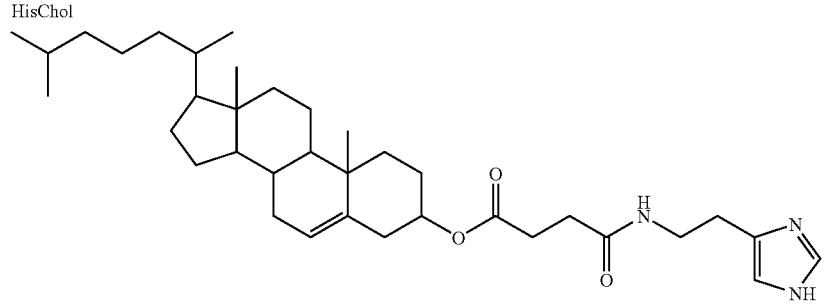

TABLE 21-continued

Non-limiting examples of lipids that are suitable for use in the compositions in accordance with the present invention. The membrane anchors of the lipids are shown exemplarily and serve only to illustrate the lipids of the invention and are not intended to limit the same.

HCChol

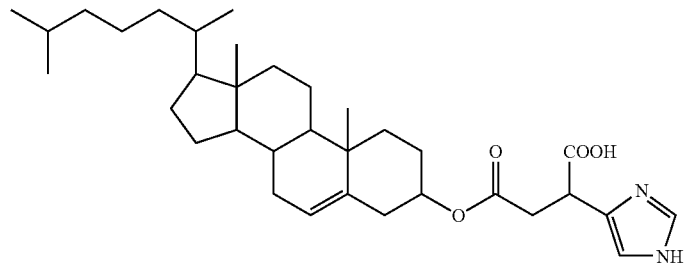

AC

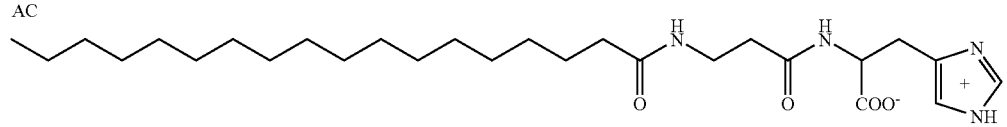

Hist-Chol

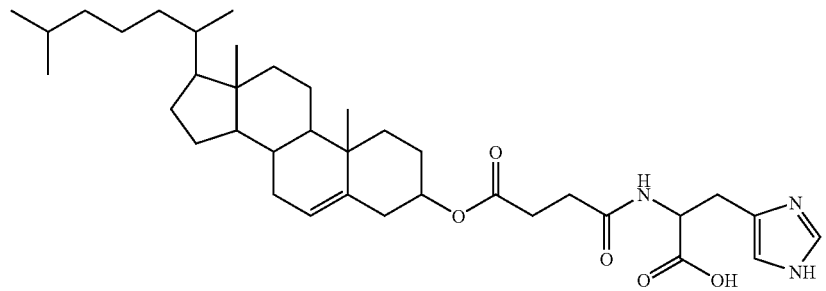

Hist-DG

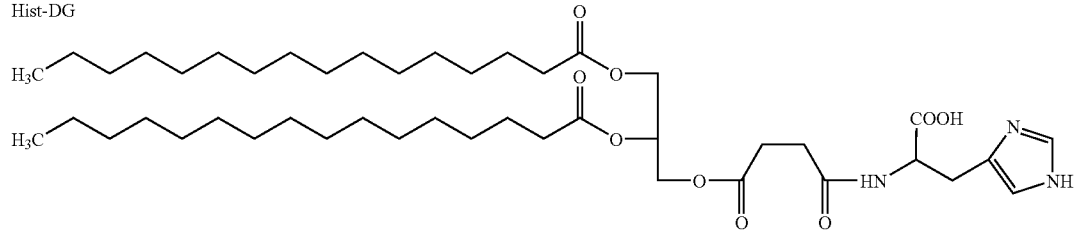

Transfection

According to the present invention lipid assemblies comprising lipids with a transfection enhancer element may be used to transfect cells in vitro, in vivo or ex vivo. Without being limited to such use, the lipid assemblies (e.g. the liposomes) described in the present invention are well suited for use as carriers for nucleic acid-based drugs such for example as oligonucleotides, polynucleotides and DNA plasmids. These drugs are classified into nucleic acids that encode one or more specific sequences for proteins, polypeptides or RNAs and into oligonucleotides that can specifically regulate protein expression levels or affect the protein structure through inter alia interference with splicing and artificial truncation.

In some embodiments of the present invention, therefore, the nucleic acid-based therapeutic may comprise a nucleic acid that is capable of being transcribed in a vertebrate cell into one or more RNAs, which RNAs may be mRNAs, shRNAs, miRNAs or ribozymes, wherein such mRNAs code for one or more proteins or polypeptides. Such nucleic acid therapeutics may be circular DNA plasmids, linear DNA constructs, like MIDGE vectors (Minimalistic Immunogenically Defined Gene Expression) as disclosed in WO 98/21322 or DE 19753182, or mRNAs ready for translation (e.g., EP 1392341).

In another embodiment of the invention, oligonucleotides may be used that can target existing intracellular nucleic acids or proteins. Said nucleic acids may code for a specific gene, such that said oligonucleotide is adapted to attenuate or modulate transcription, modify the processing of the transcript or otherwise interfere with the expression of the protein. The term "target nucleic acid" encompasses DNA encoding a specific gene, as well as all RNAs derived from such DNA, being pre-mRNA or mRNA. A specific hybridisation between the target nucleic acid and one or more oligonucleotides directed against such sequences may result in an inhibition or modulation of protein expression. To achieve such specific targeting, the oligonucleotide should suitably comprise a continuous stretch of nucleotides that is substantially complementary to the sequence of the target nucleic acid.

Oligonucleotides fulfilling the abovementioned criteria may be built with a number of different chemistries and topologies. The oligonucleotides may comprise naturally occurring or modified nucleosides comprising but not limited to DNA, RNA, locked nucleic acids (LNA's), 2'O-methyl RNA (2'Ome), 2' O-methoxyethyl RNA (2'MOE) in their phosphate or phosphothioate forms or Morpholinos or peptide nucleic acids (PNA's).

Oligonucleotides may be single stranded or double stranded.

Oligonucleotides are polyanionic structures having 8-60 charges. In most cases these structures are polymers comprising nucleotides. The present invention is not limited to a particular mechanism of action of the oligonucleotides and an understanding of the mechanism is not necessary to practice the present invention.

The mechanisms of action of oligonucleotides may vary and might comprise inter alia effects on splicing, transcription, nuclear-cytoplasmic transport and translation.

In a preferred embodiment of the invention single stranded oligonucleotides may be used, including, but not limited to DNA-based oligonucleotides, locked nucleic acids, 2'-modified oligonucleotides and others, commonly known as antisense oligonucleotides. Backbone or base or sugar modifications may include, but are not limited to, Phosphothioate DNA (PTO), 2'O-methyl RNA (2'Ome), 2'Fluoro RNA (2'F), 2' O— methoxyethyl-RNA (2'MOE), peptide nucleic acids (PNA), N3'-P5' phosphoamidates (NP), 2'fluoroarabino nucleic acids (FANA), locked nucleic acids (LNA), Morpholine phosphoamidate (Morpholino), Cyclohexene nucleic acid (CeNA), tricyclo-DNA (tcDNA) and others. Moreover, mixed chemistries are known in the art, being constructed from more than a single nucleotide species as copolymers, block-copolymers or gapmers or in other arrangements.

In addition to the aforementioned oligonucleotides, protein expression can also be inhibited using double stranded RNA molecules containing the complementary sequence motifs. Such RNA molecules are known as siRNA molecules in the art (e.g., WO 99/32619 or WO 02/055693). Other siRNAs comprise single stranded siRNAs or double stranded siRNAs having one non-continuous strand. Again, various chemistries were adapted to this class of oligonucleotides. Also, DNA/RNA hybrid systems are known in the art.

In another embodiment of the present invention, decoy oligonucleotides can be used. These double stranded DNA molecules and chemical modifications thereof do not target nucleic acids but transcription factors. This means that decoy oligonucleotides bind sequence-specific DNA-binding proteins and interfere with the transcription (e.g., Cho-Chung, et al. in Curr. Opin. Mol. Ther., 1999).

In a further embodiment of the invention oligonucleotides that may influence transcription by hybridizing under physiological conditions to the promoter region of a gene may be used. Again various chemistries may adapt to this class of oligonucleotides.

In a still further alternative of the invention, DNAzymes may be used. DNAzymes are single-stranded oligonucleotides and chemical modifications thereof with enzymatic activity. Typical DNAzymes, known as the "10-23" model, are capable of cleaving single-stranded RNA at specific sites under physiological conditions. The 10-23 model of DNAzymes has a catalytic domain of 15 highly conserved deoxyribonucleotides, flanked by 2 substrate-recognition domains complementary to a target sequence on the RNA. Cleavage of the target mRNAs may result in their destruction and the DNAzymes recycle and cleave multiple substrates.

In yet another embodiment of the invention, ribozymes can be used. Ribozymes are single-stranded oligoribonucleotides and chemical modifications thereof with enzymatic activity. They can be operationally divided into two components, a conserved stem-loop structure forming the catalytic core and flanking sequences which are reverse complementary to sequences surrounding the target site in a given RNA transcript. Flanking sequences may confer specificity and may generally constitute 14-16 nt in total, extending on both sides of the target site selected.

In a still further embodiment of the invention aptamers may be used to target proteins. Aptamers are macromolecules composed of nucleic acids, such as RNA or DNA, and chemical modifications thereof that bind tightly to a specific molecular target and are typically 15-60 nt long. The chain of nucleotides may form intramolecular interactions that fold the molecule into a complex three-dimensional shape. The shape of the aptamer allows it to bind tightly against the surface of its target molecule including but not limited to acidic proteins, basic proteins, membrane proteins, transcription factors and enzymes. Binding of aptamer molecules may influence the function of a target molecule.

All of the above-mentioned oligonucleotides may vary in length between as little as 5, preferably between 8 and 50 nucleotides per strand. More specifically, the oligonucleotides may be antisense oligonucleotides of 8 to 50 nucleotides length that catalyze RNAseH mediated degradation of their target sequence or block translation or re-direct splicing or act as antogomirs; they may be siRNAs of 15 to 30 basepairs length; they may further represent decoy oligonucleotides of 15 to 30 basepairs length; can be complementary oligonucleotides influencing the transcription of genomic DNA of 15 to 30 nucleotides length; they might further represent DNAzymes of 25 to 50 nucleotides length or ribozymes of 25 to 50 nucleotides length or aptamers of 15 to 60 nucleotides length. Such subclasses of oligonucleotides are often functionally defined and can be identical or different or share some, but not all features of their chemical nature or architecture without substantially affecting the teachings of this invention. The fit between the oligonucleotide and the target sequence is preferably perfect with each base of the oligonucleotide forming a base pair with its complementary base on the target nucleic acid over a continuous stretch of the above-mentioned number of oligonucleotides. The pair of sequences may contain one or more mismatches within the said continuous stretch of base pairs, although this is less preferred. In general the type and chemical composition of such nucleic acids is of little impact for the performance of the inventive liposomes as vehicles be it in vivo or in vitro and the skilled artisan may find other types of oligonucleotides or nucleic acids suitable for combination with the inventive lipid assemblies.

In one embodiment of the invention the oligonucleotides are directed against tumor targets. In a preferred embodiment the oligonucleotides are directed against tumor targets selected from the group comprising CEACAM6, BCL-2, EPHA2, CTNNB1, RhoA, PLK1, XIAP, Telomerase, Cyclin D1, K-Ras, EG5, Ki67, androgen receptor, FoxM1, Akt1, VEGF, KSB, CDC25B. Particularly preferred are oligonucleotides directed against PLK1, RhoA, EG5, FoxM1, CDC25B or Ki67.

A further aspect of the invention relates to pharmaceutical compositions comprising lipid assemblies comprising one or more lipids with one or more transfection enhancer elements as a carrier for the targeted delivery of active agents or ingredients, including drugs such as nucleic acid drugs, e.g., oligonucleotides and plasmids. The pharmaceutical composition of the present invention may be formulated in a suitable pharmacologically acceptable vehicle. Vehicles such as water, saline, phosphate buffered saline and the like are well known to those skilled in the art for this purpose.

In some embodiments said pharmaceutical compositions may be used for the treatment or prophylaxis of inflammatory, immune or autoimmune disorders and/or cancer of humans or non-human animals.

A yet further aspect of the present invention relates to methods for the treatment of human or non-human animals in which said pharmaceutical composition comprising liposomes, which have lipids with a transfection enhancer element in their membrane, as a carrier for active agents or ingredients is targeted to a specific organ or organs, tumours or sites of infection or inflammation.

It is to be understood that while the invention has been described in conjunction with the detailed description thereof, the foregoing description is intended to illustrate and not limit the scope of the invention, which is defined by the scope of the appended claims. Other aspects, advantages, and modifications are within the ambit of the following claims.

EXAMPLES

The invention will be further described in the following examples, which do not limit the scope of the invention.

Example 1

Synthesis of (16-{2-[2,3-Bis-hexadecanoyloxy-propoxy)-hydroxy-phosphoryl-oxy]-ethylamino}-hexadecanoic acid) (Pal-PE or w16-PE)

First step (a): Oxidation of 16-Hydroxy-hexadecanoic acid to 16-Oxo-hexadecanoic acid 10 g of compound 1 (16-hydroxy-hexanoic acid) (1 eq.) was oxidized with 16 g PCC (Pyridinium chlorochromate) in 1000 ml dichloromethane under $N_2$ atmosphere for 15 min at 40° C. The solvent was removed and the residue was resolved in acetic acid ethyl ester followed by a chromatography step on silica gel (eluent: acetic acid ethyl ester).

Second step (b): Reductive amination of compound 2 with dipalmitoyl phosphatidylethanolamine (DPPE)

Under $N_2$ atmosphere 11.8 g of DPPE (3) and 16 g sodium cyano-boronhydride ($NaCNBH_3$) were dissolved in 800 ml $CHCl_3/CH_3OH$ 1:1 and heated to 65° C. 9.44 g pyridine was added to the mixture. 4.6 g of compound 2 (16-oxo-hexadecanoic acid) was dissolved in 400 ml $CHCl_3/CH_3OH$ 1:1 and finally also added drop wise to the reaction mixture. After three hours the solvent was removed and the solid was washed two times with water before re-dissolved in 200 ml $CHCl_3/CH_3OH/H_2O$ 500:100:4. After separation of the two phases the solvent of the organic phase was removed. The crude product was purified by a chromatography on silica gel (eluent: $CHCl_3/CH_3OH/H_2O$ 500:100:4). The product was characterized by $^1$H-NMR, HPLC and thin layer chromatography.

Example 2

Synthesis of compound (10-{2-[2,3-Bis-hexadecanoyloxy-propoxy)-hydroxy-phosphoryloxy]-ethylamino}-decanoic acid) (Deca-PE or w10-PE)

This synthesis was performed according to example 1 instead of using 10-Hydroxydecanoic acid in step a.

Reaction scheme:

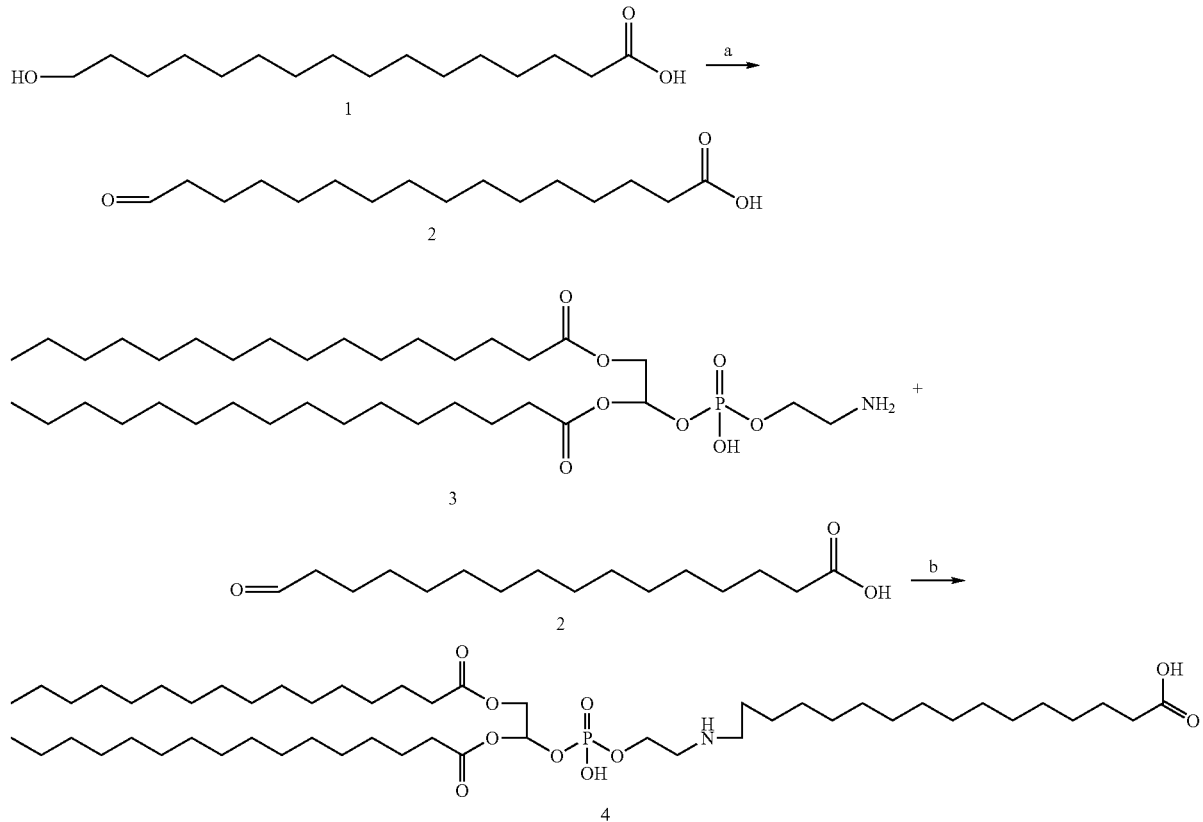

Example 3

Preparation of Amphoteric Liposomes Encapsulating Cy3-Labelled Antisense Oligonucleotides Following liposomal preparations were prepared as described below:

TABLE 22

Formulations L-1-L-5

| Formulation ID | Lipids | Mol % |
|---|---|---|
| L-1 | DOPE/MoChol/Chems/Pal-PE | 50:20:20:10 |
| L-2 | DOPE/MoChol/Chems/Deca-PE | 50:20:20:10 |
| L-3 | DOPE/MoChol/Chems | 50:20:30 |
| L-4 | POPC/DOPE/MoChol/Chems/Pal-PE | 12:38:20:20:10 |
| L-5 | POPC/DOPE/MoChol/Chems/Deca-PE | 12:38:20:20:10 |

Stock solutions of lipids in chloroform were mixed and finally evaporated in a round bottom flask to dryness under vacuum. Lipid films were hydrated with 1 ml Cy3-labelled antisense oligonucleotide solution in PBS pH 7.5 (0.5 mg/ml). The resulting lipid concentration was 50 mM. The suspensions were hydrated for 45 minutes in a water bath at room temperature, sonicated for 5 minutes following by three freeze/thaw cycles at −70° C. After thawing the liposomal suspensions were extruded 19 times through polycarbonate membranes with a pore size of 800/200/800 or 200/200 nm. Non-encapsulated oligonucleotide was removed by sedimentation. One formulation was prepared by a modified process:

TABLE 23

Formulation L-6

| Formulation ID | Lipids | Mol % |
|---|---|---|
| L-6 | POPC/DOPE/MoChol/Chems | 15:45:20:20 |

Briefly, lipids were weighed into a round bottom flask and solved in chloroform. Then a lipid film was produced by evaporating the solvent using a rotary evaporator. Chloroform residues were removed in vacuum overnight. Multilamellar vesicles were formed during the hydratisation of the lipid film with 1 ml Cy3-labelled antisense oligonucleotide solution in 10 mM NaAc, 50 mM NaCl pH 4.5 (0.35 mg/ml). After a freeze thaw step multilamellar liposomes were extruded 19 times through 800/200/800 or nm polycarbonate membranes. After the extrusion the pH of the liposome suspension was immediately shifted with ⅒ volume 1M Hepes pH 8. Non-encapsulated oligonucleotide was removed by sedimentation.

Lipid recovery and concentration was analysed by organic phosphate assay. Particle size was measured by dynamic light scattering on a Malvern Zetasizer 3000 HSA. Encapsulation efficiency was measured by fluorescence spectroscopy.
Results:

TABLE 24

Size, PI (Polydispersity index) and encapsulation efficiencies of formulations L-1-L-6

| Formulation ID | Size [nm]/PI | Encapsulation efficiency [%] |
|---|---|---|
| L-1 | 275/0.183 | 12 |
| L-2 | 251/0.387 | 18 |
| L-3 | 173/0.068 | 11 |
| L-4 | 244/0.186 | 20 |
| L-5 | 269/0.396 | 15 |
| L-6 | 227/0.052 | 69 |

Example 4

Preparation of Amphoteric Liposomes Encapsulating Carboxyfluorescein (CF)

Following liposomal preparations were prepared as described below:

TABLE 25

Formulations L-7-L10, L-12-L-15 and L-17-L-24

| Formulation ID | Lipids | Mol % |
|---|---|---|
| L-7 | DOPE/MoChol/Chems/Pal-PE | 50:20:20:10 |
| L-8 | DOPE/MoChol/Chems/Pal-PE | 56:20:20:4 |
| L-9 | DOPE/MoChol/Chems/Deca-PE | 50:20:20:10 |
| L-10 | DOPE/MoChol/Chems/Deca-PE | 56:20:20:4 |
| L-12 | POPC/DOPE/MoChol/Chems/Pal-PE | 12:38:20:20:10 |
| L-13 | POPC/DOPE/MoChol/Chems/Pal-PE | 15:41:20:20:4 |
| L-14 | POPC/DOPE/MoChol/Chems/Deca-PE | 12:38:20:20:10 |
| L-15 | POPC/DOPE/MoChol/Chems/Deca-PE | 15:41:20:20:4 |
| L-17 | POPC/DOTAP/Chems/Pal-PE | 50:10:30:10 |
| L-18 | POPC/DOTAP/Chems/Pal-PE | 56:10:30:4 |
| L-19 | POPC/DOTAP/Chems/Deca-PE | 50:10:30:10 |
| L-20 | POPC/DOTAP/Chems/Deca-PE | 56:10:30:4 |
| L-21 | POPC/DOTAP/Chems/Pal-PE | 15:28:47:10 |
| L-22 | POPC/DOTAP/Chems/Pal-PE | 21:28:47:4 |
| L-23 | POPC/DOTAP/Chems/Deca-PE | 15:28:47:10 |
| L-24 | POPC/DOTAP/Chems/Deca-PE | 21:28:47:4 |

Stock solutions of lipids in chloroform were mixed and finally evaporated in a round bottom flask to dryness under vacuum. Lipid films were hydrated with 100 mM CF in PBS pH 7.5. The resulting lipid concentration was 20 mM. The suspensions were hydrated for 45 minutes in a water bath at room temperature, sonicated for 5 minutes following by three freeze/thaw cycles at −70° C. After thawing the liposomal suspensions were extruded 15 times through polycarbonate membranes with a pore size of 800/200/800 nm. Non-encapsulated CF was removed by gel filtration, whereas the liposomes were diluted by a factor three. Lipid recovery and concentration was analysed by organic phosphate assay. Particle size was measured by dynamic light scattering on a Malvern Zetasizer 3000 HSA.
Results:

TABLE 26

Size and PI of formulations L-7-L10, L-12-L-15 and L-17-L-24

| Formulation ID | Size [nm]/PI |
|---|---|
| L-7 | 254/0.317 |
| L-8 | 192/0.114 |
| L-9 | 185/0.154 |
| L-10 | 175/0.074 |
| L-12 | 225/0.292 |
| L-13 | 181/0.117 |
| L-14 | 165/0.265 |

TABLE 26-continued

Size and PI of formulations L-7-L10, L-12-L-15 and L-17-L-24

| Formulation ID | Size [nm]/PI |
|---|---|
| L-15 | 169/0.113 |
| L-17 | 190/0.271 |
| L-18 | 205/0.211 |
| L-19 | 194/0.288 |
| L-20 | 143/0.190 |
| L-21 | 211/0.190 |
| L-22 | 212/0.244 |
| L-23 | 166/0.166 |
| L-24 | 141/0.117 |

Example 5

In Vitro Transfection Experiment with Liposomes Encapsulating Cy3-Labelled Antisense Oligonucleotides or Carboxyfluorescein (CF)

HeLa-Cells were obtained from DSMZ (German Collection of Micro Organism and Cell Cultures) and maintained in DMEM. Media were purchased from Gibco-Invitrogen and supplemented with 10% FCS at 37° C. under 5% $CO_2$. The cells were plated at a density of $2 \times 10^4$ cells/ml and cultivated in 100 µl medium. After 16 h the media were replaced with Opti-MEM I (Gibco) containing liposomes (L1-L24) with a total amount of 50 to 200 ng Cy3-labelled oligonucleotides or 0.5 mM CF/well. Cell culture dishes were centrifuged for 1 h at 450 g at 37° C., followed by an incubation of 3 h hours at 37° C. under 5% $CO_2$. The transfection mixture was replaced by the above mentioned medium and cells were incubated for further 24-48 h hours. Transfection efficiency and cellular distribution was determined after 4 or 24 hours by light and fluorescence microscopy using objectives with 10× or 40× magnification (Axionvert S 100, Carl Zeiss Inc.).

Figure 5:
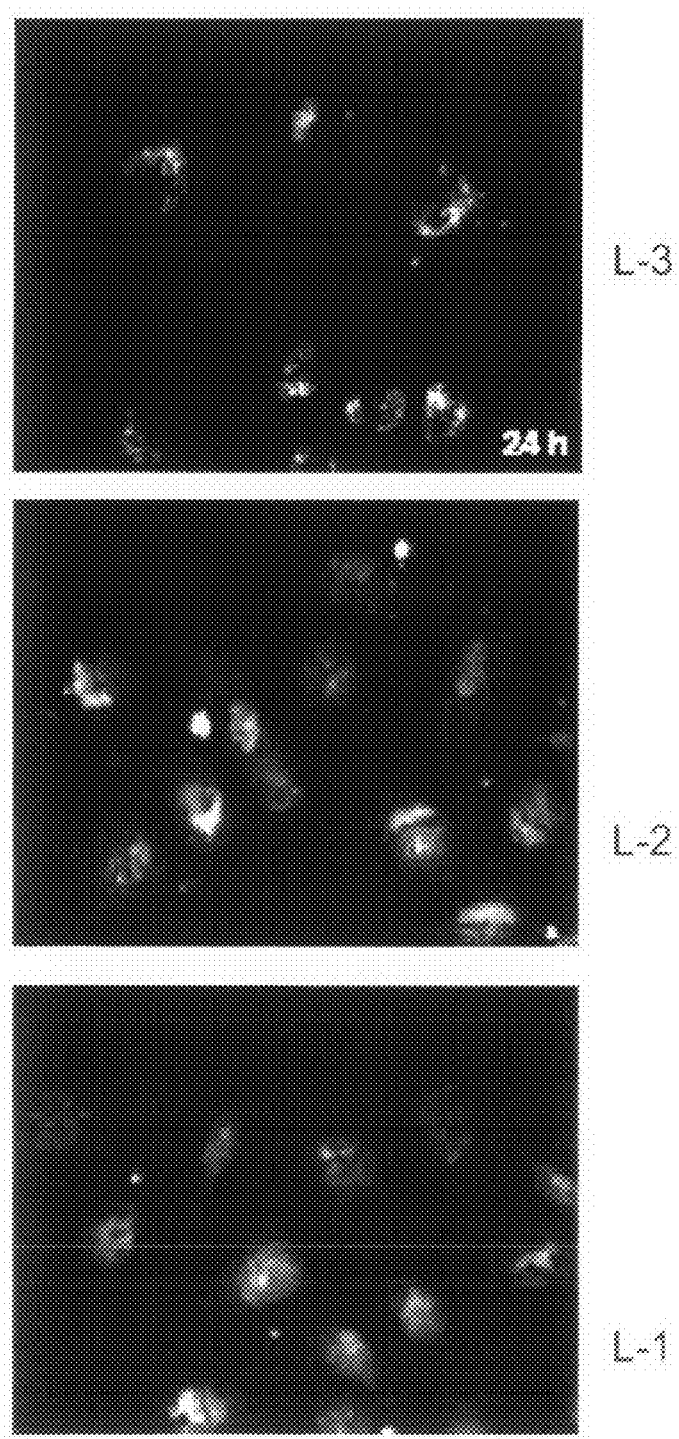
FIG. 5 shows fluorescence microscopy images of Hela-cells transfected with formulations L-1, L-2 and L-3 after 24 hours (40×) (magnification: 400×).

Results:

Transfection of HeLa-Cells with Liposomes Encapsulating Cy3-Labelled Oligonucleotides:

FIG. 5 shows fluorescence microscopy images of Hela-cells transfected with formulations L-1, L-2 and L-3. It is shown that the transfection efficiency of the liposomal formulation L-3 can be improved by inclusion of a lipid with a transfection enhancer element in the liposomal membrane (L-1 and L-2).

Figure 6:
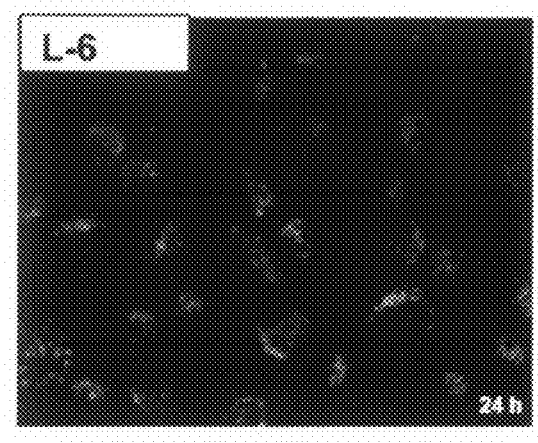
FIG. 6 shows fluorescence microscopy images of Hela-cells transfected with formulations L-4, L-5 and L-6 after 24 hours (40×) (magnification: 400×).
Figure 6:
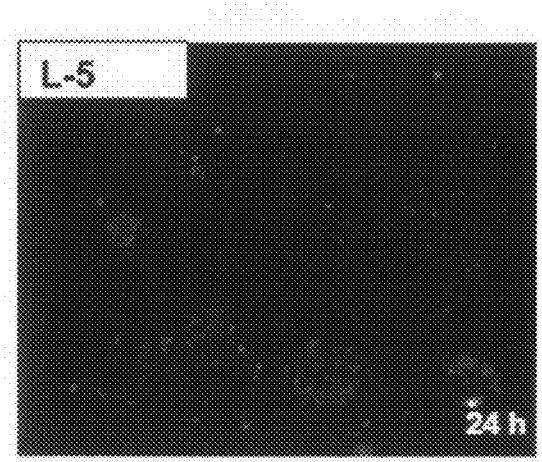
Figure 6:
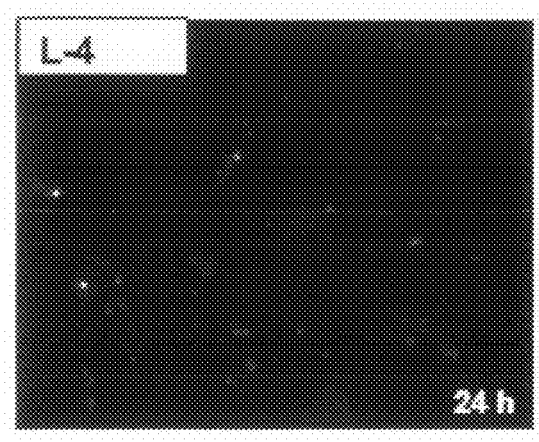

FIG. 6 shows fluorescence microscopy images of Hela-cells transfected with formulations L-4, L-5 and L-6. It is shown that the transfection efficiency of the liposomal formulation L-6 can be improved by inclusion of a lipid with a transfection enhancer element in the liposomal membrane (L-4 and L-5).

Transfection of HeLa-Cells with Liposomes Encapsulating Carboxyfluorescein:

Carboxyfluorescein is a pH-sensitive fluorescence probe which do not show a fluorescence signal in acidic environment (e.g. endosomes).

Figure 7:
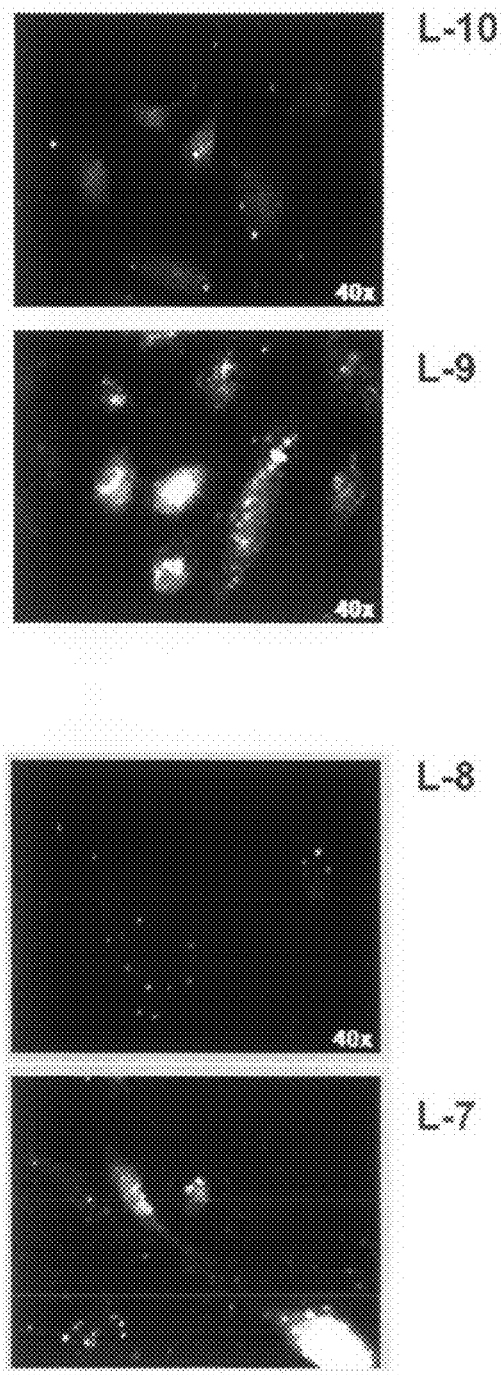
FIG. 7 shows fluorescence microscopy images of Hela cells transfected with formulations L-7-L-10 (40×) (magnification: 400×).

FIG. 7 shows the fluorescence microscopy images of Hela cells transfected with formulations L-7-L-10. All formulations show fluorescence signals in the cytosol or nucleus. The fluorescence signals are improved with formulation having 10% Pal-PE or Deca-PE in their membrane (L-7 and L-9).

Figure 8:
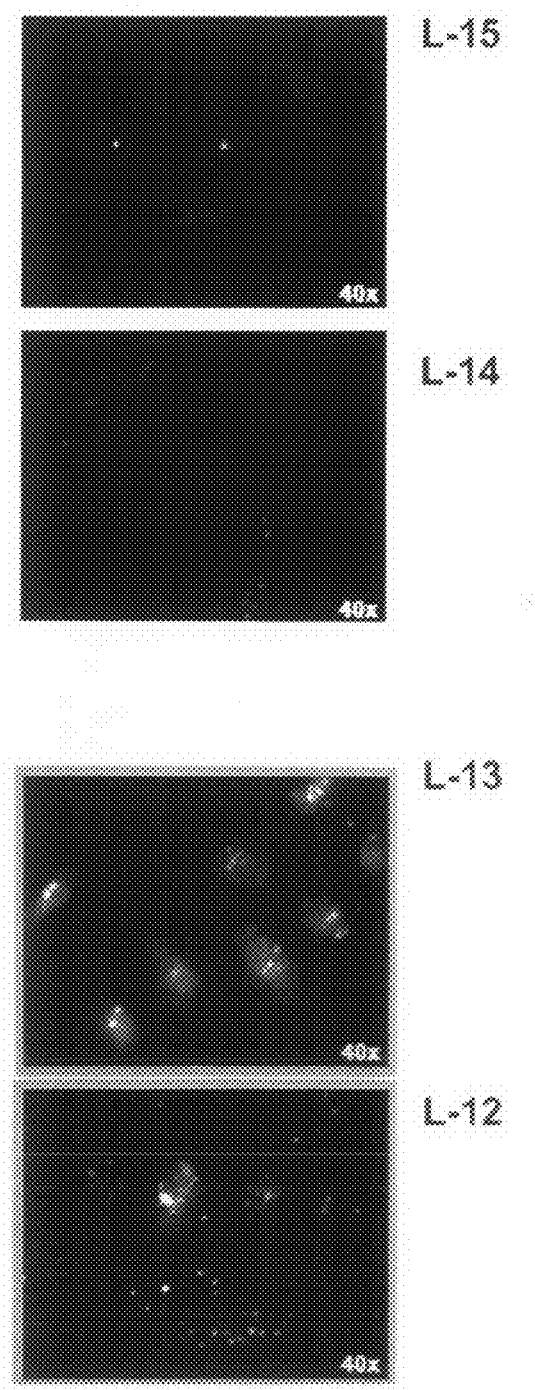
FIG. 8 shows fluorescence microscopy images of Hela cells transfected with formulations L-12-L-15 (40×) (magnification: 400×).

FIG. 8 shows the fluorescence microscopy images of Hela cells transfected with formulations L-12-L-15. In this case the fluorescence signal of the carboxyfluorescein is more intensive for formulations L-12 and L-13 having Pal-PE in their membrane. The amount of Pal-PE (4% or 10%) does not influence the fluorescence signal.

Figure 9:
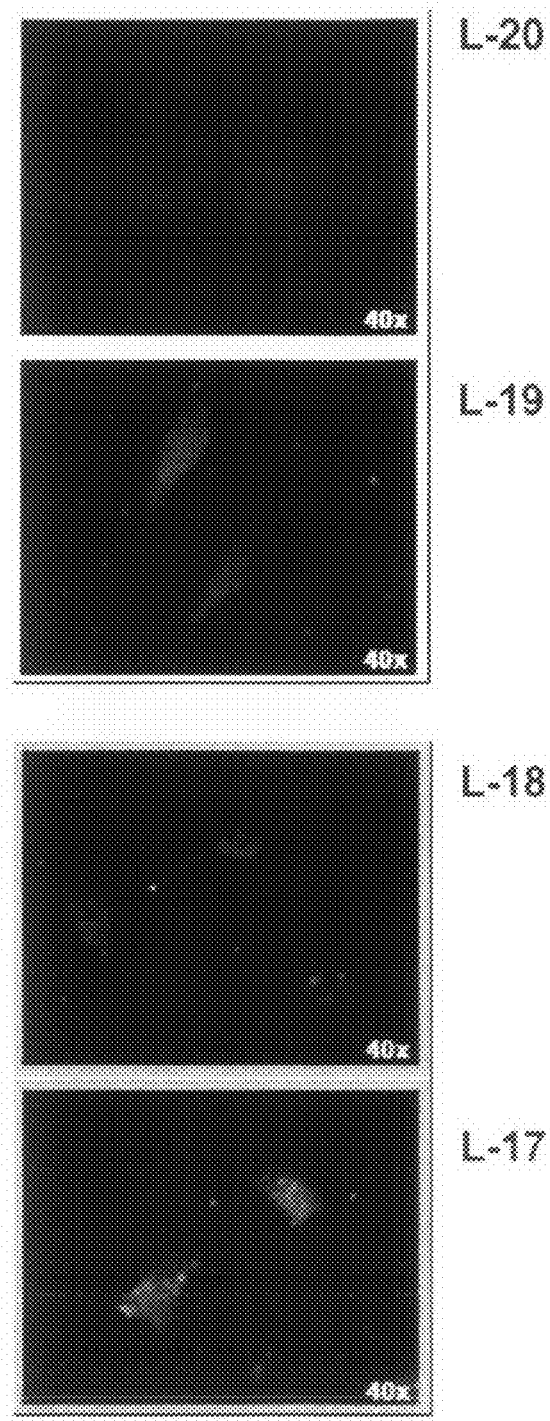
FIG. 9 shows fluorescence microscopy images of Hela cells transfected with formulations L-17-L-20 (40×) (magnification: 400×).

FIG. 9 shows the fluorescence microscopy images of Hela cells transfected with formulations L-17-L-20. In this case the fluorescence signal of the carboxyfluorescein is more intensive for formulations L-17 and L-19 having Pal-PE or 10% Deca-PE in their membrane.

Figure 10:
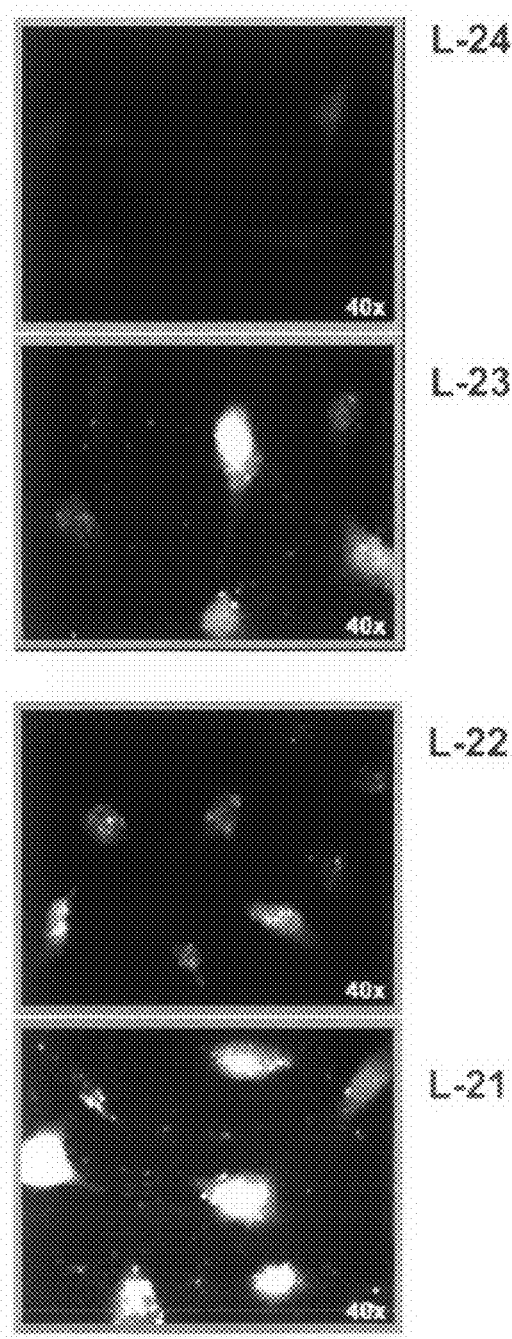
FIG. 10 shows fluorescence microscopy images of Hela cells transfected with formulations L-21-L-24 (40×) (magnification: 400×).

FIG. 10 shows the fluorescence microscopy images of Hela cells transfected with formulations L-21-L-24. All formulations show fluorescence signals in the cytosol or nucleus. The fluorescence signals are improved with formulation having 10% Pal-PE or Deca-PE in their membrane (L-21 and L-23).

Figure 11:
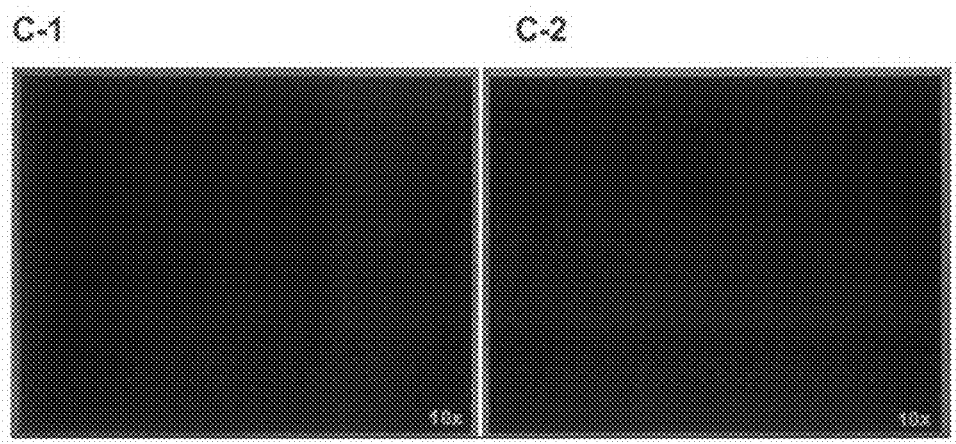
FIG. 11 shows fluorescence microscopy images of Hela cells transfected with free carboxyfluorescein (C1) or an anionic liposomal standard formulation (DPPC:DPPG:Chol 50:10:40) (C2), (10×) (magnification: 100×).

FIG. 11 shows fluorescence microscopy images of Hela cells transfected with free carboxyfluorescein or an anionic liposomal standard formulation (DPPC:DPPG:Chol 50:10: 40). Both formulations do not show any fluorescence signals.

Example 6

Biodistribution of Amphoteric Liposomes in Mice Bearing Tumor Xenografts

Preparation of Liposomes Encapsulating C5.5 Antisense Oligonucleotides:

Liposomes were manufactured by an alcohol-injection method. Lipid mixtures were dissolved in the appropriate alcohol (ethanol for L-25 and isopropanol/1% HCl for L-26) at a volume of 8 ml and an appropriate concentration (40 mM for L-25 and 20 mM for L-26) according to the distinct formulation. A volume of 72 ml of Cy5.5 labelled antisense oligonucleotide solution in 20 mM HAc, 300 mM sucrose buffer, pH 4.5 at the appropriate concentration (57 µg/ml for L-25 and 67 µg/ml for L-26), was transferred to a round-bottom flask. Both solutions were mixed using an injection device with pumps. The resulting liposomal suspensions were shifted to pH 7.5 with 1/10 of the total volume with 1 M tris(hydroxymethyl)aminomethane (Tris) HCl, pH 8, dialyzed against PBS to remove non-encapsulated Cy 5.5 labelled antisense oligonucleotides and subsequent concentrated.

TABLE 27

Formulations L-25 and L-26

| Form. ID | Lipids | Mol % | Size [nm]/PI | Encapsulation efficiency [%] |
|---|---|---|---|---|
| L-25 | POPC/DOTAP/Chems | 25:28:47 | 122/0.211 | 91 |
| L-26 | POPC/DOTAP/Chems/Pal-PE | 15:28:47:10 | 165/0.194 | 67 |

Preparation of Empty Liposomes:

Lipid mixtures for empty liposomes were dissolved in either ethanol (L-27) or isopropanol/1% HCL (L-28) with a concentration of 50 mM. Empty liposomes were prepared by mixing the lipids in organic solvent with an aqueous buffer (PBS or 10 mM Hac, 300 mM Sucrose, 100 mM Tris, pH7.5). Liposomal suspension were dialyzed against PBS and subsequent concentrated.

TABLE 28

Formulations L-27 and L-28

| Form. ID | Lipids | Mol % | Size [nm]/PI |
|---|---|---|---|
| L-27 | POPC/DOTAP/Chems | 25:28:47 | 62/0.311 |
| L-28 | POPC/DOTAP/Chems/Pal-PE | 15:28:47:10 | 174/0.124 |

Cy 5.5 antisense oligonucleotide loaded liposomes and empty liposomes were mixed to a final lipid concentration of 60 mM.

Biodistribution Study

50 μg of liposomal Cy 5.5 labelled antisense oligonucleotides (2 mg/kg) were injected intravenously into the tail vein of CD1 nude mice having a xenograft tumor (human hepatoma) (diameter of 6-8 mm). The group size was 2 mice per formulation. A control group received 150 μl PBS intravenously. 24 hours later mice were sacrificed and tumors were collected and frozen.

Deep-frozen tumors were partially embedded into OCT (Tissue-Tek) and 10 μm sections were made with the Cryostat Cryo-Star HM560 (Microm-International, Walldorf, Germany) at −20° C. Sections were collected and dried at Super Frost® Plus Gold slides (Menzel, Braunschweig, Germany) and stored at 4° C.

Imaging of cryosected organ slices was performed with LI-COR Odyssey Infrared Imaging Systems (LI-Cor Biosciences Gmbh, Bad Homburg, Germany)

Figure 12:
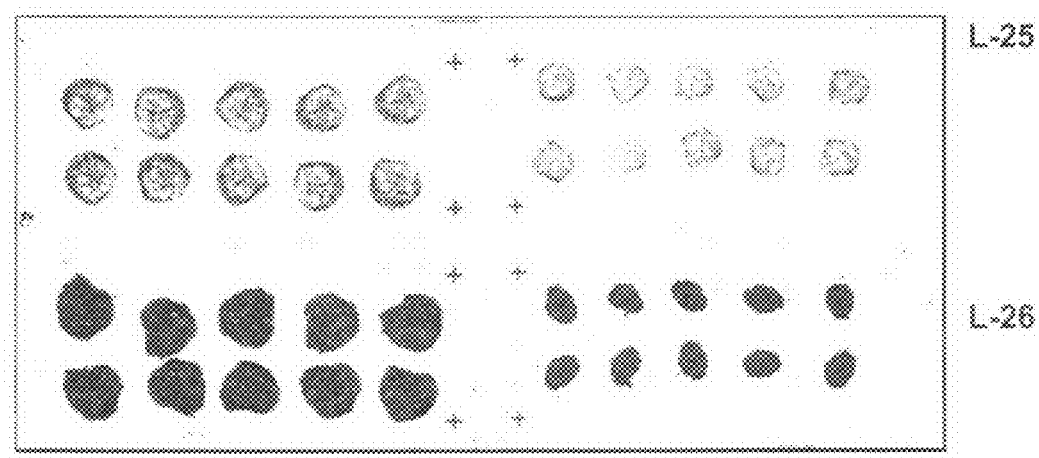
FIG. 12 shows the cryosected tumor tissue of tumor-bearing mice received an intravenous injection of liposomal formulations L-25 and L-26.

Results:

After an intravenous application of Cy5.5 labelled antisense oligonucleotides, encapsulated into liposomal formulations L-25 and L-26, an accumulation in tumor tissue was found. FIG. 12 shows the cryosected tumor tissue of both animals of a group. Compared to formulation L-25 the Pal-PE formulation L-26 shows an improved accumulation in tumor tissue by a factor 5.4. The tumor tissue of the animals received PBS buffer do not show any fluorescence signal.

Example 7

Tumor Therapy with Amphoteric Liposomes in Mice Bearing Tumor Xenografts

Preparation of Liposomes Encapsulating siRNA Targeting Plk1 or Non-Targeting Scrambled (scr) siRNA:

Liposomes were manufactured by an isopropanol-injection method. Lipid mixtures were dissolved in isopropanol/1% HCl at a volume of 238 ml and an appropriate concentration (10 mM). A volume of 554 ml of Plk1 or scr siRNA solution in 10 mM HAc, 300 mM sucrose, pH 4.0 (pH adjusted with NaOH) at the appropriate concentration (36 μg/ml), was transferred to a round-bottom flask. Both solutions were mixed using an injection device with pumps. The resulting liposomal suspensions were shifted to pH 7.5 with twice the volume of 136 mM $Na_2HPO_4$, 100 mM NaCl, pH 9.0, dialyzed 3 times against 100 mM $Na_2HPO_4$, 50 mM NaCl, 150 mM Sucrose, pH 7.5 to remove non-encapsulated siRNA and subsequent dialyzed 3 times with 9.6 mM $Na_2HPO_4$, 2.4 mM $KH_2PO4$, 280 mM Sucrose, pH 7.5 and finally concentrated.

Sequence of used siRNAs

```
1. Plk1 siRNA:
sense
5'- agaccuaccuccggaucaa(dTdT)-3'    (SEQ ID NO: 1)

Antisense
5'-uugauccggagguaggucu(dTdT)-3'    (SEQ ID NO: 2)

2. Scr siRNA:
sense
5'-aacuggguaagcgggcgca(dTdT)-3'    (SEQ ID NO: 3)

Antisense
5'-ugcgcccgcuuacccaguu(dTdT)-3'    (SEQ ID NO: 4)
```

Tumor Therapy:

125 μg of liposomal active Plk1 or scrambled siRNA (5 mg/kg) were injected intravenously into the tail vein of CD1 nude mice having a xenograft tumor (human hepatoma, Huh7) (diameter of 5 mm) twice a week, on day one and four, for three weeks. The group size was 5-7 mice per formulation or control. A control group received 200 μl Saline intravenously. The volume of the tumor was measured on each day of injection; the tumor weight was determined at the end of the experiment. 72 hours following the last injection mice were sacrificed and tumors were collected and frozen.

Figure 13:
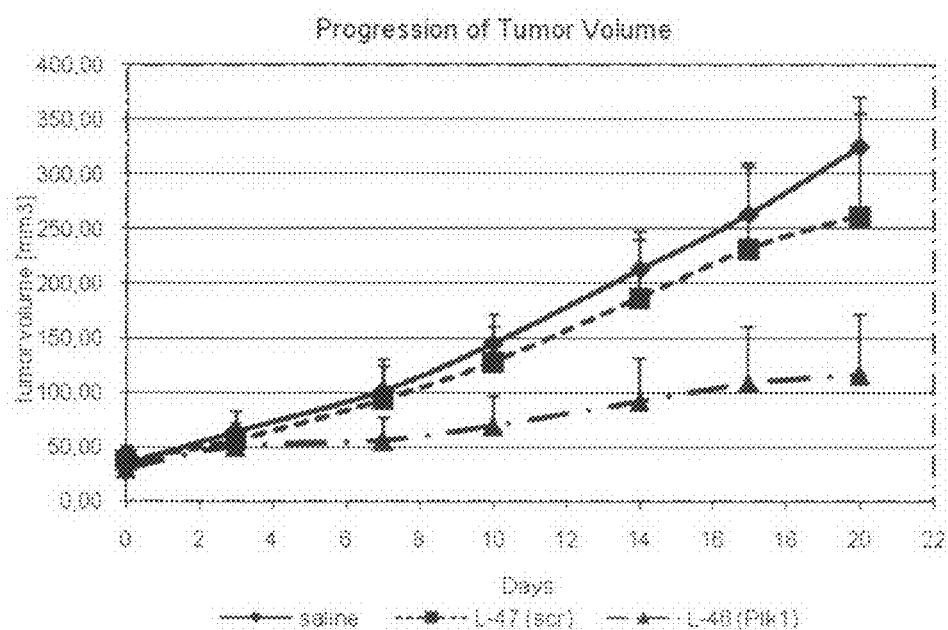
FIG. 13 shows the tumor volumes over the study period of treatment groups L-46 (Plk1), L-47 (scr) and saline.
Figure 14:
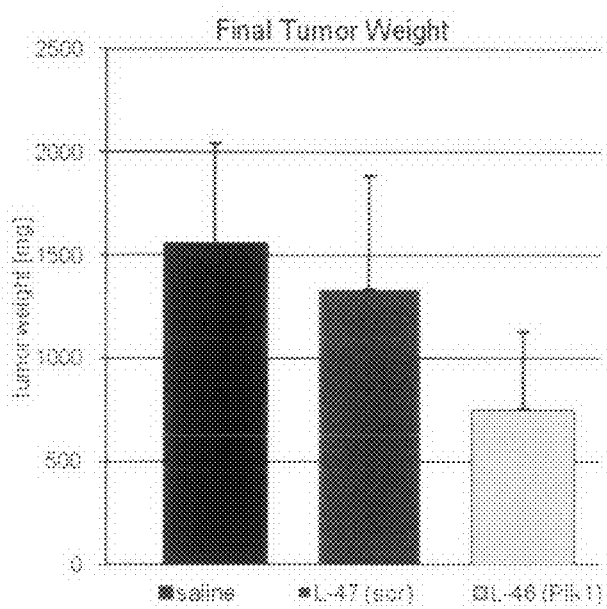
FIG. 14 shows the final tumor weights of the treatment groups L-46 (Plk1), L-47 (scr) and saline after sacrification of the animals at the end of the study.

Results:

After six intravenous applications of Plk1 siRNA encapsulated into L-46 over three weeks an inhibition of the tumor growth is obvious (FIG. 13) compared to the treatment with saline or scr siRNA (L-47). The final tumor weights in group 2 (L-46 Plk1) are clearly reduced compared to the control groups 1 or 3 (Saline or L-47 Scrambled), respectively (FIG. 14).

Example 8

Fusogenicity of Liposomes Comprising Lipids with a TEE

Paired samples of fluorescently labelled liposomes were prepared to monitor lipid fusion through the appearance of a FRET (Flourescence Resonance Energy Transfer) signal. 0.3 mol % of NBD-PE were added to the donor liposomes and 0.3 mol % of Rhodamine-PE were added to the receptor liposomes. All lipids were dissolved in isopropanol at a concentration of 20 mM and the individual mixtures as listed below were prepared. 50 μl of each individual alcoholic lipid sample was then rapidly mixed with either of the following buffers A) 360 μl 20 mM acetic acid/sodium hydroxide pH 4

B) 360 μl 20 mM acetic acid/sodium hydroxide pH 4, further comprising 15 μg siRNA

TABLE 29

Formulations L-46 and L-47

| Form. ID | siRNA | Lipids | Mol % | Size [nm]/PI | Encapsulation efficiency [%] |
|---|---|---|---|---|---|
| L-46 | Plk1 | POPC/DOTAP/Chems/Pal-PE | 15:28:47:10 | 202/0.58 | 58 |
| L-47 | scr | POPC/DOTAP/Chems/Pal-PE | 15:28:47:10 | 198/0.43 | 79 |

Treatment groups in the in vivo study were named as follows:

Group 1: Saline (PBS)

Group 2: L-46 Plk1, 5 mg/kg siRNA, 976 μmol/kg lipid

Group 3: L-47 Scrambled, 5 mg/kg siRNA, 616 μmol/kg lipid

C) 380 μl 10 mM acetic acid/10 mM phosphoric acid/sodium hydroxide, pH 7.5

Thus, liposomes were formed either at low pH or neutral pH, in the presence or absence of siRNA, an oligonucleotide that constitutes an important class of active ingredients. Liposomes in A) or B) were than neutralized using a small amount of 1M $Na_2HPO_4$ sample were exposed to buffers of decreasing pH. These buffers were comprising 20 mM citric acid and 40 mM phosphoric acid and were adjusted between pH 2 and pH 8 in 0.5 pH intervals.

pH induced fusion was allowed to take place at 37° C. for 2 h and all samples were measured for fluorescence using two sets of filters: NBD/Rhodamin: 460/590 nm and NBD/NBD: 460/530 nm. FRET as a signal for membrane fusion was expressed as the ratio of emission (590 nm)/emission (530 nm). Values smaller 0.5 indicate background fluorescence, all higher values indicate fusion between liposomes.

It becomes apparent from the data in the table 31 that most of the tested formulations were fusogenic. Formulations comprising DC-Chol as cationic lipid component were found to be exceptionally fusogenic at intermediate pH values, but form stable liposomes both at neutral and at acidic pH. It was of less importance whether the liposomes were generated at neutral pH and thus were never exposed to acidic pH before the measurement or whether such liposomes were produced at acidic pH and brought to neutrality before use. Also, the presence of a cargo molecule such as siRNA did not affect the fusion behavior of the liposomes.

TABLE 30

| Formulation ID | 15 mol % | 28 mol % | 47 mol % | 10 mol % |
|---|---|---|---|---|
| L-29 | POPC | DDAB | Chems | Pal-PE |
| L-30 | POPC | DDAB | Chol-C3 | Pal-PE |
| L-31 | POPC | DDAB | Chol-C5 | Pal-PE |
| L-32 | POPC | DDAB | Chol-C6 | Pal-PE |
| L-33 | POPC | DDAB | Chol-C8 | Pal-PE |
| L-34 | POPC | DC-Chol | DMGS | Pal-PE |
| L-35 | POPC | DC-Chol | CHol-C3 | Pal-PE |
| L-36 | POPC | DC-Chol | Chol-C5 | Pal-PE |
| L-37 | POPC | DC-Chol | Chol-C6 | Pal-PE |
| L-38 | POPC | DC-Chol | Chol-C8 | Pal-PE |
| L-39 | POPC | DC-Chol | Chems | Pal-PE |
| L-40 | Lig-Ly PC | DOTAP | Chems | Pal-PE |
| L-41 | C6-Cer | DOTAP | Chems | Pal-PE |
| L-42 | SM | DC-Chol | Chems | Pal-PE |
| L-43 | POPC | DOTAP | Chems | Pal-PE |

Both the NBD-PE and the Rhodamine-PE labelled liposomes were then mixed and small aliquots of this mixed

TABLE 31

| Formulation ID | | pH 2.50 | 3.00 | 3.50 | 4.00 | 4.50 | 5.00 | 5.50 | 6.00 | 6.50 | 7.00 | 8.00 |
|---|---|---|---|---|---|---|---|---|---|---|---|---|
| L-29 | +APO B, pH 4 | 0.32 | 0.36 | 0.55 | 0.67 | 0.92 | 0.92 | 0.51 | 0.39 | 0.29 | 0.29 | 0.29 |
|  | empty, pH 4 |  | 0.32 | 0.37 | 0.49 | 0.62 | 0.96 | 0.66 | 0.49 | 0.32 | 0.30 | 0.30 |
|  | empty, pH 7.5 |  | 0.35 | 0.36 | 0.50 | 0.96 | 1.05 | 0.65 | 0.39 | 0.32 | 0.30 | 0.29 |
| L-30 | +APO B, pH 4 | 0.38 | 0.40 | 0.84 | 0.94 | 0.59 | 0.32 | 0.32 | 0.31 | 0.31 | 0.31 | 0.30 |
|  | empty, pH 4 |  | 0.36 | 0.78 | 1.11 | 0.65 | 0.35 | 0.34 | 0.33 | 0.33 | 0.32 | 0.31 |
|  | empty, pH 7.5 |  | 0.47 | 0.69 | 1.06 | 0.69 | 0.44 | 0.35 | 0.33 | 0.32 | 0.32 | 0.31 |
| L-31 | +APO B, pH 4 | 0.32 | 0.39 | 0.52 | 0.66 | 0.90 | 0.75 | 0.44 | 0.36 | 0.29 | 0.29 | 0.28 |
|  | empty, pH 4 |  | 0.33 | 0.42 | 0.48 | 0.59 | 0.66 | 0.58 | 0.44 | 0.30 | 0.29 | 0.29 |
|  | empty, pH 7.5 |  | 0.32 | 0.33 | 0.41 | 0.73 | 0.84 | 0.73 | 0.44 | 0.31 | 0.29 | 0.29 |
| L-32 | +APO B, pH 4 | 0.31 | 0.40 | 0.51 | 0.58 | 0.74 | 0.60 | 0.59 | 0.41 | 0.29 | 0.28 | 0.28 |
|  | empty, pH 4 |  | 0.32 | 0.35 | 0.39 | 0.43 | 0.59 | 0.60 | 0.45 | 0.31 | 0.29 | 0.29 |
|  | empty, pH 7.5 |  | 0.31 | 0.33 | 0.37 | 0.44 | 0.49 | 0.56 | 0.40 | 0.32 | 0.29 | 0.28 |
| L-33 | +APO B, pH 4 | 0.33 | 0.41 | 0.57 | 0.65 | 0.64 | 0.56 | 0.52 | 0.52 | 0.31 | 0.29 | 0.29 |
|  | empty, pH 4 |  | 0.35 | 0.47 | 0.53 | 0.53 | 0.58 | 0.55 | 0.56 | 0.31 | 0.30 | 0.29 |
|  | empty, pH 7.5 |  | 0.35 | 0.42 | 0.50 | 0.53 | 0.55 | 0.54 | 0.50 | 0.35 | 0.30 | 0.29 |
| L-34 | +APO B, pH 4 | 0.48 | 0.45 | 0.85 | 1.49 | 1.94 | 0.88 | 0.46 | 0.34 | 0.32 | 0.32 | 0.30 |
|  | empty, pH 4 |  | 0.36 | 0.51 | 0.96 | 1.86 | 0.99 | 0.54 | 0.35 | 0.32 | 0.31 | 0.30 |
|  | empty, pH 7.5 |  | 0.64 | 0.86 | 1.28 |  | 1.33 | 0.62 | 0.40 | 0.36 | 0.33 | 0.31 |
| L-35 | +APO B, pH 4 | 0.51 | 0.54 | 1.74 |  | 0.84 | 0.37 | 0.37 | 0.37 | 0.36 | 0.35 | 0.34 |
|  | empty, pH 4 |  | 0.40 | 0.91 |  | 1.07 | 0.39 | 0.38 | 0.37 | 0.36 | 0.36 | 0.34 |
|  | empty, pH 7.5 |  | 0.78 | 1.38 |  | 0.89 | 0.44 | 0.41 | 0.40 | 0.38 | 0.37 | 0.34 |
| L-36 | +APO B, pH 4 | 0.40 | 0.50 | 0.86 | 1.28 | 1.84 | 1.92 | 1.48 | 0.51 | 0.34 | 0.33 | 0.32 |
|  | empty, pH 4 |  | 0.38 | 0.55 | 0.95 | 1.34 |  | 1.40 | 0.61 | 0.36 | 0.35 | 0.34 |
|  | empty, pH 7.5 |  | 0.53 | 0.75 | 1.05 | 1.62 |  | 1.59 | 0.45 | 0.34 | 0.33 | 0.31 |
| L-37 | +APO B, pH 4 | 0.36 | 0.53 | 0.82 | 1.01 | 1.53 | 1.50 | 1.34 | 0.64 | 0.32 | 0.31 | 0.30 |
|  | empty, pH 4 |  | 0.37 | 0.59 | 0.76 | 1.12 | 1.88 | 1.64 | 0.88 | 0.34 | 0.33 | 0.31 |
|  | empty, pH 7.5 |  | 0.51 | 0.67 | 0.83 | 1.22 | 1.62 | 1.56 | 0.55 | 0.34 | 0.31 | 0.30 |
| L-38 | +APO B, pH 4 | 0.38 | 0.49 | 0.80 | 1.02 | 1.44 | 1.33 | 1.14 | 0.90 | 0.31 | 0.30 | 0.29 |
|  | empty, pH 4 |  | 0.37 | 0.51 | 0.63 | 0.71 | 1.09 | 1.20 | 1.01 | 0.36 | 0.31 | 0.29 |
|  | empty, pH 7.5 |  | 0.50 | 0.74 | 0.79 | 1.06 | 1.18 | 1.33 | 1.06 | 0.37 | 0.30 | 0.29 |
| L-39 | +APO B, pH 4 | 0.42 | 0.56 | 0.94 | 1.21 | 1.94 | 1.86 | 0.73 | 0.40 | 0.35 | 0.34 | 0.33 |
|  | empty, pH 4 |  | 0.40 | 0.83 | 1.30 | 1.68 | 1.86 | 0.91 | 0.49 | 0.36 | 0.35 | 0.34 |
|  | empty, pH 7.5 |  | 0.56 | 0.91 | 1.02 | 1.84 |  | 1.11 | 0.42 | 0.36 | 0.35 | 0.32 |
| L-40 | +APO B, pH 4 | 0.37 | 0.54 | 0.83 | 0.89 | 1.14 | 1.13 | 1.00 | 0.55 | 0.33 | 0.32 | 0.31 |
|  | empty, pH 4 |  | 0.39 | 0.47 | 0.58 | 0.71 | 0.98 | 0.82 | 0.61 | 0.35 | 0.32 | 0.31 |
|  | empty, pH 7.5 |  | 0.41 | 0.43 | 0.51 | 0.69 | 0.85 | 0.95 | 0.55 | 0.37 | 0.31 | 0.31 |
| L-41 | +APO B, pH 4 | 0.41 | 0.53 | 0.89 | 1.38 | 1.31 | 1.16 | 0.80 | 0.39 | 0.32 | 0.32 | 0.31 |
|  | empty, pH 4 |  | 0.35 | 0.55 | 1.46 | 1.36 | 1.24 | 1.19 | 0.47 | 0.32 | 0.32 | 0.31 |
|  | empty, pH 7.5 |  | 0.52 | 0.67 | 1.35 | 1.35 | 1.31 | 1.26 | 0.51 | 0.37 | 0.33 | 0.32 |
| L-42 | +APO B, pH 4 | 0.41 | 0.56 | 1.17 | 1.83 |  | 1.49 | 0.50 | 0.37 | 0.36 | 0.35 | 0.34 |
|  | empty, pH 4 |  | 0.48 | 0.85 | 1.27 | 1.82 | 1.64 | 0.76 | 0.42 | 0.36 | 0.36 | 0.34 |
|  | empty, pH 7.5 |  | 0.53 | 0.74 | 0.80 | 1.18 | 1.28 | 0.85 | 0.44 | 0.34 | 0.31 | 0.30 |
| L-43 | +APO B, pH 4 | 0.37 | 0.53 | 0.67 | 0.81 | 1.03 | 0.96 | 0.92 | 0.53 | 0.33 | 0.32 | 0.31 |
|  | empty, pH 4 |  | 0.37 | 0.45 | 0.64 | 0.89 | 0.95 | 0.94 | 0.54 | 0.34 | 0.32 | 0.31 |
|  | empty, pH 7.5 |  | 0.41 | 0.51 | 0.57 | 0.87 | 0.98 | 0.97 | 0.59 | 0.36 | 0.32 | 0.31 |

Example 9

Use of Liposomes Comprising a TEE In Vivo siRNA-loaded amphoteric liposomes were manufactured using ApoB as a target gene for this study. A scrambled, non-targeting siRNA was used for control purposes.

The lipid mixture L-44 (POPC:DOTAP:CHEMS:Pal-PE, 15:28:47:10) or L-45 (POPC:DC-Chol:DMGS:Pal-PE, 15:28:47:10) was dissolved at a concentration of 35 mM for L-44 or 25 mM for L-45 in isopropanol containing 10 mM HCl. Appropriate volumes of siRNA stock solution were diluted in 10 mM HAc, 300 mM sucrose/Tris(hydroxymethyl)aminomethan (TRIS) pH 4. The organic and the aqueous solution were mixed in a 3:7 ratio and the liposomal suspension was immediately shifted to pH >7.5 with 150 mM Tris pH 8.

Formulations were concentrated by a factor of 20 or 30 using the tangential flow method on a Pellicon® XL cassette with polyethersulfone membranes (Millipore Corporation, Billerica, Mass.). The outside buffer was exchanged by adding successively 5-times the volume of 100 mM Tris/$H_3PO_4$, 150 mM sucrose pH 7.4 followed by the successive addition of 20 mM Tris, 280 mM sucrose buffer that was titrated to pH 7.4 with $H_3PO_4$.

The treatment schedule for the in vivo study was as follows: A total of 5 male C57 BC/6 mice per treatment group were injected intravenously (i.v.) on days 0, 1, and 2 with the respective formulation at ApoB or scrambled siRNA dosages of 8 mg/kg and an injection volume of 250 µl (see list of treatment groups below). Injections of saline served as a control. Mice were sacrificed 24 h after the last treatment, whole blood was collected, and plasma was separated. Plasma of all mice was analyzed for AST and ALT. Volumes of 10 µl plasma were mixed with 40 µl NuPage® LDS sample buffer 4× (Invitrogen, Carlsbad, Calif.) containing 50 mM DTT for analysis of ApoB in plasma. ApoB in plasma was analyzed by Western blot. For mRNA analysis, approximately 100 mg of liver tissue was collected in 10-times the volume (1 ml) of RNAlater® buffer (Sigma-Aldrich Chemical Company, St. Louis, Mo.). The mRNA in all liver samples was quantified using the Quantigene Assay (Panomics, Calif.).

Treatment groups in the in vivo study were named as follows:
Group 1: Saline (PBS)
Group 2: L-44 ApoB, 8 mg/kg siRNA, 440 µmol/kg lipid
Group 3: L-44 Scrambled, 8 mg/kg, 370 µmol/kg lipid
Group 4: L-45 ApoB, 8 mg/kg, 520 µmol/kg lipid
Group 5: L-45 Scrambled, 8 mg/kg, 560 µmol/kg lipid Animals received injection on day 1, 2 and 3 and were sacrificed on day 4.

Treatment resulted in reduction of Apo plasma protein levels of 40% (L-44 ApoB) or 45% (L-45 ApoB). The mRNa in the liver was reduced by 65% (L-44 ApoB) or 75% (L-45 ApoB). The liver enzymes AST and ALT were found unchanged even after intense treatment, indicating good tolerability of the formulations in vivo.

Example 10

Influence of the Chain Length of the Hydrophobic Moiety of TEE's

Liposomes were prepared from mixtures comprising neutral or zwitterionic lipids and increasing amounts of a TEE-lipid (0 mol %, 2.5 mol %, 5 mol % or 10 mol %), wherein the chain length of the hydrophobic moieties of the used TEEs was varied between 6 and 20.
A. POPC/DOPE=0.3
B. POPC/Chol=1
TEE-lipids used in the experiment:

| | |
|---|---|
| w6-PE | w6-DPTAP |
| w10-PE | |
| w12-PE | w12-DPTAP |
| w16-PE | w16-DPTAP |
| | w20-DPTAP |

TABLE 32

| Lipid 1 | Lipid 2 | TEE-Lipid | Mol % |
|---|---|---|---|
| POPC | DOPE | w6-PE | 33.3:66.6:0 |
| POPC | DOPE | w6-PE | 32.5:65:2.5 |
| POPC | DOPE | w6-PE | 31.7:63.3:5 |
| POPC | DOPE | w6-PE | 30:60:10 |
| POPC | DOPE | w10-PE | 33.3:66.6:0 |
| POPC | DOPE | w10-PE | 32.5:65:2.5 |
| POPC | DOPE | w10-PE | 31.7:63.3:5 |
| POPC | DOPE | w10-PE | 30:60:10 |
| POPC | DOPE | w12-PE | 33.3:66.6:0 |
| POPC | DOPE | w12-PE | 32.5:65:2.5 |
| POPC | DOPE | w12-PE | 31.7:63.3:5 |
| POPC | DOPE | w12-PE | 30:60:10 |
| POPC | DOPE | w16-PE | 33.3:66.6:0 |
| POPC | DOPE | w16-PE | 32.5:65:2.5 |
| POPC | DOPE | w16-PE | 31.7:63.3:5 |
| POPC | DOPE | w16-PE | 30:60:10 |
| POPC | DOPE | w6-DPTAP | 33.3:66.6:0 |
| POPC | DOPE | w6-DPTAP | 32.5:65:2.5 |
| POPC | DOPE | w6-DPTAP | 31.7:63.3:5 |
| POPC | DOPE | w6-DPTAP | 30:60:10 |
| POPC | DOPE | w12-DPTAP | 33.3:66.6:0 |
| POPC | DOPE | w12-DPTAP | 32.5:65:2.5 |
| POPC | DOPE | w12-DPTAP | 31.7:63.3:5 |
| POPC | DOPE | w12-DPTAP | 30:60:10 |
| POPC | DOPE | w16-DPTAP | 33.3:66.6:0 |
| POPC | DOPE | w16-DPTAP | 32.5:65:2.5 |
| POPC | DOPE | w16-DPTAP | 31.7:63.3:5 |
| POPC | DOPE | w16-DPTAP | 30:60:10 |
| POPC | DOPE | w20-DPTAP | 33.3:66.6:0 |
| POPC | DOPE | w20-DPTAP | 32.5:65:2.5 |
| POPC | DOPE | w20-DPTAP | 31.7:63.3:5 |
| POPC | DOPE | w20-DPATP | 30:60:10 |
| POPC | Chol | w6-PE | 50:50:0 |
| POPC | Chol | w6-PE | 48.8:48.8:2.5 |
| POPC | Chol | w6-PE | 47.5:47.5:5 |
| POPC | Chol | w6-PE | 45:45:10 |
| POPC | Chol | w10-PE | 50:50:0 |
| POPC | Chol | w10-PE | 48.8:48.8:2.5 |
| POPC | Chol | w10-PE | 47.5:47.5:5 |
| POPC | Chol | w10-PE | 45:45:10 |
| POPC | Chol | w12-PE | 50:50:0 |
| POPC | Chol | w12-PE | 48.8:48.8:2.5 |
| POPC | Chol | w12-PE | 47.5:47.5:5 |
| POPC | Chol | w12-PE | 45:45:10 |
| POPC | Chol | w16-PE | 50:50:0 |
| POPC | Chol | w16-PE | 48.8:48.8:2.5 |
| POPC | Chol | w16-PE | 47.5:47.5:5 |
| POPC | Chol | w16-PE | 45:45:10 |
| POPC | Chol | w6-DPTAP | 50:50:0 |
| POPC | Chol | w6-DPTAP | 48.8:48.8:2.5 |
| POPC | Chol | w6-DPTAP | 47.5:47.5:5 |
| POPC | Chol | w6-DPTAP | 45:45:10 |
| POPC | Chol | w12-DPTAP | 50:50:0 |
| POPC | Chol | w12-DPTAP | 48.8:48.8:2.5 |
| POPC | Chol | w12-DPTAP | 47.5:47.5:5 |
| POPC | Chol | w12-DPTAP | 45:45:10 |
| POPC | Chol | w16-DPTAP | 50:50:0 |
| POPC | Chol | w16-DPTAP | 48.8:48.8:2.5 |
| POPC | Chol | w16-DPTAP | 47.5:47.5:5 |

TABLE 32-continued

| Lipid 1 | Lipid 2 | TEE-Lipid | Mol % |
|---|---|---|---|
| POPC | Chol | w16-DPTAP | 45:45:10 |
| POPC | Chol | w20-DPTAP | 50:50:0 |
| POPC | Chol | w20-DPTAP | 48.8:48.8:2.5 |
| POPC | Chol | w20-DPTAP | 47.5:47.5:5 |
| POPC | Chol | w20-DPATP | 45:45:10 |

Fusability of the lipid mixtures was investigated using a lipid mixing assay, based on FRET. Liposomes, single labelled with 0.75 mol % NBD-PE (N-(7-nitrobenz-2-oxa-1,3-diazol-4-yl)-1,2-dihexadecanoyl-sn-glycero-3-phosphoethanol-amine, trimethylammonium salt) or Rhodamine-PE (Lissamine™ rhodamine B 1,2-dihexadecanoyl-sn-glycero-3-phosphoethanolamine, triethylammonium salt), respectively, were prepared to monitor lipid fusion through the appearance of a FRET signal.

Lipids were dissolved in isopropanol and mixed. Liposomes were produced by adding buffer (acetic acid 10 mM, phosphoric acid 10 mM, NaOH, pH 7.5) to the alcoholic lipid mix, resulting in a final lipid concentration of 1.6 mM and a final isopropanol concentration of 12.2%. For the preparation of the liposomes a liquid handling robot (Perkin Elmer, Multiprobe 11 Ex) was used. The NBD-labelled and Rh-labelled liposomes were combined in a ratio 1:1 and subsequent diluted 1:1 with the buffer mentioned above. Finally small aliquots of this mixed sample were brought to decreasing specific pHs (HAc 50 mM, Phosphoric acid 50 mM, NaOH, pH 7.5; 6.5; 5.5; 4.5; 3.5; 2.5) and incubated at 37° C. for 2 h. Liposomes were diluted again 1:1 in this step.

Samples were measured for fluorescence using two sets of filters: NBD/Rhodamine:460/590 nm and NBD/NBD:460/530 nm. FRET as a signal for membrane fusion was expressed as the ratio of emission (590 nm)/emission (530 nm). A background of 0.35 indicates background fluorescence and was therefore subtracted from the FRET signals.

To discriminate between fusion and mere aggregation the suspension was neutralized to pH 7.5 and FRET signals were measured again. A possible interference of the remaining alcohol content of 3% on the fusion of liposomes was excluded by pre-experiments.

The fusion can be expressed as Σ FRET, the sum of all measured FRET signals between pH 2.5 and pH 7.5.

Figure 15:
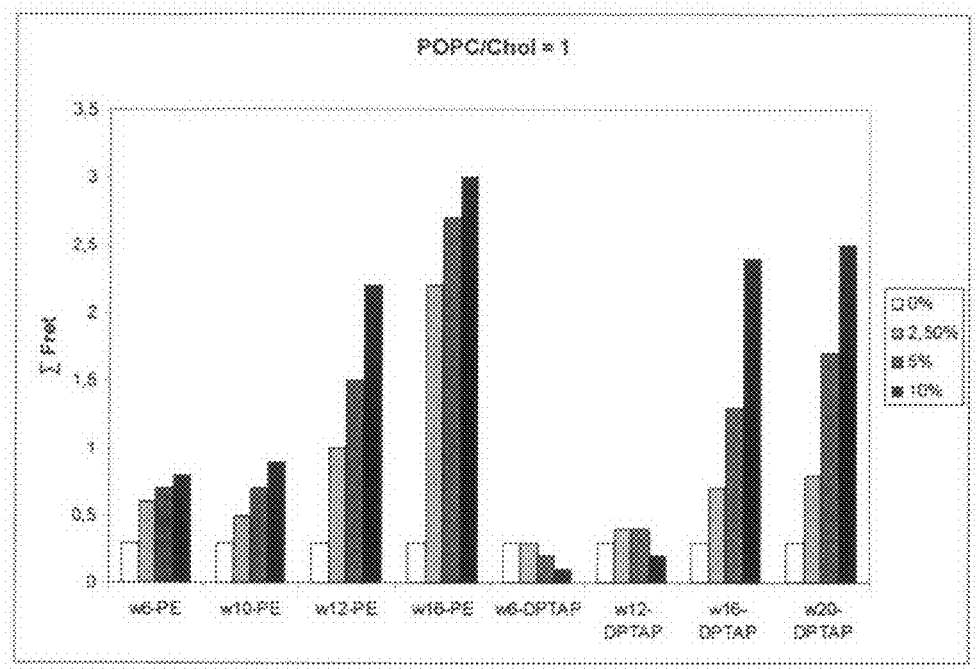
FIG. 15 show the intensity of fusion (expressed as Σ FRET of all measured Fret signals over the pH range of between 7.5 and 2.5) for liposomes from POPC/Chol 1:1 and increasing amounts (0-10%) of different TEE-lipids as indicated.
Figure 16:
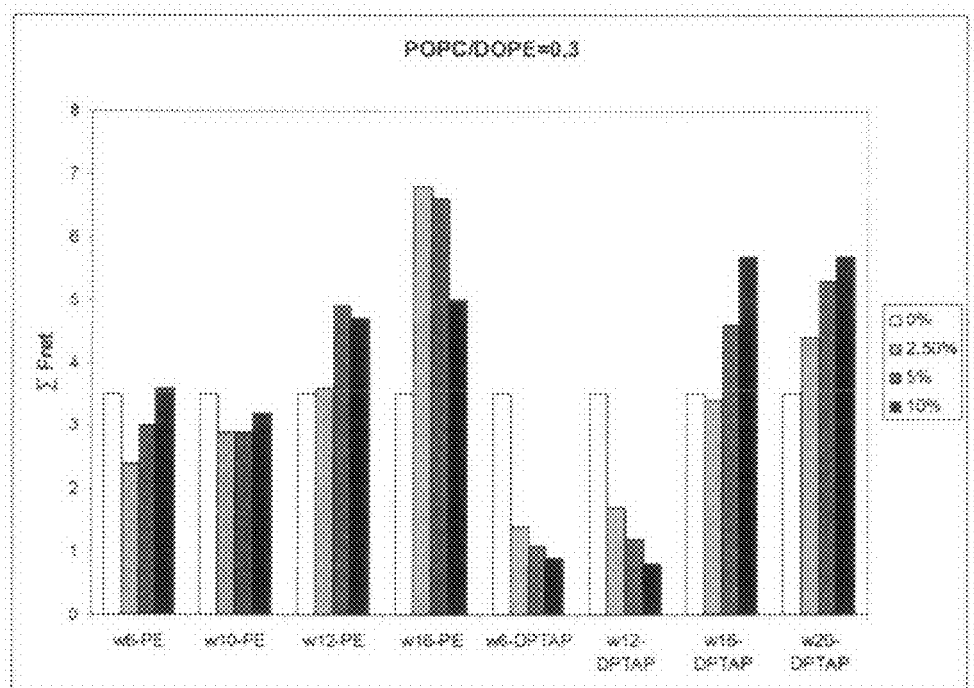
FIG. 16 show the intensity of fusion (expressed as Σ FRET of all measured Fret signals over the pH range of between 7.5 and 2.5) for liposomes from POPC/DOPE 1:3 and increasing amounts (0-10%) of different TEE-lipids as indicated.

FIGS. 15 and 16 show the fusion, expressed as Σ FRET, of neutral or zwitterionic lipid mixtures comprising increasing amounts of TEE-lipids. The results clearly demonstrate that the longer the chain length of the hydrophobic moiety of the TEE the stronger the fusion of the liposomes.

Example 11

In Vitro Transfection Experiment with Liposomes Encapsulating Carboxyfluorescein (CF)

Preparation of Liposomes:

Following liposomal preparations were prepared as described in example 4. The liposomal suspensions were extruded 19 times through polycarbonate membranes with a pore size of 800/800 nm.

TABLE 33

| Formulations L-46-L-49 | | |
|---|---|---|
| Formulation ID | Lipids | Mol % |
| L-46 | POPC/DOTAP/Chems | 25:28:47 |
| L-47 | POPC/DOTAP/Chems/Pal-PE | 15:28:47:10 |
| L-48 | POPC/DOPE/MoChol/DMG-Succ | 6:24:23:47 |
| L-49 | POPC/DOPE/MoChol/DMG-Succ/Pal-PE | 5:22:21:42:10 |

In Vitro Transfection:

HeLa-Cells were obtained from DSMZ (German Collection of Micro Organism and Cell Cultures) and maintained in DMEM. Media were purchased from Gibco-Invitrogen and supplemented with 10% FCS at 37° C. under 5% $CO_2$. The cells were plated at a density of $4 \times 10^4$ cells/ml and cultivated in 100 μl medium. After 16 h the media were replaced with Opti-MEM I (Gibco) containing liposomes (L-46-L-49) with a total amount of 0.05 mM CF/well. Cell culture dishes were incubated for 4 hours at 37° C. under 5% $CO_2$. Transfection efficiency and cellular distribution was determined after 4 hours by fluorescence microscopy with an exposure time of 5 seconds and using the 10/100 fold objective (Axionvert S 100, Carl Zeiss Inc.). Before imaging cells were washed several times (5×) with PBS pH7.4 and analysed directly (incubation time 20 to 30 sec.) in 50 μl PBS pH7.4. As control free CF (0.1 mM) in PBS was added to the cells.

Results:

TABLE 34

| Size and PI of formulations L-46-L-49 | |
|---|---|
| Formulation ID | Size [nm]/PI |
| L-46 | 281/0.22 |
| L-47 | 260/0.26 |
| L-48 | 285/0.26 |
| L-49 | 368/0.25 |

Transfection of HeLa-Cells with Liposomes Encapsulating Carboxyfluorescein:

Carboxyfluorescein is a pH-sensitive fluorescence probe which do not show a fluorescence signal in acidic environment (e.g. endosomes).

Figure 17:
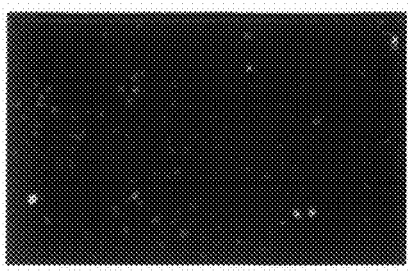
FIGS. 17 A and B show fluorescence microscopy images of Hela cells transfected with formulation L-46 or L-47, respectively (10×) (magnification: 100×).
Figure 17:
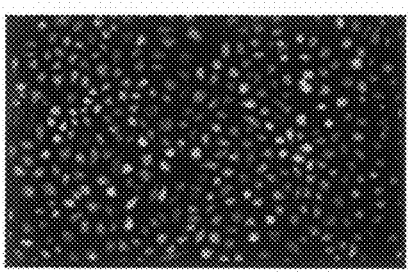
Figure 18:
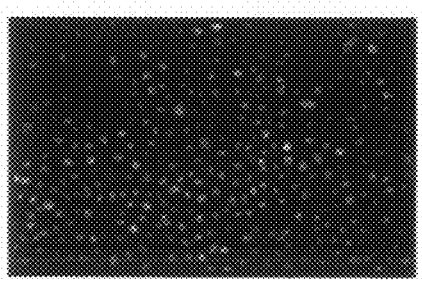
FIGS. 18 A and B show fluorescence microscopy images of Hela cells transfected with formulation L-48 or L-49, respectively (10×) (magnification: 100×).
Figure 18:
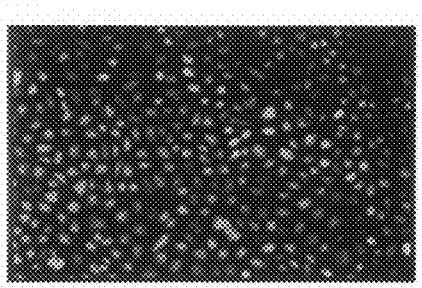

FIGS. 17 A and B and FIGS. 18 A and B show the fluorescence microscopy images of Hela cells transfected with formulations L-46-L-49. The fluorescence signal of the carboxyfluorescein is more intensive for formulations L-47 and L-49 having 10% Pal-PE in their membrane. With free CF no fluorescence signal was observed (data not shown).

Example 12

In Vitro Transfection Experiment with Liposomes Encapsulating siRNA Targeting Plk-1 or Non-Targeting Scrambled (scr) siRNA Preparation of Liposomes:

Liposomes were manufactured by an isopropanol- or ethanol-injection method. Lipid mixtures were dissolved in isopropanole/1% HCl (L-50 and L-51)) or ethanol (L-52 and L-53) at a lipid concentration of 6.7 mM. The lipid solution were injected into an appropriate siRNA solution (169 μg/ml) in 10 mM HAC, 300 mM sucrose, pH 4.0 (pH adjusted with Tris), resulting in a final alcohol concentration of 30%. The formed liposomal suspensions were shifted to pH 7.5 with twice the volume of 150 mM TRIS pH 8.0 (pH adjusted with HCl), and then dialyzed against 20 mM Tris, 280 mM Sucrose, pH 7.4 (pH adjusted with HCl) to remove non-encapsulated siRNA and the alcohol.

TABLE 35

Formulations L-50-L-53

| Formulation ID | Lipids | Mol % | siRNA |
|---|---|---|---|
| L-50 | POPC/DOTAP/Chems/Pal-PE | 25:28:47:10 | Plk-1 |
| L-51 | POPC/DOTAP/Chems/Pal-PE | 15:28:47:10 | scrambled |
| L-52 | POPC/DOTAP/Chems | 25:28:47 | Plk-1 |
| L-53 | POPC/DOTAP/Chems | 25:28:47 | scrambled |

Transfection Protocol:

HeLa cells were obtained from DSMZ (German Collection of Micro Organism and Cell Cultures) and maintained in DMEM. Media were purchased from Gibco-Invitrogen and supplemented with 10% FCS at 37° C. under 5% $CO_2$. The cells were plated at a density of $1.5 \times 10^4$ cells/ml and cultivated in 100 μl medium. After 16 h the liposomes containing siRNA were diluted in Optimem I (Gibco-Invitrogen) and 10 μl were added to the cells (110 μl final Volume and 9.1% FCS per well) (5 to 40 nM Plk1 or scramble siRNA). 10 μl Optimem I were also added to untreated cells and into wells without cells. In addition, as control free siRNA was added to the cells (10 to 80 nM Plk-1 or scrambled siRNA). Cell culture dishes were incubated for 72 h hours at 37° C. under 5% CO2. Transfection efficiency was analyzed using a cell proliferation/viability assay.

Cell Proliferation/Viability Assay

Cell proliferation/viability was determined by using the CellTiter-Blue Cell Viability assay (Promega, US). In brief, 72 hours after transfection, 20 μl CellTiter-Blue reagent were added to the wells. Following an incubation at 37° C. for 2.5 hours, 100 μL of the medium were transferred into the wells of a black microtiter plate (NUNC, Denmark). Fluorescence was recorded using a fluorescence plate reader (Ex. 550 nm/Em. 590 nm). On each plate the following controls were included: i) wells without cells but with medium (control for culture medium background fluorescence) and ii) wells with cells (untreated cells=mock-transfected cells). For calculation, the mean fluorescence value of the culture medium background was subtracted from all values of experimental wells (transfected and mock-transfected cells). The mean fluorescence values from each replicate transfection were normalized to the mean fluorescence value from mock-transfected cells, which was set as being 100%.

Results:

TABLE 36

Size and PI of formulations L-50-L-53

| Formulation ID | Size [nm]/PI |
|---|---|
| L-50 | 261/0.36 |
| L-51 | 213/0.32 |
| L-52 | 170/0.32 |
| L-53 | 154/0.26 |

Figure 19:
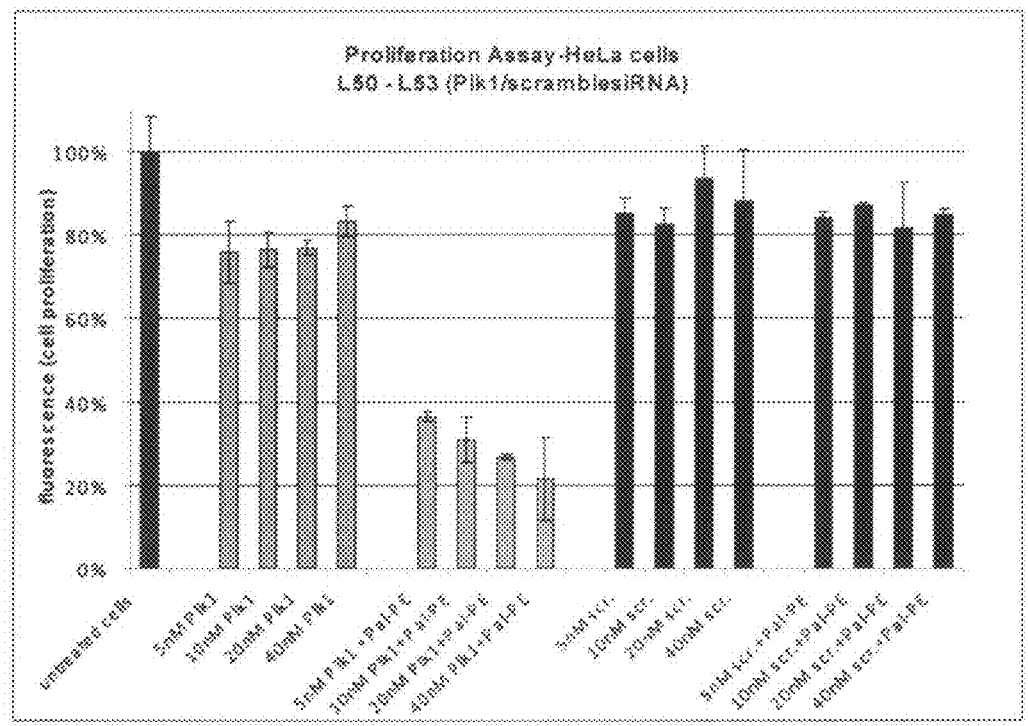
FIG. 19 shows the cell proliferation (expressed as % cell proliferation) of Hela cells transfected with formulations L-50-L-53 (5 to 40 nM Plk1-siRNA or scrambled siRNA).

Transfection of Hela cells with liposomes encapsulating siRNA targeting Plk-1 or non-targeting scrambled (scr) siRNA FIG. 19 shows the % cell proliferation after transfection of Hela cells with formulations L-50-L53. It becomes apparent that formulation L-50 comprising 10% of the TEE-lipid Pal-PE and encapsulating Plk-1 siRNA clearly reduces the cell proliferation down to about 20% proliferation. The reduction in cell proliferation is dose dependent. In contrast, formulation L-52 comprising no TEE-lipid and encapsulating Plk-1 siRNA can reduce cell proliferation of the Hela cells only to about 80% cell proliferation. Both formulations L-51 and L-53 encapsulating scrambled siRNA affect the proliferation of Hela cells only marginally.

Example 13

Fusogenicity of Liposomes Comprising Lipids with a TEE

Liposomes were prepared from mixtures comprising neutral or zwitterionic lipids (POPC/Chol 1:1) and 10 mol % of a TEE-lipid wherein the chain length of the hydrophobic moieties of the used TEEs was varied between 6 and 20. As control, liposomes without TEE-lipids and liposomes comprising lipids having alkyl chains lacking a carboxyl group as pH-sensitive hydrophilic moiety (C6-PE, C 12-PE, C 16-PE, C20-PE) were prepared.

TEE-Lipids Used in the Experiment:

| | | |
|---|---|---|
| w6-PE | w6-DPTAP | C6-PE |
| w12-PE | w12-DPTAP | C12-PE |
| w16-PE | w16-DPTAP | C16-PE |
| | w20-DPTAP | C20-PE |

TABLE 37

| Lipid 1 | Lipid 2 | TEE-Lipid or control | Mol % |
|---|---|---|---|
| POPC | Chol | w6-PE | 50:50:0 |
| POPC | Chol | w6-PE | 48.8:48.8:2.5 |
| POPC | Chol | w6-PE | 47.5:47.5:5 |
| POPC | Chol | w6-PE | 45:45:10 |
| POPC | Chol | w12-PE | 50:50:0 |
| POPC | Chol | w12-PE | 48.8:48.8:2.5 |
| POPC | Chol | w12-PE | 47.5:47.5:5 |
| POPC | Chol | w12-PE | 45:45:10 |
| POPC | Chol | w16-PE | 50:50:0 |
| POPC | Chol | w16-PE | 48.8:48.8:2.5 |
| POPC | Chol | w16-PE | 47.5:47.5:5 |
| POPC | Chol | w16-PE | 45:45:10 |
| POPC | Chol | w6-DPTAP | 50:50:0 |
| POPC | Chol | w6-DPTAP | 48.8:48.8:2.5 |
| POPC | Chol | w6-DPTAP | 47.5:47.5:5 |
| POPC | Chol | w6-DPTAP | 45:45:10 |
| POPC | Chol | w12-DPTAP | 50:50:0 |
| POPC | Chol | w12-DPTAP | 48.8:48.8:2.5 |
| POPC | Chol | w12-DPTAP | 47.5:47.5:5 |
| POPC | Chol | w12-DPTAP | 45:45:10 |
| POPC | Chol | w16-DPTAP | 50:50:0 |
| POPC | Chol | w16-DPTAP | 48.8:48.8:2.5 |
| POPC | Chol | w16-DPTAP | 47.5:47.5:5 |
| POPC | Chol | w16-DPTAP | 45:45:10 |
| POPC | Chol | w20-DPTAP | 50:50:0 |
| POPC | Chol | w20-DPTAP | 48.8:48.8:2.5 |
| POPC | Chol | w20-DPTAP | 47.5:47.5:5 |
| POPC | Chol | w20-DPTAP | 45:45:10 |
| POPC | Chol | C6-PE | 50:50:0 |
| POPC | Chol | C6-PE | 48.8:48.8:2.5 |
| POPC | Chol | C6-PE | 47.5:47.5:5 |
| POPC | Chol | C6-PE | 45:45:10 |
| POPC | Chol | C12-PE | 50:50:0 |
| POPC | Chol | C12-PE | 48.8:48.8:2.5 |
| POPC | Chol | C12-PE | 47.5:47.5:5 |
| POPC | Chol | C12-PE | 45:45:10 |
| POPC | Chol | C16-PE | 50:50:0 |
| POPC | Chol | C16-PE | 48.8:48.8:2.5 |
| POPC | Chol | C16-PE | 47.5:47.5:5 |
| POPC | Chol | C16-PE | 45:45:10 |

TABLE 37-continued

| Lipid 1 | Lipid 2 | TEE-Lipid or control | Mol % |
|---|---|---|---|
| POPC | Chol | C20-PE | 50:50:0 |
| POPC | Chol | C20-PE | 48.8:48.8:2.5 |
| POPC | Chol | C20-PE | 47.5:47.5:5 |
| POPC | Chol | C20-PE | 45:45:10 |

Fusability of the lipid mixtures was investigated using a lipid mixing assay, based on FRET. Liposomal mixtures described above were prepared in the presence of 0.75 mol % NBD-PE (N-(7-nitrobenz-2-oxa-1,3-diazol-4-yl)-1,2-dihexadecanoyl-sn-glycero-3-phosphoethanol-amine, triethylammonium salt). In addition neutral liposomes (POPC/DOPE 1:3) without TEE-lipid, single labelled with 0.75 mol % Rhodamine-PE (Lissamine™ rhodamine B 1,2-dihexadecanoyl-sn-glycero-3-phosphoethanolamine, triethylammonium salt) were prepared. NBD-PE single labelled liposomes were mixed with Rhodamine-PE single labelled POPC/DOPE 1:3 liposomes. Lipid fusion was monitored through the appearance of a FRET signal.

Lipids were dissolved in isopropanol and mixed. Liposomes were produced by adding buffer (acetic acid 10 mM, phosphoric acid 10 mM, NaOH, pH 7.5) to the alcoholic lipid mix, resulting in a final lipid concentration of 1.6 mM and a final isopropanol concentration of 12.2%. The NBD-labelled and Rh-labelled liposomes were combined in a ratio 1:1 and subsequent diluted 1:1 with the buffer mentioned above. Finally small aliquots of this mixed sample were brought to decreasing specific pH (HAc 50 mM, Phosphoric acid 50 mM, NaOH, pH 7.5-2.5) and incubated at 37° C. for 2 h. Liposomes were diluted again 1:1 in this step.

Samples were measured for fluorescence using two sets of filters: NBD/Rhodamine:460/590 nm and NBD/NBD:460/530 nm. FRET as a signal for membrane fusion was expressed as the ratio of emission (590 nm)/emission (530 nm). A background of 0.35 indicates background fluorescence and was therefore subtracted from the FRET signals.

The fusion can be expressed as $\Sigma$ FRET, the sum of all measured FRET signals between pH 2.5 and pH 7.5.

Figure 20:
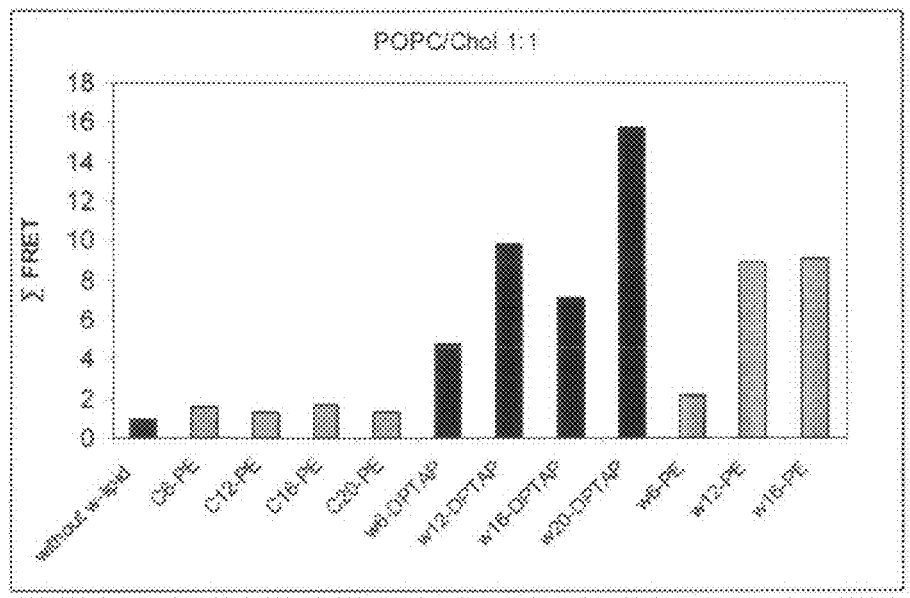
FIG. 20 shows the intensity of fusion (expressed as Σ FRET of all measured Fret signals over the pH range of between 7.5 and 2.5) for liposomes from POPC/Chol 1:1 without TEE-lipids or with 10% of different TEE-lipids or control lipids (C6-PE-C20-PE), respectively. Liposomes with TEE lipids were brought to fusion with liposomes from POPC/DOPE 1:3 without TEE lipids.

FIG. 20 shows the result of the experiment to detect the fusion ability of POPC/Chol 1:1 liposomes comprising 10 mol % TEE-lipids or control lipids as described above, respectively, with pure POPC/DOPE 1:3 liposomes. It becomes apparent that the liposomes comprising lipids with alkyl chains lacking a carboxyl group (C6-PE-C20-PE) are less fusogenic compared to the liposomes comprising lipids with a TEE.

Example 14

Fusability of Liposomes Comprising TEE-Lipids

Fusability of the lipid mixtures was investigated using a lipid mixing assay, based on FRET. Liposomes, single labelled with 0.75 mol % NBD-PE (N-(7-nitrobenz-2-oxa-1, 3-diazol-4-yl)-1,2-dihexadecanoyl-sn-glycero-3-phosphoethanol-amine, triethylammonium salt) or Rhodamine-PE (Lissamine™ rhodamine B 1,2-dihexadecanoyl-sn-glycero-3-phosphoethanolamine, triethylammonium salt), respectively, were prepared to monitor lipid fusion through the appearance of a FRET signal.

Lipids were dissolved in isopropanol and mixed. Liposomes were produced by adding buffer (acetic acid 10 mM, phosphoric acid 10 mM, NaOH, pH 7.5) to the alcoholic lipid mix, resulting in a final lipid concentration of 1.46 mM and a final isopropanol concentration of 13.2%. For the preparation of the liposomes a liquid handling robot (Perkin Elmer, Multiprobe II Ex) was used. The NBD-labelled and Rh-labelled liposomes were combined in a ratio 1:1 and subsequent diluted 1:1 with the buffer mentioned above. Finally small aliquots of this mixed sample were brought to decreasing specific pH (HAc 50 mM, Phosphoric acid 50 mM, NaOH, pH 7.5; 6.5; 5.5; 4.5; 3.5; 2.5) and incubated at 37° C. for 2 h. Liposomes were diluted again 1:1 in this step.

Samples were measured for fluorescence using two sets of filters: NBD/Rhodamine:460/590 nm and NBD/NBD:460/530 nm. FRET as a signal for membrane fusion was expressed as the ratio of emission (590 nm)/emission (530 nm). A background of 0.35 indicates background fluorescence and was therefore subtracted from the FRET signals.

The fusion can be expressed as $\Sigma$ FRET, the sum of all measured FRET signals between pH 2.5 and pH 7.5.

To evaluate the impact of TEE lipids on the fusogenicity of liposomes a screen with different lipid mixtures and different TEE-lipids was performed as described above. As indicated in table 38 for each amphoteric lipid pair 48 different formulations were tested in the fusion screen whereas the molar ratio of the amphoteric lipid pair and the neutral lipids was set to 0.66:

TABLE 38

| Amphoteric lipid pair (C/A = 0.5) | Neutral lipid systems (molar ratio) | TEE-lipids | Mol % TEE-Lipids |
|---|---|---|---|
| DOTAP/Chems | DOPE | w16-PE | 0/2.5/5/10 |
| | POPC/DOPE (0.3) | w16-DPTAP | |
| | POPC/Chol (1) | w20-DPTAP | |
| | POPC | | |
| DOTAP/DMG-Succ | DOPE | w16-PE | 0/2.5/5/10 |
| | POPC/DOPE (0.3) | w16-DPTAP | |
| | POPC/Chol (1) | w20-DPTAP | |
| | POPC | | |
| DC-Chol/DMG-Succ | DOPE | w16-PE | 0/2.5/5/10 |
| | POPC/DOPE (0.3) | w16-DPTAP | |
| | POPC/Chol (1) | w20-DPTAP | |
| | POPC | | |
| MoChol/Chems | DOPE | w16-PE | 0/2.5/5/10 |
| | POPC/DOPE (0.3) | w16-DPTAP | |
| | POPC/Chol (1) | w20-DPTAP | |
| | POPC | | |
| MoChol/DMG-Succ | DOPE | w16-PE | 0/2.5/5/10 |
| | POPC/DOPE (0.3) | w16-DPTAP | |
| | POPC/Chol (1) | w20-DPTAP | |
| | POPC | | |
| DmC4Mo2/DMG-Succ | DOPE | w16-PE | 0/2.5/5/10 |
| | POPC/DOPE (0.3) | w16-DPTAP | |
| | POPC/Chol (1) | w20-DPTAP | |
| | POPC | | |

Results:

The impact factor of a TEE-lipid on the fusogenicity of the liposomal formulations can be determined from the experimental data by calculating the gradient of the $\Sigma$ FRET between 0% TEE-lipid and 10% TEE-lipid for each formulation. The fusogenicity of nearly all formulations in table 38 can be improved by TEE-lipids in the lipid mixture.

A comparison of the gradients for the different neutral lipid systems reveals that the impact of a TEE lipid on the fusogenicity of a liposomal formulation may depend on the neutral lipids used in the formulations. Table 39 summarizes the mean impact factors and the mean $\Sigma$FRET for 0% and for 10% TEE-lipids for the neutral lipid systems, calculated over all formulations shown in table 38. It becomes apparent that the impact of TEE-lipids on lipid mixtures comprising very fusogenic, hexagonal phase forming lipids such as DOPE or mixtures with high amounts of DOPE is lower than in lipid mixture comprising a specific amount of a stable phosphatidylcholine and a hexagonal phase forming lipid, such as Chol. Lipid mixtures comprising only a stable phosphatidylcholine such as POPC as neutral lipid can be improved as well by TEE-lipids but also to a lesser extent than mixtures with a specific amount of a hexagonal phase forming lipid, such as Chol or DOPE.

TABLE 39

| Neutral lipid system | Mean impact factor | Mean Σ Fret 0% TEE | Mean Σ Fret 10% TEE |
|---|---|---|---|
| DOPE | 13 | 4.66 | 6.24 |
| POPC/DOPE (0.3) | 13 | 3.10 | 4.32 |
| POPC/Chol (1) | 19 | 0.98 | 2.97 |
| POPC | 11 | 0.21 | 1.33 |

Example 15

In Vitro Transfection Experiment with Liposomes Encapsulating siRNA Targeting Plk-1 or Non-Targeting Scrambled (scr) siRNA Preparation of Liposomes:

Liposomes were manufactured by an isopropanol-injection method. Lipids were dissolved in isopropanol and mixed. Liposomes were produced by adding siRNA solution (163.2 or 81.5 µg/ml) in NaAc 20 mM, Sucrose 300 mM, pH 4.0 (pH adjusted with HAc) to the alcoholic lipid mix, resulting in a final alcohol concentration of 30%. The formed liposomal suspensions were shifted to pH 7.5 with twice the volume of $Na_2HPO_4$ 136 mM, NaCl 100 mM (pH 9), resulting in a final lipid concentration of 1.4 mM and a final isopropanol concentration of 10%. For the preparation of the liposomes a liquid handling robot (Perkin Elmer, Multiprobe II Ex) was used.

TABLE 40

| Formulation ID | Lipids | Mol % | siRNA |
|---|---|---|---|
| L-54 | POPC/Chol/DOTAP/Chems | 20:20:20:40 | Plk-1 |
| L-55 | POPC/Chol/DOTAP/Chems | 20:20:20:40 | scrambled |
| L-56 | POPC/Chol/DOTAP/Chems/w16-PE | 19,5:19,5:19,5:39:2,5 | Plk-1 |
| L-57 | POPC/Chol/DOTAP/Chems/w16-PE | 19,5:19,5:19,5:39:2,5 | scrambled |
| L-58 | POPC/Chol/DOTAP/Chems/w16-PE | 19:19:19:38:5 | Plk-1 |
| L-59 | POPC/Chol/DOTAP/Chems/w16-PE | 19:19:19:38:5 | scrambled |
| L-60 | POPC/Chol/DOTAP/Chems/w16-PE | 18:18:18:36:10 | Plk-1 |
| L-61 | POPC/Chol/DOTAP/Chems/w16-PE | 18:18:18:36:10 | scrambled |
| L-62 | POPC/Chol/MoChol/Chems | 20:20:20:40 | Plk-1 |
| L-63 | POPC/Chol/MoChol/Chems | 20:20:20:40 | scrambled |
| L-64 | POPC/Chol/MoChol/Chems/w16-PE | 19,5:19,5:19,5:39:2,5 | Plk-1 |
| L-65 | POPC/Chol/MoChol/Chems/w16-PE | 19,5:19,5:19,5:39:2,5 | scrambled |
| L-66 | POPC/Chol/MoChol/Chems/w16-PE | 19:19:19:38:5 | Plk-1 |
| L-67 | POPC/Chol/MoChol/Chems/w16-PE | 19:19:19:38:5 | scrambled |
| L-68 | POPC/Chol/MoChol/Chems/w16-PE | 18:18:18:36:10 | Plk-1 |
| L-69 | POPC/Chol/MoChol/Chems/w16-PE | 18:18:18:36:10 | scrambled |

Transfection Protocol:

HeLa cells were obtained from DSMZ (German Collection of Micro Organism and Cell Cultures) and maintained in DMEM. Media were purchased from Gibco-Invitrogen and supplemented with 10% FCS at 37° C. under 5% $CO_2$. The cells were plated at a density of $2 \times 10^4$ cells/ml and cultivated in 100 µl medium. After 16 h the liposomes containing siRNA were diluted in PBS (Gibco-Invitrogen) and 110 µl were added to the cells (110 µl final Volume and 9.1% FCS per well) (5 to 80 nM Plk1 or scramble siRNA). 10 µl PBS were also added to untreated cells and into wells without cells. In addition, as control free siRNA was added to the cells (10 to 80 nM Plk-1 or scrambled siRNA). Cell culture dishes were incubated for 72 h hours at 37° C. under 5% CO2. Transfection efficiency was analyzed using a cell proliferation/viability assay.

Cell Proliferation/Viability Assay

Cell proliferation/viability was determined by using the CellTiter-Blue Cell Viability assay (Promega, US). In brief, 72 hours after transfection, 20 µl CellTiter-Blue reagent were added to the wells. Following an incubation at 37° C. for 2.5 hours, 100 µl of the medium were transferred into the wells of a black microtiter plate (NUNC, Denmark). Fluorescence was recorded using a fluorescence plate reader (Ex. 550 nm/Em. 590 nm). On each plate the following controls were included: i) wells without cells but with medium (control for culture medium background fluorescence) and ii) wells with cells (untreated cells=mock-transfected cells). For calculation, the mean fluorescence value of the culture medium background was subtracted from all values of experimental wells (transfected and mock-transfected cells). The fluorescence values from each transfection were normalized to the mean fluorescence value from mock-transfected cells, which was set as being 100%.

Figure 21:
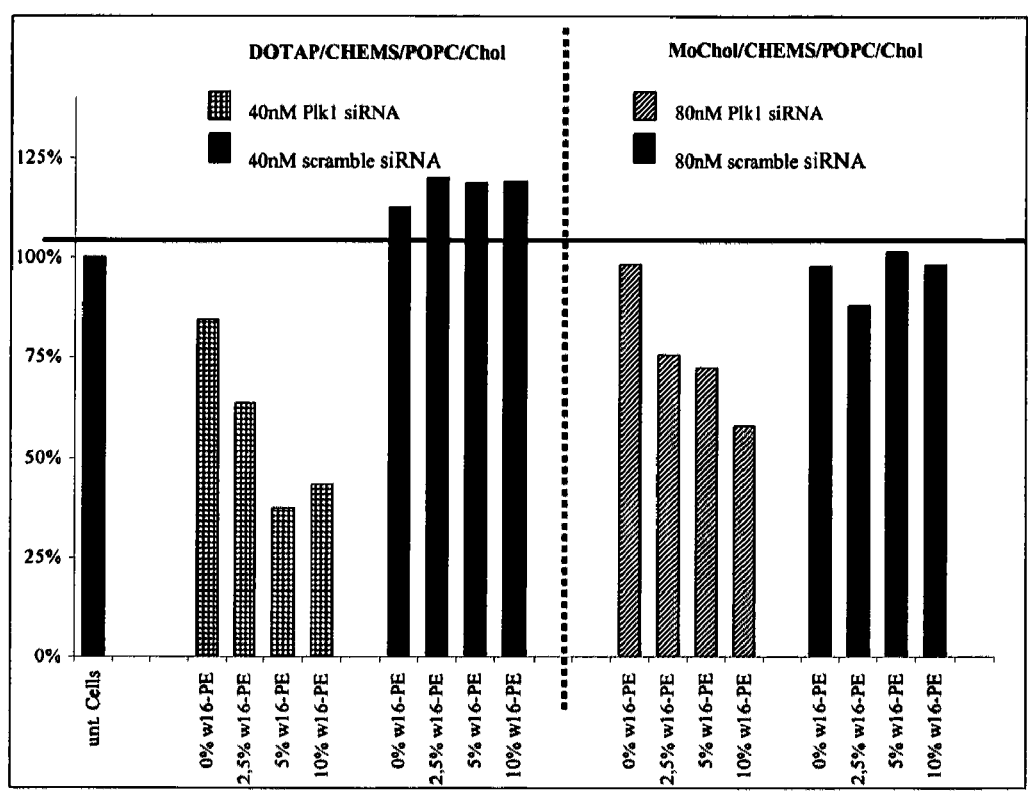
FIG. 21 shows the relative cell proliferation of Hela cells transfected with formulations L-54-L-69 encapsulating Plk1-siRNA or scrambled siRNA.

Results:

FIG. 21 shows the relative cell proliferation after transfection of Hela cells with formulations L-54-L-69. All formulations comprising w16-PE and encapsulating Plk-1 siRNA reduces the cell proliferation. FIG. 22 shows that the reduction in cell proliferation is dose dependent. In contrast, formulation comprising no TEE-lipid and encapsulating Plk-1 siRNA influence cell proliferation of the Hela cells only to a lesser extent. The formulations encapsulating scrambled siRNA do not have an effect on Hela cells proliferation.

Example 16

Synthesis of 6-{2-[2,3-Bis-hexadecanoyloxy-propoxy)-hydroxy-phosphoryl-oxy]-ethylamino}-hexanoic acid (w6-PE)

Step a. Synthesis of 6-Oxo hexanoic acid 10 g 6-hydroxy capronic acid (1 eq.) was oxidized with 32.6 g PCC (Pyridinium chlorochromate) (2 eq.) for about 20 min at 37° C. as described in example 1, step a.

Step b. Synthesis of w6-PE

In a second step w6-PE was synthesized by reductive amination as described in example 1, step b using 1.11 g 6-Oxo hexanoic acid, 4.72 g DPPE, 6.0 g sodium cyano-boronhydride ($NaCNBH_3$) and 3.78 g pyridine. After 4 hours the solvent was removed and the residue was dissolved in 2.5 liter chloroform/methanol/$H_2O$ 500:100:4 and 100 ml $H_2O$ were added. After separation of the two phases the solvent of the organic phase was removed and the residue was purified by column chromatography on silica gel (eluent: chloroform/methanol/$H_2O$ 500:300:4). The solvent was removed and the residue was washed with 10 ml $H_2O$. The mixture was fritted and the crude product was purified by two further column cromatographies on silica gel (eluent 1: chloroform/methanol/$H_2O$ 500:300:4; eluent 2: chloroform/methanol/$H_2O$ 500:100:4). Purity of the product was judged by thin layer chromatography, $^1$H-NMR and LC-MS.

Example 17

Synthesis of 12-{2-[2,3-Bis-hexadecanoyloxy-propoxy)-hydroxy-phosphoryl-oxy]-ethylamino}-dodecanoic acid (w12-PE)

Step a. Synthesis of 12-Oxo-dodecanoic acid 14 g 12-hydroxy dodecanoic acid (1 eq.) was oxidized with 27.9 g PCC (Pyridinium chlorochromate) (2 eq.) for about 25 min at 37° C. as described in example 1, step a.

Step b. Synthesis of w12-PE

In a second step w12-PE was synthesized by reductive amination as described in example 1, step b using 1.2 g 12-Oxo-dodecanoic acid, 3.88 g DPPE, 4.93 g sodium cyanoboronhydride (NaCNBH$_3$) and 3.1 g pyridine. After 5 hours the solvent was removed and to the residue 100 ml $H_2O$ was added and the mixture was then sonicated. After a centrifugation step the residue was purified by column chromatography on silica gel (eluent: chloroform/methanol/$H_2O$ 500:100:4). Purity of the product was judged by thin layer chromatography, $^1$H-NMR and HPLC.

Example 18

Synthesis of 21-{2-[(2,3-Bis-hexadecanoyloxy-propoxy)-hydroxy-phosphoryloxy]-ethylamino}-henicosanoic acid (w21-PE)

Step a. Synthesis of 11-Iodo undecanoic acid

11-Iodo undecanoic acid was synthesized according to Bergbreiter, J. Org. Chem., 40 (6), (1975) 779-782. Briefly, 250 g 11-Bromo undecanoic acid, 325 g Sodium iodide and 2 liter acetone were refluxed under $N_2$ atmosphere for 24 hours. The mixture was divided and added to 4 liter $H_2O$ each. The mixtures were fritted and the crude product recrystallized from methanol and finally characterized by the melting point.

Step b. Synthesis of 11-Iodo-undecanoic acid ethyl ester

11-Iodo-undecanoic acid ethyl ester was synthesized according to Bergbreiter, J. Org. Chem., 40/6 (1975) 779. Briefly, 246.6 g 11-Iodo undecanoic acid, 440 ml dry ethanol, 440 ml dry toluol and 5 ml $H_2SO_4$ (98%) were combined. The mixture was distilled whereby about 400 ml aceotrope was removed at 75° C. or 76° C., respectively. Then 15 g $K_2CO_3$ was added and after 5 min the mixtures was filtered and finally distilled at a bath temperature of 115° C. The resulting brown oil was purified by filtration through a frit filled with silica gel (eluent: acetic acid ethyl ester/petrol ether 1:7). The final product was characterized by $^1$H-NMR and thin layer chromatography.

Step c. Synthesis of Docos-21-enoic acid ethyl ester

Docos-21-enoic acid ethyl ester was synthesized according to Bergbreiter et al., J. Org. Chem., 40 (6), (1975), 779-782.

Grignard Reagent:

1.55 g magnesium were mixed under $N_2$ atmosphere with 20 ml dry tetrahydrofurane (THF) and a iodine crystal. Then 11.09 g 11-chloro-1-undecene were dissolved in 22 ml dry THF and this solution was added slowly and dropwise at 30° C. to the magnesium mixture. After the addition of a further iodine crystal the mixture was refluxed for 45 min. Then the mixture was allowed to react and after 25 min refluxed again for 45 min.

Main Reaction:

Under $N_2$ atmosphere 11.19 g copper (1) iodide and 100 ml THF were mixed and cooled down to −78° C. Then 36.73 ml Methyllithium (1.6 M in Ether) were added dropwise. The mixture was brought to 0° C. and then cooled down again to −78° C. The grignard reagent was added dropwise before the mixture was stirred for one hour. Then the temperature raised stepwise to 20° C. and decreased again to −78° C. 11-Iodo-undecanoic acid ethyl ester from step b was dissolved in 20 ml dry THF and added dropwise to the reaction mixture which was then allowed to stir for about one hour. The mixture was then thawed and after one night added to 300 ml saturated NH$_4$Cl solution and 200 ml Ether. The solid was removed by filtration and the phase of the filtrate were separated and the aqueous phase was washed three times with ether. The combined organic phases were washed with brine and dried over Na$_2$SO$_4$. The organic solvent was then removed by a rotary evaporator and the crude product was purified by column chromatography on silica gel (eluents: 1. petrolether; 2. acetic acid ethyl ester/petrolether 1:20) and subsequent recrystallization from ethanol. Finally, purity of the product was judged by thin layer chromatography and $^1$H-NMR.

Step d. Synthesis of 22-Hydroxy-docosanoic acid

22-Hydroxy-docosanoic acid was synthesized according to Mori et al., Liebigs Ann. Chem., (1991), 253-257. Briefly, under $N_2$ atmosphere 6.6 g Docos-21-enoic acid ethyl ester and 30 ml THF were combined and cooled down to 0° C. Then 0.5 eq. (9 ml) borane/THF complex was added dropwise and the mixture was allowed to stir for 2 hours at room temperature. After the addition of 1.2 ml $H_2O$ the suspension was again cooled down to 0° C. and 15 ml 3M NaOH and 2 ml 35% $H_2O_2$ were added. The mixture was stirred for one hour at 50° C. Then the temperature was brought to room temperature and the pH was adjusted to pH 2-3 with 2N HCl. The solid was fritted, washed with $H_2O$, codistilled three times with CHCl$_3$ and recrystallized from CHCl$_3$. After a further treatment with NaOH (3M in $H_2O$) in THF at 50° C. over 1.5 days the pH was again adjusted to pH 2-3 and the crude product was fritted, washed with $H_2O$ and codistilled two times with CHCl$_3$. The product was characterized by thin layer chromatography and $^1$H-NMR.

Step e. Synthesis of 22-Oxo-docosanoic acid 3.9 g 22-Hydroxy-docosanoic acid (1 eq.) was oxidized with 4.72 g PCC (Pyridinium chlorochromate) (2 eq.) for about 2 hours under reflux as described in example 1, step a.

Step f. Synthesis of w21-PE

In this step w21-PE was synthesized by reductive amination as described in example 1, step b using 0.62 g 22-Oxo-docosanoic acid, 1.21 g DPPE, 1.54 g sodium cyano-boronhydride (NaCNBH$_3$) and 0.97 g pyridine. After 5 hours the solvent was removed and to the residue 40 ml $H_2O$ was added and the mixture was then sonicated. After the solid was fritted the crude product was purified by column chromatography on silica gel (eluent: chloroform/methanol/$H_2O$ 500:100:4). Purity of the product was judged by thin layer chromatography, $^1$H-NMR and HPLC.

Example 19
Synthesis of Hexadecanoic acid 1-{[(5-carboxy-pentyl)-dimethyl-ammonium]methyl-2-hexadecanoyloxy-ethyl ester (w6-DPTAP)
Reaction scheme:
Step a:
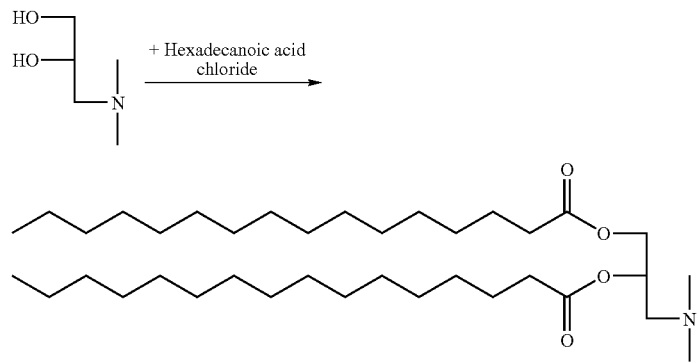
Step b:
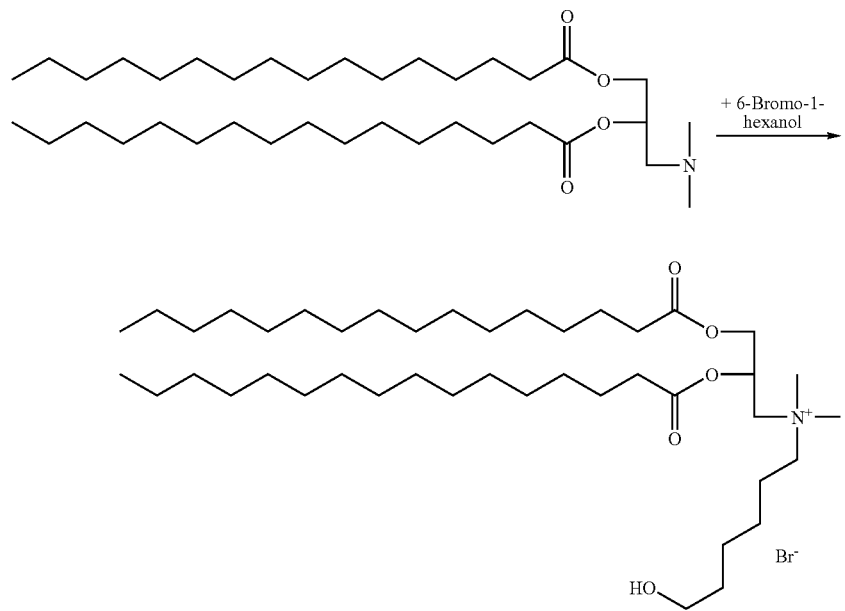
Step c:
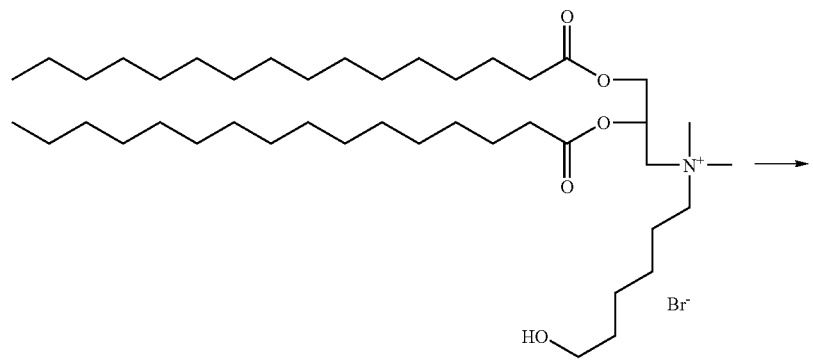

-continued

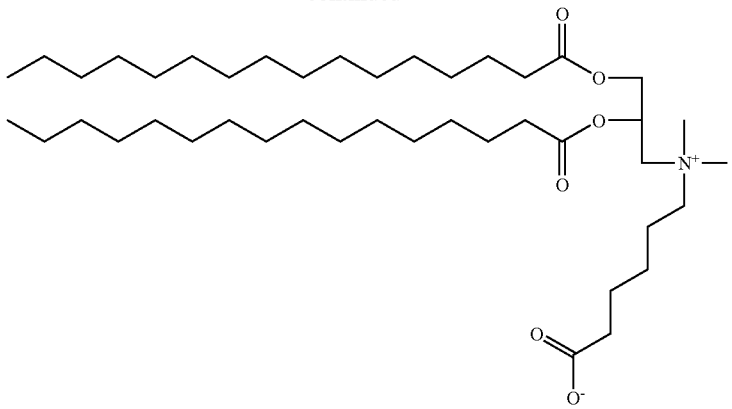

Step a: Synthesis of Hexadecanoic acid 1-dimethylaminomethyl-2-hexadecanoyloxy-ethyl ester 43.17 g 3-(dimethylamino)-1,2-propanediol were dissolved on 1000 ml dichloromethane. After the addition of 73.3 g triethylamine and 0.01 g 4-dimethylamino pyridine the mixture was cooled down to 0° C. Then 199.18 g hexadecanoic acid chloride, dissolved in 100 ml dichloromethane, were added dropwise. After the addition of another 100 ml dichloromethane the mixture was brought to room temperature and allowed to stir over night. The mixture was filtered and the residue washed with 300 ml dichloromethane. The solvent of the filtrate was removed using a rotary evaporator and the crude product was purified by column chromatography on silica gel (eluent: acetic acid ethyl ester/petrolether 1:1). The product was characterized by $^1$H-NMR.

Step b: Synthesis of (2,3-Bis-hexadecanoyloxy-propyl)-(6-hydroxyhexyl)-dimethyl-ammonium bromide Under $N_2$ atmosphere 32.39 g Hexadecanoic acid 1-dimethylaminomethyl-2-hexadecanoyloxy-ethyl ester, 9.84 g 6-bromo-1-hexanole and 500 ml acetonitrile were mixed and refluxed for about one day. Then the mixture was cooled down to 5° C. and after about 7 hours the white solid was filtered and recrystallized from acetic acid ethyl ester. The purity of the product was judged by thin layer chromatography.

Step c: Synthesis of w6-DPTAP 8.31 g (2,3-Bis-hexadecanoyloxy-propyl)-(6-hydroxyhexyl)-dimethyl-ammonium bromide were suspended in 40 ml dichloromethane and under stirring 0.035 g TEMPO in 20 ml dichloromethane were added. 0.268 g KBr were dissolved in 3 ml $H_2O$ and added to the reaction. After the addition of 0.22 g Aliquat 336™ the mixture was cooled with an ice bath and 1 g $NaHCO_3$ dissolved in 67 ml sodium hypochlorite solution was added dropwise. The mixture was allowed to stir for 5 hours at room temperature before 200 ml $CHCl_3$ was added. The phases were separated and the organic phase was dried over $Na_2SO_4$. The solvent was removed and the crude product was purified by column chromatography on silica gel (eluent: chloroform/methanol 4:1). The product was characterized by $^1$H-NMR and LC-MS.

Example 20

Synthesis of Hexadecanoic acid 1-{[(11-carboxyundecyl)-dimethyl-ammonium]methyl-2-hexadecanoyloxy-ethyl ester (w12-DPTAP)

Step a: Synthesis of (2,3-Bis-hexadecanoyloxy-propyl)-(12-hydroxydodecyl)-dimethyl-ammonium bromide Synthesis was performed as described in example 19 step b using 22.47 g Hexadecanoic acid 1-dimethylaminomethyl-2-hexadecanoyloxy-ethyl ester, 10 g 12-bromo-1-dodecanole and 500 ml acetonitrile. The crude product was recrystallized from acetic acid ethyl ester/methanol 9:1 and purity of the product was judged by thin layer chromatography and $^1$H-NMR.

Step b: Synthesis of w-12-DPTAP w-12-DPTAP was synthesized as described in example 19 step c using 9.21 g (2,3-Bis-hexadecanoyloxy-propyl)-(12-hydroxydodecyl)-dimethyl-ammonium bromide, 0.035 g TEMPO, 0.268 g KBr, 0.22 g Aliquat™ and 1 g $NaHCO_3$ dissolved in 67 ml sodium hypochlorite. The crude product was purified by two column chromatographies on silica gel (eluent 1: chloroform/methanol 4:1; eluent 2: chloroform/methanol 8:1). The product was characterized by $^1$H-NMR and LC-MS.

Example 21

Synthesis of Hexadecanoic acid 1-{[(15-carboxypentadecyl)-dimethyl-ammonium]methyl-2-hexadecanoyloxy-ethyl ester (w16-DPTAP)

Step a: Synthesis of (2,3-Bis-hexadecanoyloxy-propyl)-(16-hydroxyhexadecyl)-dimethyl-ammonium bromide Synthesis was performed as described in example 19 step b using 18.55 g Hexadecanoic acid 1-dimethylaminomethyl-2-hexadecanoyloxy-ethyl ester, 10 g 16-bromo-1-hexadecanole and 500 ml acetonitrile. The crude product was recrystallized from acetic acid ethyl ester/methanol 10:1 and purity of the product was judged by thin layer chromatography and $^1$H-NMR.

Step b: Synthesis of w-16-DPTAP w-16-DPTAP was synthesized as described in example 19 step c using 14 g (2,3-Bis-hexadecanoyloxy-propyl)-(16-hydroxyhexadecyl)-dimethyl-ammonium bromide, 0.05 g TEMPO, 0.382 g KBr, 0.3 g Aliquat™ and 1.43 g NaHCO$_3$ dissolved in 95.6 ml sodium hypochlorite. The crude product was purified by column chromatography on silica gel (eluent: chloroform/methanol 8:1). The product was characterized by $^1$H-NMR and LC-MS.

Example 22

Synthesis of Hexadecanoic acid 1-{[(19-carboxy-nonadecyl)-dimethyl-ammonium]methyl-2-hexadecanoyloxy-ethyl ester (w20-DPTAP)

Step a: Synthesis of Icosane-1,20-diol

Icosane-1,20-diol was synthesized according to Yoon et al., J. Org. Chem. 1973, 38(16), 2786-2792. Briefly, under N$_2$ atmosphere to 25 g eicosanedioic acid 100 ml THF was added. Then 474.5 ml of borane/THF complex was added dropwise over 1.5 hours. The mixture was refluxed over night before 200 ml THF/H$_2$O 1:1 were added dropwise. Under further stirring 100 g NaHCO$_3$ dissolved in 250 ml H$_2$O was added and two hours later 1000 ml H$_2$O was added to the mixture and the precipitate was removed by filtration. At the next day and the day after next a white precipitate was removed by filtration from the mixture, dried and recrystallized from acetic acid ethyl ester. The product was characterized by thin layer chromatography and $^1$H-NMR.

Step b: Synthesis of 20-Bromo-icosan-1-ol

20-Bromo-icosan-1-ol was synthesized according to Uneyama et al, Tetrahedron Letters, 1991, 32(11), 1459-1462. Briefly, 400 ml petrolether were heated before 240 ml petrolether, 20.34 g icosane-1,20-diol and 280 ml HBr (48% in H$_2$O) were added. The mixture was refluxed over night and incubated at room temperature for another day. The precipitate was then removed by filtration and dissolved in 300 ml dichloromethane. The solution was dried over Na$_2$SO$_4$ and filtered through silica gel. The solvent was removed and the crude product finally recrystallized from petrolether. Purity of the product was judged by $^1$H-NMR.

Step c: Synthesis of (2,3-Bis-hexadecanoyloxy-propyl)-(20-hydroxy-icosyl)-dimethyl-ammonium bromide Synthesis was performed as described in example 19 step b using 17.89 g Hexadecanoic acid 1-dimethylaminomethyl-2-hexadecanoyloxy-ethyl ester, 11.33 g 20-Bromo-icosan-1-ol and 500 ml acetonitrile. The crude product was recrystallized from chloroform/methanol 3:1 and purity of the product was judged by thin layer chromatography and $^1$H-NMR.

Step d: Synthesis of w-20 DPTAP w-20-DPTAP was synthesized as described in example 19 step c using 11.45 g (2,3-Bis-hexadecanoyloxy-propyl)-(20-hydroxy-icosyl)-dimethyl-ammonium bromide, 0.039 g TEMPO, 0.294 g KBr, 0.2 g Aliquat™ and 1.1 g NaHCO$_3$ dissolved in 73.7 ml sodium hypochlorite. The crude product was filtered through silica gel and after a washing step with chloroform/methanol 4:1 the product was characterized by $^1$H-NMR and LC-MS.

Example 23

Synthesis of Hexadecanoic acid 3-{[2-(15-carboxy-pentadecanoylamino)-ethoxy]-hydroxy-phosphoryloxy}-2-hexadecanoyloxy-propyl ester (w 16-Amid-PE)

Reaction Scheme:
Step a:

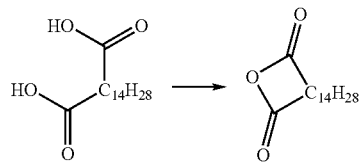

Step b:

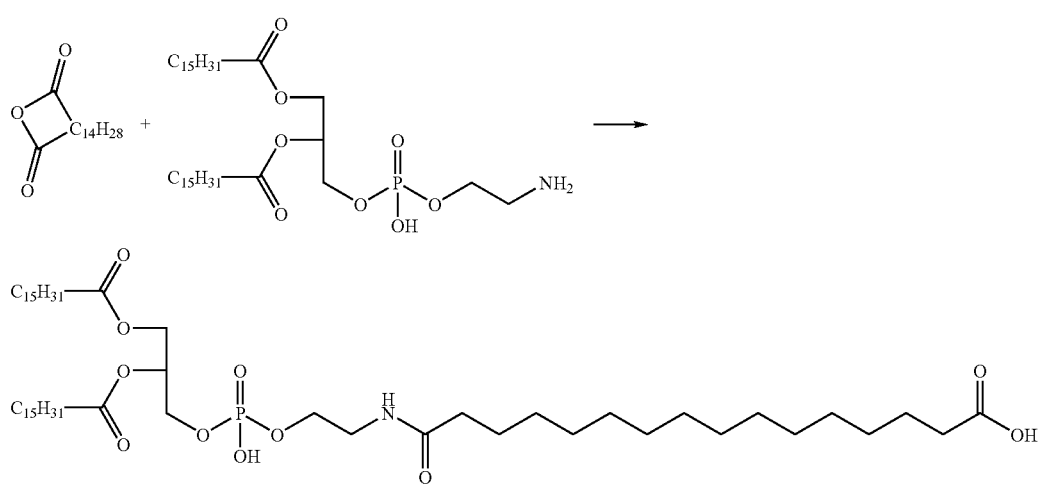

Step a: Synthesis of Oxacycloheptadecane-2,17-dione 3 g hexadecanedicarboxlic acid and 4.5 ml acetanhydride were refluxed over night. Then the solvent was removed and the crude product recrystallized from acetonitril.

Step b: Synthesis of w16-Amid-PE

Under N2 atmosphere 8 g DPPE, 160 ml chloroform, 3.1 g Oxacycloheptadecane-2,17-dione, 4.57 g pyridine and 0.1 g dimethyl aminopyridine were mixed and stirred at 70° C. over night. Then the solvent was removed by a rotary evaporator and the residue was under sonication resuspended in 160 ml 1N HCl. At the next day the mixture was fritted and the solid was washed with 80 ml 1N HCl and then dissolved in chloroform/methanol/$H_2O$ 65:25:4. The aqueous phase was removed and the organic solvent was removed by a rotary evaporator. The crude product was purified by column chromatography on silica gel (eluent: chloroform/methanol 9:1). The product was characterized by $^1$H-NMR and LC-MS.

Example 23

Synthesis of Octanedioic acid mono cholesteryl ester (cholesterol hemisuberate)

Step a: Synthesis of Oxonane-2,9-dione

Under $N_2$ atmosphere 50 g suberic acid and 100 ml acetanhydride were refluxed for 2 hours. The solvent was evaporated and 200 ml acetonitrile were added to the residue and the mixture was kept in a freezer over night. Then the mixture was fritted and the resulting residue was washed with 50 ml acetonitrile and dried.

Step b: Synthesis of Octanedioic acid mono cholesteryl ester 35 g cholesterol and 21.2 g oxepane-2,7-dione were weighed into a round-bottomed flask. Under $N_2$ atmosphere 250 ml toluol, 14.3 ml pyridine and 0.22 g 4-dimethylamino pyridine were added. The reaction was refluxed for 1 days. Then the solvent was evaporated and the residue was dissolved in dichloromethane/acetic acid ethylester (96:4) and purified by a frit on silica gel (eluent: dichloromethane/acetic acid ethylester (96:4)). The product was characterized by $^1$H-NMR.

Example 24

Synthesis of N-(3-Amino-propyl)-N'-[3-(4-{3-[4-(3-aminopropylamino)-butylamino]-propylamino}-butylamino)-propyl]-butane-1,4-diamine (compound 4)

Reaction scheme:

Step a: Synthesis of {4-[(3-Amino-propyl)-tert-butoxycarbonylamino]-butyl}-(3-tert-butoxycarbonylaminopropyl)-carbamic acid tert-butyl ester (compound 6)

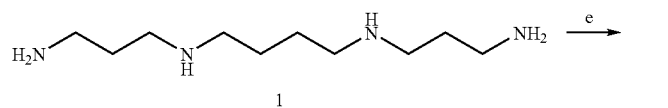

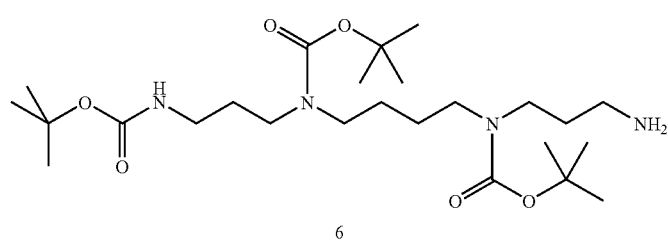

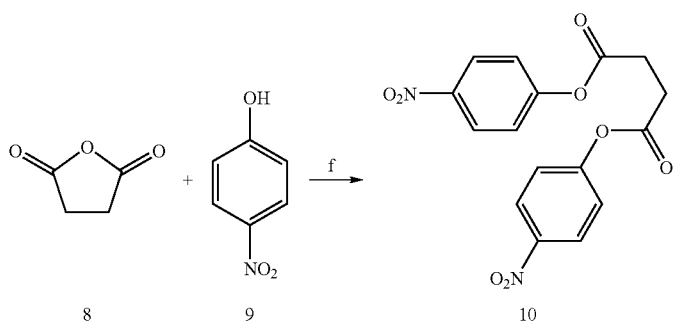

105
-continued
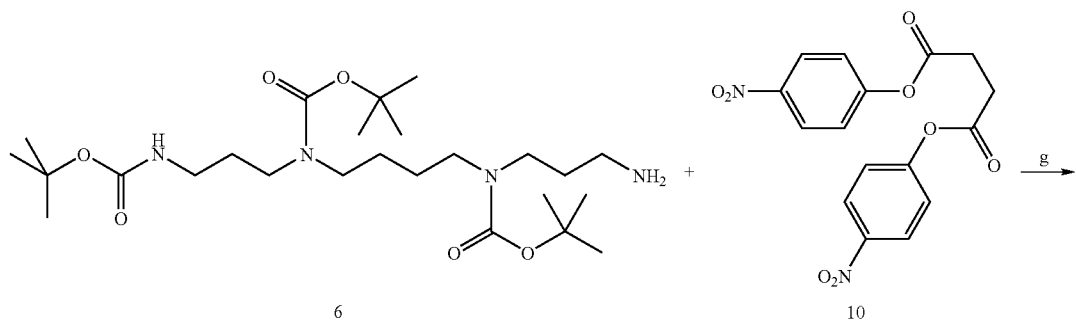
106
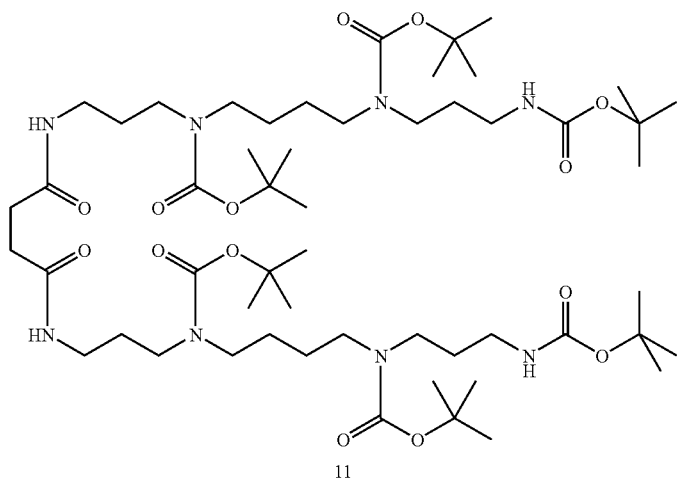
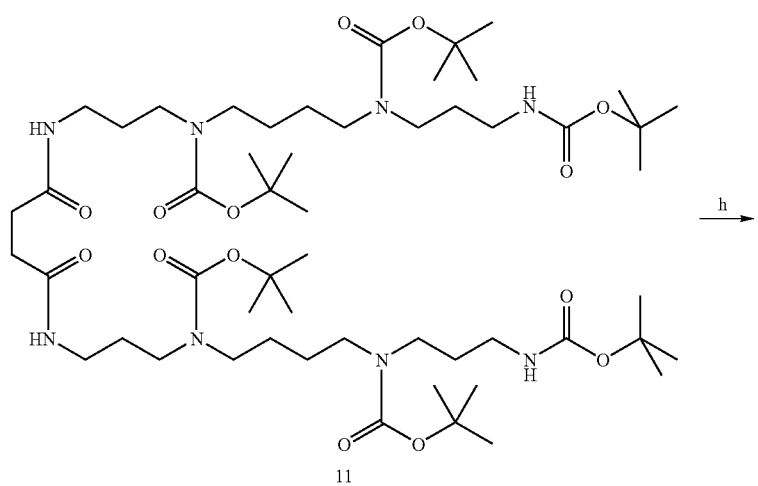

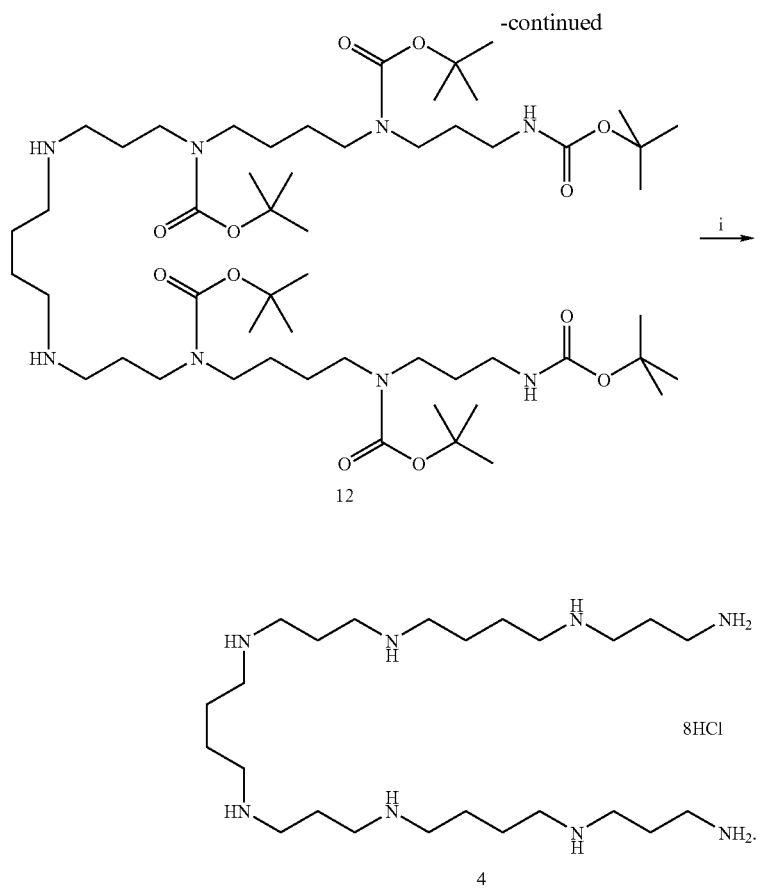

The compound was synthesized according to Geall et al., Chem. Commun. 1998, 2035. Briefly, 10.12 g spermine and 150 ml methanol were stirred and cooled down to −75° C. Then 5.95 ml trifluoro acetic acid ethylester (99%) were added dropwise. The temperature was raised to 0° C., 42.8 ml di-tert-butyl-dicarbonate (BOC2O) were added and the reaction was stirred at room temperature overnight. About 50 ml of the solvent was removed by rotary evaporation, replaced with 50 ml $H_2O$ and extracted three times with 200 ml diethylether. The organic phase was dried over $Na_2SO_4$, filtered and evaporated under vacuum; the crude product, a colourless oil, was purified by column chromatography on silica gel (eluent 1: dichloromethane/methanol/$NH_4OH$ (25%) 70:10:1; eluent 2: dichloromethane/methanol/$NH_4OH$ (25%) 50:10:1). The product was characterized by 1H-NMR and LC-MS.

Step b: Synthesis of Succinic acid bis-(4-nitro-phenyl)ester (compound 10)

36.3 g DCC (N,N'-dicyclohxylcarbodiimide), 0.2 g 4-dimethylaminopyridine, 46.7 g p-nitrophenol, and 16 g succinic acid anhydride and 600 ml acetic acid ethylester were mixed in a round bottom flask and stirred at room temperature for three days. The solvent was removed by rotary evaporation and the yellow residue was recrystallized from 150 ml chloroform. The white product was washed with chloroform, dried and characterized by thin layer chromatography and $^1$H-NMR.

Step c: Synthesis of compound 11

Compound 11 was synthesized according to Graminski et al., Bioorg. Med. Chem. Lett. 2002, 35-40. Briefly, 8.8 g of compound 6 was dissolved in 100 ml dimethylformamide. Then 1.95 N-methyl morpholine and 2.84 g of compound 10 were added and the mixture allowed to stir at room temperature overnight. The solvent was removed by rotary evaporation and the crude product, a yellow oil, was purified by column chromatography on silica gel (eluent: acetic acid ethylester/methanol 9:1). The solvent was removed and the residue dissolved in 100 ml acetic acid ethylester and 100 ml petrolether. The mixture was washed three times with 150 ml $H_2O$ and the organic phases were dried over $Na_2SO_4$. After a filtration the solvent was removed by rotary evaporation and product characterized by thin layer chromatography, LC-MS and $^1$H-NMR.

Step d: Synthesis of compound 12

Under $N_2$ atmosphere 4.68 g of compound 11 were dissolved in 40 ml tetrahydrofurane and the reaction mixture was cooled with an ice bath. Then 10.8 ml of a borane-dimethylsulfide-complex (2M in tetrahydrofurane) were added and the reaction was allowed to stir overnight at room temperature. After the addition of 100 ml petrolether, 20 ml acetic acid ethylester and 2 ml methanol the solution was chromatographed on a silica gel column (flash chromatography; eluent: acetic acid ethylester). The solvent was removed and the crude product, a colourless oil, was purified by a further column chromatography on silica gel (eluent: acetic acid ethylester). The product was characterized by LC-MS and $^1$H-NMR.

Step e: Synthesis of compound 4

0.92 g of compound 12 was dissolved in 10 ml methanol. The solution was refluxed before a mixture of 15 ml HCl (37%) and 20 ml HCl (2N) was added drop wise. The reaction mixture was refluxed overnight. After the addition of 10 ml $H_2O$ the mixture was extracted two times with 50 ml dichloromethane. The solvent of the aqueous phase was removed and the product was characterized by $^1$H-NMR and LC-MS.

Example 25

Derivatization of Compound 4 with TEE's

Samples of 50 mg (0.1 mmol) of compound 4 were alkylated with ω-bromo-α-carboxylic acids. Briefly, 0.3 mmol or 0.6 mmol of either 6-bromohexanoic acid or 10-bromodecanoic acid or an equimolar mixture between the two were dissolved in 2 ml dry DMF and 0.1 mmol of compound 4 was added to each reaction. The mixture was incubated at 50° C. over night, cooled to room temperature and the degree of alkylation was determined by mass spectroscopy.

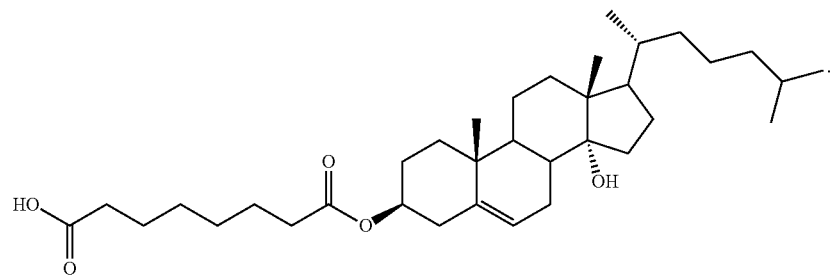

What is claimed is:

1. A formulation comprising a composition of at least one lipid moiety covalently linked to one or more transfection enhancer elements (TEE's), wherein the at least one lipid moiety comprises a sterol and wherein the one or more TEE's are defined according to the formula:

wherein the pH sensitive hydrophilic moiety of each of the one or more TEE's is a weak acid having a pKa of between 2 and 6 and is located distally from the link between the lipid moiety and the TEE, and wherein the hydrophobic moiety of each of the one or more TEE's is independently an alkyl carbon chain comprising 12 to 20 carbon atoms;
wherein the composition comprises the general formula (XIV)

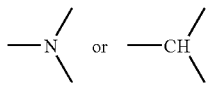

wherein Xa is bound at the 3' position of the sterol and is —OPO$_3$—; —OPO$_2$—CH$_2$—; -pyrophosphate-; —OSO$_3$—; —OSO$_2$—; —O—; —NH—; —S—; —N(H)C(O)—; —C(O)—, —C(O)N(H)—; —OC(O)N(H)—; —N(H)C(O)O—; —OC(O)—; —C(O)O—; —N=CH—; —CH=N—; —CH$_2$—; —S—S—; —N(R$_{13}$)(R$_{14}$)—;

—N⟨ or —CH⟨ wherein R$_{13}$ and R$_{14}$ are independently H or lower alkyl and wherein one of R$_{13}$ or R$_{14}$ may be absent;
Ya is absent or a non-branched, branched or cyclic substituted or unsubstituted alkyl, alkenyl, alkylene, alkynyl, or an aryl group with 1 to 8 carbon atoms, wherein Ya is substituted with one or more groups are selected from —OH; —NH$_2$; —N(R$_{13}$)(R$_{14}$); —COOH; a sugar; an amino acid; a di- or tripeptide; an α-hydroxyacid, a β-hydroxyacid or a dihydroxyacid, wherein R$_{13}$ and R$_{14}$ are defined above;
Za is absent or selected from —O—; —S—; —N(H)C(O)—; —C(O)N(H)—; —C(O)O—; —OC(O)N(H)—; —C(O)—; —C(O)N(H)—; —N(H)C(O)O—; —NH—; —N(R$_{13}$)(R$_{14}$)—; —CH=N—; —OC(O)—; —N=CH—; —S—S—; —NH$_2$; —(NH$_3$)—; —(N(R$_{13}$)(R$_{14}$)(R$_{15}$))—; —C(O)OH; —OH; —C(O)H; —C(O)OR$_{16}$; —C(O)NH$_2$; wherein R$_{15}$ is defined as R$_{13}$ and R$_{14}$ above and wherein R$_{16}$ is lower alkyl;
wherein the sterol is selected from cholesterol, sitosterol, campesterol, desmosterol, fucosterol, 22-ketosterol, 20-hydroxysterol, stigmasterol, 22-hydroxycholesterol, 25-hydroxycholesterol, lanosterol, 7-dehydrocholesterol, dihydrocholesterol, 19-hydroxycholesterol, 5α-cholest-7-en3β-ol, 7-hydroxycholesterol, epicholesterol, ergosterol, and/or dehydroergosterol; and
wherein the dotted lines represent possible graft positions of the one or more TEE's.

2. The formulation as claimed in claim 1, wherein the composition forms a lipid assembly selected from liposomes, micelles, inverted micelles, cubic or hexagonal lipid phases, cochleates, emulsions, double emulsions and other multimeric assemblies that are constituted substantially of lipids, oils and/or amphiphiles.

3. The formulation as claimed in claim 1, further comprising neutral and/or cationic and/or anionic lipids.

4. The formulation as claimed in claim 3, wherein the neutral lipids are selected from phosphatidylcholines; phosphatidylethanolamines; sphingolipids; ceramides; cerebrosides; sterol-based lipids; and/or derivatives thereof.

5. The formulation as claimed in claim 4, wherein the neutral lipids are selected from DMPC, DPPC, DSPC, POPC, DOPC, DMPE, DPPE, DSPE, POPE, DOPE, Diphythanoyl-PE, sphingomyelin, ceramide and/or cholesterol.

6. The formulation as claimed in claim 3, wherein the cationic lipids are selected from DOTAP, DMTAP, DPTAP, DC-Chol, DAC-Chol, DODAP, DOEPC, TC-Chol, DOTMA, DORIE, DDAP, CTAB, CPyC, DPIM, CHIM, MoChol, His-Chol, BGSC, BGTC, DOSPER, DOSC, DOGSDO, DmC4Mo2, DmC3Mo2, C3Mo2, C3Mo3, C4Mo4, C5Mo2, C6Mo2, C8Mo2, PipC2Chol, MoC2Chol, MoC3Chol, N-methyl-PipChol, PyrroC2Chol, PyC2Chol, ImC3Chol, PipeC2Chol and derivatives thereof.

7. The formulation as claimed in claim 3, wherein the anionic lipids are selected from phosphatidylglycerols, phosphatidylserines, phosphatidylinositols, phosphatidic acids, CHEMS, anionic sterol-derivatives, cetylphosphate, diacylglycerol hemisuccinates, cardiolipins and/or derivatives thereof.

8. The formulation as claimed in claim 1, wherein the amount of the composition is between 0.1 mol % and 90 mol %.

9. The formulation as claimed in claim 2, wherein the lipid assembly is an amphoteric liposome.

10. The formulation as claimed in claim 9, further comprising one or more amphoteric lipids.

11. The formulation as claimed in claim 10, wherein the amphoteric lipids are selected from HistChol, HistDG, iso-HistSuccDG, Acylcarnosin, HCChol, Hist-PS and EDTA-Chol.

12. The formulation as claimed in claim 9, further comprising an amphoteric lipid mixture selected from (i) a stable cationic lipid and a chargeable anionic lipid, (ii) a chargeable cationic lipid and chargeable anionic lipid or (iii) a stable anionic lipid and a chargeable cationic lipid, and optionally comprising one or more neutral or zwitterionic lipids.

13. The formulation as claimed in claim 12, comprising between 20 and 90 mol % of the amphoteric lipid mixture and between 2 and 20 mol % of the composition.

14. The formulation as claimed in claim 12, wherein the molar ratio of the stable cationic lipid to the chargeable anionic lipid (C/A ratio) is between 0.3 and 0.7.

15. The formulation as claimed in claim 12, wherein the molar ratio of the chargeable cationic lipid to the chargeable anionic lipid (C/A ratio) is between 0.3 and 3.

16. The formulation as claimed in claim 12, wherein the amphoteric lipid mixture is selected from DOTAP/Chems, DOTAP/DMG-Succ, DOTAP/DOG-Succ, DODAP/Chems, DODAP/DMG-Succ, DODAP/DOG-Succ, DDAB/Chems, DDAB/DMG-Succ, DDAB/DOG-Succ, DC-Chol/Chems, DC-Chol/DMG-Succ, DC-Chol/DOG-Succ, DAC-Chol/Chems, DAC-Chol/DMG-Succ, DAC-Chol/DOG-Succ, TC-Chol/Chems, TC-Chol/DMG-Succ, TC-Chol/DOG-Succ, MoChol/Chems, MoChol/DMG-Succ, HisChol/DOG-Succ, HisChol/Chems, HisChol/DMG-Succ, HisChol/DOG-Succ, Chim/Chems, Chim/DMG-Succ, Chim/DOG-Succ, DmC4Mo2/Chems, DmC4Mo2/DMG-Succ and DmC4Mo2/DOG-Succ.

17. The formulation as claimed in claim 9, wherein the amphoteric liposome is unilamellar, oligolamellar or multi-lamellar and the size of the amphoteric liposome varies between 50 and 1000 nm.

18. The formulation as claimed in claim 1, further comprising at least one active pharmaceutical ingredient.

19. The formulation as claimed in claim 18, wherein the active pharmaceutical ingredient is a nucleic acid-based drug, selected from DNA plasmids, polynucleotides and oligonucleotides.

20. The formulation as claimed in claim 19, wherein the nucleic acid-based drug is capable of being transcribed in a vertebrate cell into one or more RNAs, wherein the RNAs are mRNAs, shRNAs, miRNAs or ribozymes, and wherein the mRNAs code for one or more proteins or polypeptides.

21. The formulation as claimed in claim 19, wherein the nucleic acid-based drug is a circular DNA plasmid, a linear DNA construct or an mRNA.

22. The formulation as claimed in claim 19, wherein the nucleic acid-based drug is an oligonucleotide.

23. The formulation as claimed in claim 22, wherein the oligonucleotide is a decoy oligonucleotide, an antisense oligonucleotide, an siRNA, an agent influencing transcription, an agent influencing splicing, Ribozymes, DNAzymes or Aptamers.

24. The formulation as claimed in claim 22, wherein the oligonucleotide is directed against tumor targets.

25. The formulation as claimed in claim 24, wherein the tumor targets are selected from CEACAM6, BCL-2, EPHA2, CTNNB1, RhoA, PLK1, XIAP, Telomerase, Cyclin D1, K-Ras, EG5, Ki67, androgen receptor, FoxM1, Akt1, VEGF, KSB and CDC25B.

26. A pharmaceutical composition comprising the formulation as claimed in claim 18 and a pharmaceutically acceptable vehicle therefor.

27. The formulation as claimed in claim 1, wherein the pH sensitive hydrophilic moiety of the one or more TEE's is a carboxylic acid or comprises the following structure:

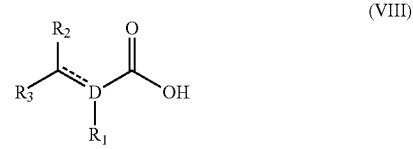

(VIII)

wherein the dotted line represents an optional double bond;
$R_1$, $R_2$, and $R_3$ are independently the hydrophobic moiety of the one or more TEE's, a hydrogen, a linear, branched or cyclic, unsubstituted or substituted $C_1$-$C_{10}$ alkyl, alkylene, alkoxy-, alkoxyalkyl-, alkylthio-, alkylthioalkyl-, hydroxy-, mercapto-, oxo-, formyl-, nitro-, cyano-, halo-, trihalomethyl group or a heteroalkyl group having 0-5 sites of unsaturation, or an aryl group, wherein any of $R_1$, $R_2$, or $R_3$ optionally comprise 0-5 heteroatoms selected from —O— or —S—;
D is a carbon atom or an unsubstituted or substituted cyclic alkyl or aryl group having 0-3 sites of unsaturation and comprising 0-5 heteroatoms selected from —O—, —S—, and the substituents of D are selected from alkyl-, alkylene-, alkenyl-, alkynyl-, alkoxy-, alkoxyalkyl-, alkylthio-, alkylthioalkyl-, hydroxy-, mercapto-, oxo-, formyl-, cyano-, halo- or a trihalomethyl group.

28. The formulation as claimed in claim 1, wherein the composition comprises the following structure:

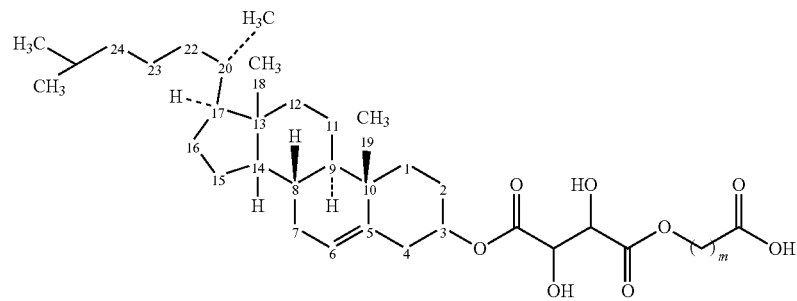

wherein m=12-40.

29. The formulation as claimed in claim 1, wherein the composition comprises the following structure:

```
                          SEQUENCE LISTING

<160> NUMBER OF SEQ ID NOS: 4

<210> SEQ ID NO 1
<211> LENGTH: 21
<212> TYPE: DNA
<213> ORGANISM: Artificial
<220> FEATURE:
<223> OTHER INFORMATION: Synthetic Primer

<400> SEQUENCE: 1
agaccuaccu ccggaucaat t                                                    21

<210> SEQ ID NO 2
<211> LENGTH: 21
<212> TYPE: DNA
<213> ORGANISM: Artificial
<220> FEATURE:
<223> OTHER INFORMATION: Synthetic Primer

<400> SEQUENCE: 2
uugauccgga gguaggucut t                                                    21

<210> SEQ ID NO 3
<211> LENGTH: 21
<212> TYPE: DNA
<213> ORGANISM: Artificial
<220> FEATURE:
<223> OTHER INFORMATION: Synthetic Primer

<400> SEQUENCE: 3
aacuggguaa gcgggcgcat t                                                    21

<210> SEQ ID NO 4
<211> LENGTH: 21
<212> TYPE: DNA
<213> ORGANISM: Artificial
<220> FEATURE:
<223> OTHER INFORMATION: Synthetic Primer

<400> SEQUENCE: 4
ugcgcccgcu uacccaguut t                                                    21
```